C010252050B2

United States Patent
Kreis et al.

(10) Patent No.: US 10,252,050 B2
(45) Date of Patent: Apr. 9, 2019

(54) PULSE APPLICATOR

(71) Applicant: Pulse Biosciences, Inc., Burlingame, CA (US)

(72) Inventors: Mark P. Kreis, San Francisco, CA (US); David J. Danitz, San Jose, CA (US); Cameron D. Hinman, Thurmond, NC (US)

(73) Assignee: PULSE BIOSCIENCES, INC., Hayward, CA (US)

( * ) Notice: Subject to any disclaimer, the term of this patent is extended or adjusted under 35 U.S.C. 154(b) by 9 days.

(21) Appl. No.: 15/595,684

(22) Filed: May 15, 2017

(65) Prior Publication Data

US 2017/0326361 A1 Nov. 16, 2017

Related U.S. Application Data

(60) Provisional application No. 62/337,270, filed on May 16, 2016.

(51) Int. Cl.
*A61N 1/00* (2006.01)
*A61N 1/32* (2006.01)
*A61B 18/14* (2006.01)
*A61N 1/18* (2006.01)
(Continued)

(52) U.S. Cl.
CPC .............. *A61N 1/32* (2013.01); *A61B 18/14* (2013.01); *A61N 1/18* (2013.01); *A61N 1/20* (2013.01); *A61N 1/30* (2013.01)

(58) Field of Classification Search
CPC ... A61N 1/05; A61N 1/18; A61N 1/20; A61N 1/30; A61N 1/32; A61B 18/12; A61B 18/14; A61B 2017/00154; A61B 2018/00577; A61B 2018/1405; A61B 2018/142; A61B 2018/1475
See application file for complete search history.

(56) References Cited

U.S. PATENT DOCUMENTS

| 5,568,035 A | 10/1996 | Kato et al. |
| 5,635,776 A | 6/1997 | Imi |
| 5,774,348 A | 6/1998 | Druce et al. |

(Continued)

FOREIGN PATENT DOCUMENTS

| WO | 2011/146498 A2 | 11/2011 |
| WO | 2014/060854 A1 | 4/2014 |

(Continued)

OTHER PUBLICATIONS

Baker et al., "Stacking Power MOSFETs for use in High Speed Instrumentation," Rev. Sci. Instrum., American Institute of Physics, Dec. 1992, vol. 63, No. 12, pp. 5799-5801.

(Continued)

*Primary Examiner* — Mallika D Fairchild
(74) *Attorney, Agent, or Firm* — Kilpatrick Townsend & Stockton LLP

(57) ABSTRACT

The pulse applicator includes a first arm, including a first electrode, a second arm, including a second electrode, and a spacer. The first arm, the spacer, and the second arm are movably connected, and define a gap between the first arm and the second arm. The first electrode, the gap, and the second electrode are selectively alignable, and the first electrode and the second electrode are configured to deliver an electrical field across the gap in response to an electrical pulse received across the first and second electrodes.

41 Claims, 41 Drawing Sheets

(51) Int. Cl.
*A61N 1/20* (2006.01)
*A61N 1/30* (2006.01)

(56) References Cited

U.S. PATENT DOCUMENTS

| | | | |
|---|---|---|---|
| 5,907,484 | A | 5/1999 | Kowshik et al. |
| 6,008,690 | A | 12/1999 | Takeshima et al. |
| 6,026,003 | A | 2/2000 | Moore et al. |
| 6,048,789 | A | 4/2000 | Vines et al. |
| 6,137,276 | A | 10/2000 | Rudolph |
| 6,326,177 | B1 | 12/2001 | Schoenbach et al. |
| 6,831,377 | B2 | 12/2004 | Yampolsky et al. |
| 7,496,401 | B2 | 2/2009 | Bernabei |
| 7,767,433 | B2 | 8/2010 | Kuthi et al. |
| 7,855,904 | B2 | 12/2010 | Kirbie et al. |
| 7,937,143 | B2 | 5/2011 | Demarais et al. |
| 8,688,227 | B2 | 4/2014 | Nuccitelli et al. |
| 8,822,222 | B2 | 9/2014 | Beebe et al. |
| 9,724,155 | B2 | 8/2017 | Nuccitelli |
| 2001/0025177 | A1 | 9/2001 | Woloszko et al. |
| 2002/0193833 | A1 | 12/2002 | Dimmer et al. |
| 2003/0204161 | A1 | 10/2003 | Ferek-Petric |
| 2004/0080964 | A1 | 4/2004 | Buchmann |
| 2004/0240241 | A1 | 12/2004 | Chueh et al. |
| 2006/0062074 | A1 | 3/2006 | Gundersen et al. |
| 2006/0079886 | A1 | 4/2006 | Orszulak et al. |
| 2006/0090723 | A1 | 5/2006 | Stuart |
| 2006/0139977 | A1 | 6/2006 | Oicles et al. |
| 2007/0066957 | A1 | 3/2007 | Demarais et al. |
| 2007/0129626 | A1 | 6/2007 | Mahesh et al. |
| 2008/0031337 | A1 | 2/2008 | Hasegawa et al. |
| 2008/0077189 | A1 | 3/2008 | Ostroff et al. |
| 2009/0198231 | A1 | 8/2009 | Esser et al. |
| 2009/0299362 | A1 | 12/2009 | Long et al. |
| 2010/0038971 | A1 | 2/2010 | Sanders et al. |
| 2010/0042095 | A1 | 2/2010 | Bigley et al. |
| 2010/0063496 | A1 | 3/2010 | Trovato et al. |
| 2010/0240995 | A1 | 9/2010 | Nuccitelli |
| 2010/0318082 | A1 | 12/2010 | Nuccitelli et al. |
| 2010/0331758 | A1 | 12/2010 | Davalos et al. |
| 2011/0015630 | A1 | 1/2011 | Azure |
| 2011/0118729 | A1 | 5/2011 | Heeren et al. |
| 2011/0144641 | A1 | 6/2011 | Dimalanta et al. |
| 2011/0160514 | A1 | 6/2011 | Long et al. |
| 2011/0270249 | A1 | 11/2011 | Utley et al. |
| 2012/0277763 | A1 | 11/2012 | Greenblatt et al. |
| 2012/0310230 | A1 | 12/2012 | Willis et al. |
| 2012/0315704 | A1 | 12/2012 | Beebe et al. |
| 2013/0018441 | A1 | 1/2013 | Childs |
| 2013/0150935 | A1 | 6/2013 | Weissberg et al. |
| 2013/0302409 | A1 | 11/2013 | Fuchs et al. |
| 2013/0345697 | A1 | 12/2013 | Garcia et al. |
| 2014/0046322 | A1 | 2/2014 | Callas et al. |
| 2014/0081256 | A1 | 3/2014 | Carmel et al. |
| 2014/0228835 | A1 | 8/2014 | Mielekamp et al. |
| 2014/0277219 | A1 | 9/2014 | Nanda |
| 2014/0336638 | A1 | 11/2014 | Deem et al. |
| 2014/0358066 | A1 | 12/2014 | Nuccitelli et al. |
| 2015/0032100 | A1 | 1/2015 | Coulson et al. |
| 2015/0065946 | A1 | 3/2015 | Gehl et al. |
| 2015/0272657 | A1 | 10/2015 | Yates et al. |
| 2017/0245928 | A1 | 8/2017 | Xiao et al. |
| 2017/0246455 | A1 | 8/2017 | Athos et al. |
| 2017/0319851 | A1 | 11/2017 | Athos et al. |
| 2017/0360504 | A1 | 12/2017 | Nuccitelli et al. |
| 2018/0078755 | A1 | 3/2018 | Kreis |
| 2018/0110557 | A1 | 4/2018 | Muratori et al. |
| 2018/0154142 | A1 | 6/2018 | Guo et al. |

FOREIGN PATENT DOCUMENTS

| | | |
|---|---|---|
| WO | 2016/089781 A1 | 6/2016 |
| WO | 2017/151260 A1 | 9/2017 |
| WO | 2017/151261 A1 | 9/2017 |
| WO | 2017/200954 A1 | 11/2017 |
| WO | 2017/201394 A1 | 11/2017 |
| WO | 2018/053539 A1 | 3/2018 |
| WO | 2018/075946 A1 | 4/2018 |
| WO | 2018/089506 A1 | 5/2018 |

OTHER PUBLICATIONS

Bhosale et al., "Design and Simulation of 50 kV, 50 A Solid State Marx Generator," International Conference on Magnetics, Machines & Drives (AICERA- 2014 iCMMD), IEEE 2014, pp. 1-5.

Carey et al., "Marx Generator Design and Performance," Applied Physical Electronics, L.C., 2002, 4 pages.

Casey et al., "Solid-State Marx Bank Modulator for the Next Generation Linear Collider," Conference Record of the 26th International Power Modulator Symposium and 2004 High Voltage Workshop (PMC), San Francisco, California, May 23-26, 2004, IEEE 2004, pp. 257-260.

Cook et al., "Design and Testing of a Fast, 50 kV Solid-State Kicker Pulser," IEEE 2002, pp. 106-109.

Gaudreau et al., "Solid-State Pulsed Power Systems for the Next Linear Collider," IEEE 2002, pp. 298-301.

International Application No. PCT/US2017/015881, Invitation to Pay Additional Fees and, Where Applicable, Protest Fee, dated Mar. 15, 2017, 2 pages.

Jiang et al., "Marx Generator Using Power Mosfets," IEEE 2009, pp. 408-410.

Kirbie et al., "An All Solid State Pulse Power Source for High PRF Induction Accelerators," IEEE 1998, pp. 6-11.

Krasnykh et al., "A Solid State Marx Type Modulator for Driving a TWT," Conference Record of the 24th International Power Modulator Symposium 2000, p. 209-211.

Okamura et al. "Development of the High Repetitive Impulse Voltage Generator Using Semiconductor Switches," IEEE 1999, pp. 807-810.

Redondo et al., "Solid-State Marx Generator Design with an Energy Recovery Reset Circuit for Output Transformer Association," Power Electronics Conference, IEEE, 2007, 5 pages.

Richter-Sand et al., "Marx-Stacked IGBT Modulators for High Voltage, High Power Applications," IEEE 2002, pp. 390-393.

Sack et al., "Design Considerations for a Fast Stacked-MOSFET Switch," IEEE Transactions on Plasma Science, vol. 41, No. 10, Oct. 2013, pp. 2630-2636.

Yao et al., "FPGA-Controlled All-Solid-State Nanosecond Pulse Generator for Biological Applications," IEEE Transactions on Plasma Science, vol. 40, No. 10, Oct. 2012, pp. 2366-2372.

PCT/US2017/015884, "International Search Report and Written Opinion" dated Apr. 21, 2017, 12 pages.

PCT/US2017/015881, "International Search Report and Written Opinion" dated May 25, 2017, 13 pages.

PCT/US2017/032744, "International Search Report and Written Opinion," dated Jul. 21, 2017, 11 pages.

Garon et al., "In Vitro and In Vivo Evaluation and a Case Report of Intense Nanosecond Pulsed Electric Field as a Local Therapy for Human Malignancies", Int. J. Cancer, vol. 121, 2007, pp. 675-682.

Gundersen et al., "Nanosecond Pulse Generator Using a Fast Recovery Diode", IEEE 26.sup.th Power Modulator Conference, 2004, pp. 603-606.

International Application No. PCT/US2015/63025, International Search Report and Written Opinion dated Apr. 21, 2016, 9 pages.

Nader Yatim et al., "RIPK1 and NF—κB signaling in dying cells determines cross-priming of CD8+ T cells," Science, Oct. 2015, vol. 350, Issue 6258, pp. 328-335, sciencemag.org.

PCT/US2017/052340, "International Search Report and Written Opinion", dated Jan. 8, 2018, 12 pages.

Tang et al., "Diode Opening Switch Based Nanosecond High Voltage Pulse Generators for Biological and Medical Applications", IEEE Transactions on Dielectrics and Electrical Insulation, vol. 14, No. 4, 2007, pp. 878-883.

Wang et al., "Solid-State High Voltage Nanosecond Pulse Generator," IEEE Pulsed Power Conference, 2005, pp. 1199-1202.

PCT/US2017/060654, "International Search Report and Written Opinion," dated Feb. 27, 2018, 18 pages.

(56) References Cited

OTHER PUBLICATIONS

Anand et al., "Adaptive Immune Response to Nano-Pulse Stimulation (NPS)," Nov. 11, 2016, Poster presentation at the 31st Annual Meeting and Associated Programs of the Society for Immunotherapy of Cancer, Retrieved from the Internet: URL: http://pulsebiosciences.com/assets/Pulse%20AIR%20poster.pdf, retrieved on Mar. 13, 2018.

Anand et al., "Nano-Pulse Electro-Signaling treatment of murine tumors significantly reduces the percentage of regulatory T cells in the treated tumor," Journal for Immunotherapy of Cancer: 31st Annual Meeting and Associated Programs of the Society for Immunotherapy of Cancer (SITC 2016), Part Two, National Harbor, MD, USA, Nov. 16, 2016, p. 214.

Beebe, S. J., "Hepatocellular carcinoma ablation and possible immunity in the age of nanosecond pulsed electric fields," Journal of Hepatocellular Carcioma, May 2015, No. 2, pp. 49-55.

McDaniel et al., "Nanosecond pulsed electric field treatment of tumor cell lines triggers immunogenic cell death (ICD)," Nov. 11, 2016, Poster presentation at the 31st Annual Meeting and Associated Programs of the Society for Immunotherapy of Cancer (SITC 2016), National Harbor, MD, USA; Retrieved from the Internet: URL: http://pulsebiosciences.com/assets/Pulse%20ICD%20poster.pdf, retrieved on Mar. 13, 2018.

McDaniel et al., "P329 Nanosecond pulsed electric field treatment of tumor cell lines triggers immunogenic cell death (ICD)," Journal for ImmunoTherapy of Cancer: 31st Annual Meeting and Associated Programs of the Society for Immunotherapy of Cancer (SITC 2016): part two: National Harbor, MD, USA, Nov. 16, 2016, p. 175.

PCT/US2017/057698, "International Search Report" dated Feb. 27, 2018, 3 pages.

PCT/US2017/064685, "International Search Report" dated Mar. 22, 2018, 5 pages.

PCT/US2018/019213, "International Search Report" dated May 22, 2018, 4 pages.

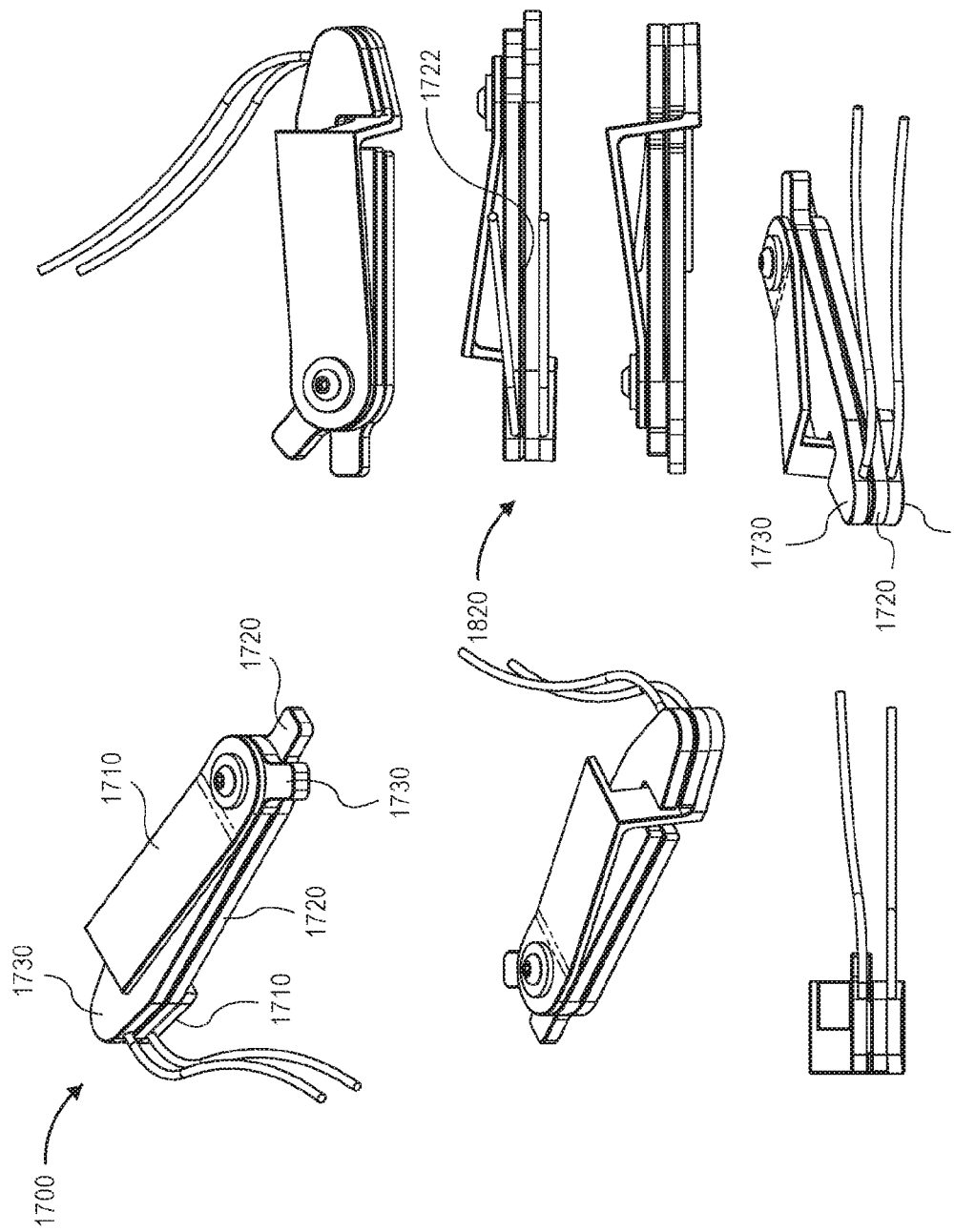

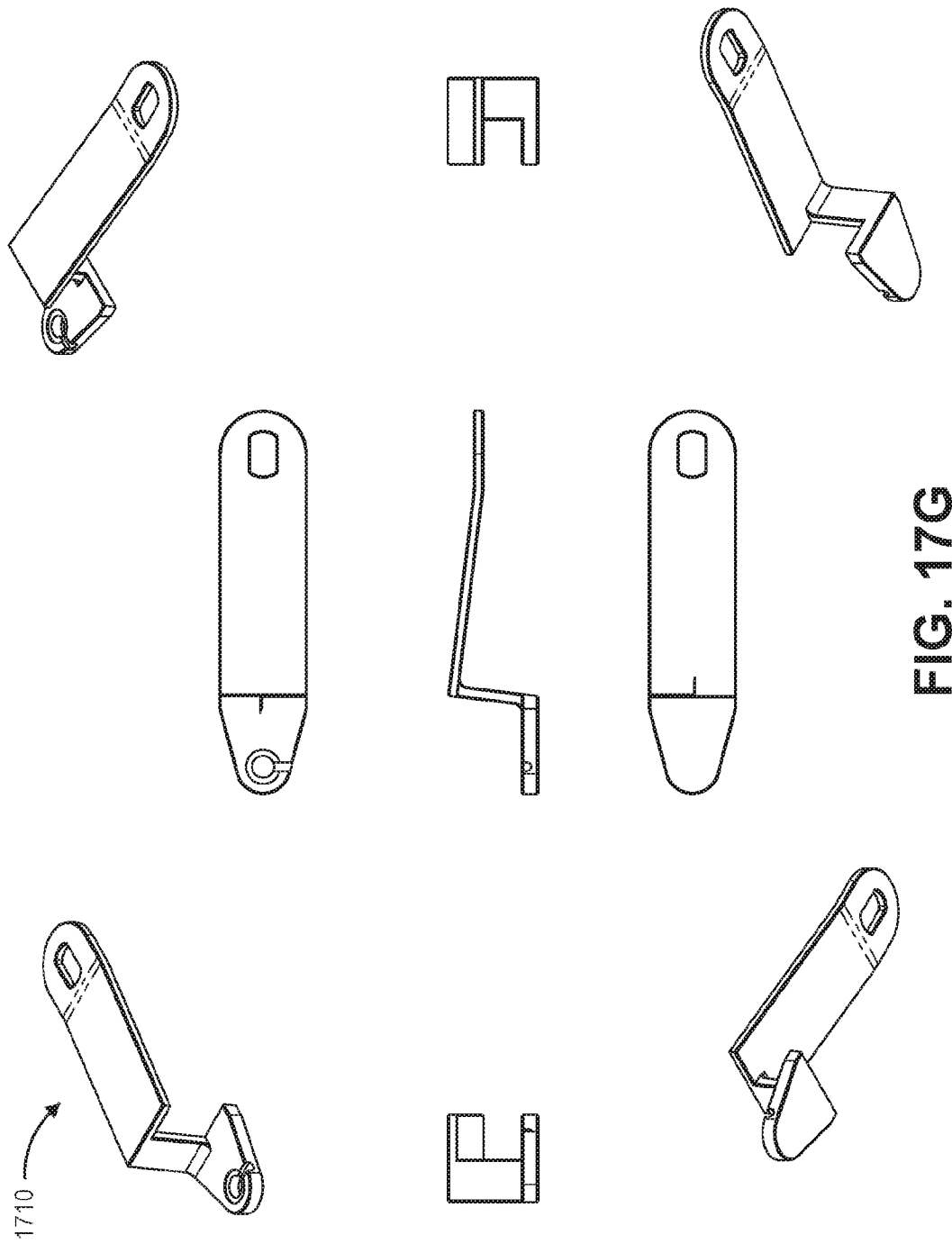

1820

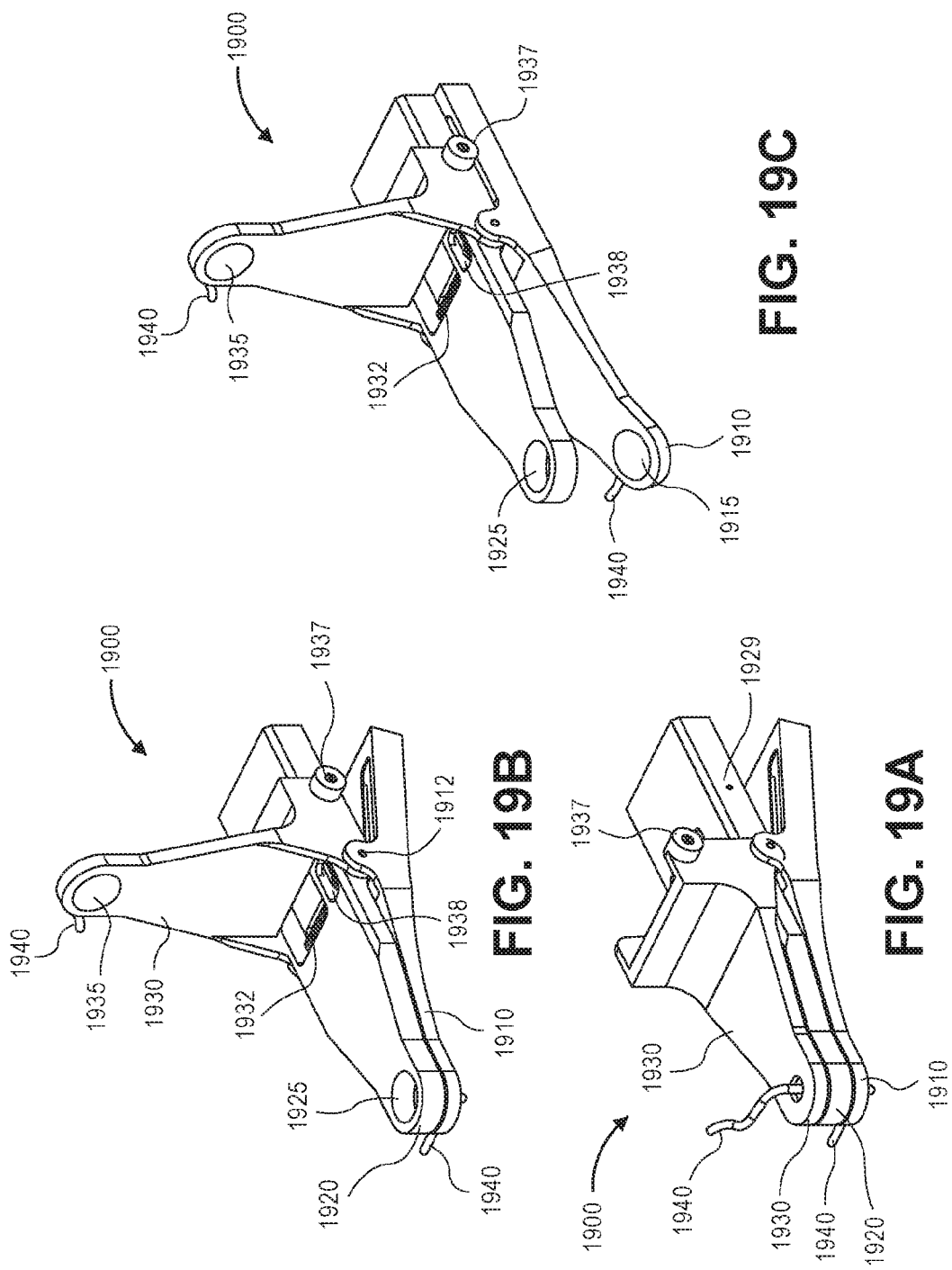

PULSE APPLICATOR

CROSS REFERENCE TO RELATED APPLICATIONS

This application claims priority to U.S. provisional patent application No. 62/337,270, titled "PULSE APPLICATOR," filed on May 16, 2015, which is hereby incorporated by reference in their entirety for all purposes.

BACKGROUND

1. Field of the Invention

The present application generally relates to electrical pulse techniques including circuits and systems for generating electric pulses, including the use of an energy-accumulating element discharged through a load by a relatively low voltage transistor and for controlling the discharge. Specifically, the pulse techniques are used for generating variable duration nanosecond pulsed electric fields (nsPEF) for electrotherapy.

2. Description of the Related Art

Surgical excision of a tumor can result in an infection and leave a scar. Furthermore, if there are more tumors, every cancerous tumor should be identified and individually excised by a surgeon. This can be time consuming and expensive, not to mention uncomfortable for patient or experiment subjects.

Cancerous tumors that are internal to a patient or experiment subject may be especially difficult to remove, let alone detect and treat. Many patient or experiment subjects' lives are turned upside down by the discovery of cancer in their bodies, sometimes which have formed relatively large tumors before being detected.

A "nanosecond pulsed electric field," sometimes abbreviated as nsPEF, includes an electric field with a sub-microsecond pulse width of between 0.1 nanoseconds (ns) and 1000 nanoseconds, or as otherwise known in the art. It is sometimes referred to as sub-microsecond pulsed electric field. NsPEFs often have high peak voltages, such as 10 kilovolts per centimeter (kV/cm), 20 kV/cm, to 500 kV/cm. Treatment of biological cells with nsPEF technology often uses a multitude of periodic pulses at a frequency ranging from 0.1 per second (Hz) to 10,000 Hz.

NsPEFs have been found to trigger apoptosis in cancerous tumors. Selective treatment of such tumors with nsPEFs can induce apoptosis within the tumor cells without substantially affecting normal cells in the surrounding tissue due to its non-thermal nature.

An example of nsPEF applied to biological cells is shown and described in U.S. Pat. No. 6,326,177 (to Schoenbach et al.), which is incorporated herein by reference in its entirety for all purposes.

The use of nsPEF for the treatment of tumors is a relatively new field. There exists a need for a device with better control over electrical characteristics for safe and effective studies and treatments of cancer in human subjects.

BRIEF SUMMARY

Generally, a nanosecond pulsed electrice field (nsPEF) generator is disclosed that delivers a nsPEF field to a patient or experiment subject.

Another inventive aspect is a pulse applicator. The pulse applicator includes a first arm, including a first electrode, a second arm, including a second electrode, and a spacer. The first arm, the spacer, and the second arm are movably connected, and define a gap between the first arm and the second arm. The first electrode, the gap, and the second electrode are selectively alignable, and the first electrode and the second electrode are configured to deliver an electrical field across the gap in response to an electrical pulse received across the first and second electrodes.

In some embodiments, each of the first and second arms are independently movable with respect to the spacer.

In some embodiments, the first arm and the spacer are movably connected so that the first electrode of the first arm may be selectively positioned adjacent to the gap, and where the second arm and the spacer are movably connected so that the second electrode of the second arm may be selectively positioned adjacent to the gap.

In some embodiments, while the first electrode of the first arm is adjacent to the gap and the second electrode of the second arm is adjacent to the gap, the first arm, the second arm, and the spacer collectively bound the gap.

In some embodiments, the spacer includes a cavity bounding the gap.

In some embodiments, while the second arm is spaced apart from the gap, the cavity is exposed so as to be viewable.

In some embodiments, the pulse applicator further includes a first actuator configured to move the first arm with respect to the spacer, and a second actuator configured to move the second arm with respect to the spacer.

In some embodiments, the second actuator has an over center design.

In some embodiments, the second actuator causes a linear and a rotational movement of the second arm.

In some embodiments, the first arm, the spacer, and the second are assembleable and disassembleable by hand, without any tools.

In some embodiments, while the first electrode of the first arm is adjacent to the gap and the second electrode of the second arm is adjacent to the gap, the first and second electrodes are spaced apart by a predetermined distance so that the electric field has a magnitude equal to the voltage applied across the first and second electrodes divided by the predetermined distance.

In some embodiments, the first and second electrodes are configured to deliver the electrical field across the gap for a duration of less than 1 ns.

Another inventive aspect is a method of using a pulse applicator. The pulse applicator includes a first arm having a first electrode, a second arm having a second electrode, and a spacer, where the first arm, the spacer, and the second arm are movably connected and define a gap between the first arm and the second arm. The method includes moving the first electrode of the first arm with respect to the gap to expose a first side of the gap, moving the second electrode of the second arm with respect to the gap to expose a second side of the gap, and, while the tumor and the second side of the gap are exposed, inserting a tumor of a subject into the gap. The method also includes, while the tumor and the second side of the gap are exposed, moving the first electrode of the first arm with respect to the gap to hold the tumor within the gap, and moving the second electrode of the second arm with respect to the gap to align the tumor between the first and second electrodes.

In some embodiments, moving the first electrode with respect to the gap includes increasing a space between the first electrode and the gap.

In some embodiments, exposing the second side of the gap causes the gap to be observable by a user.

In some embodiments, moving the first electrode of the first arm with respect to the gap causes tissue connecting the tumor to the subject to be between the first arm and the spacer.

In some embodiments, moving the second electrode of the second arm with respect to the gap occludes the gap.

In some embodiments, the method further includes delivering an electrical field across the gap in response to an electrical pulse received across the first and second electrodes.

In some embodiments, while the first electrode of the first arm is adjacent to the gap and the second electrode of the second arm is adjacent to the gap, the first and second electrodes are spaced apart by a predetermined distance so that the electric field has a magnitude equal to the voltage applied across the first and second electrodes divided by the predetermined distance.

In some embodiments, the first and second electrodes are configured to deliver the electrical field across the gap for a duration of less than 1 ns.

In some embodiments, the method further includes moving the first electrode of the first arm with respect to the gap to expose the tumor, and removing the tumor from the gap.

In some embodiments, moving the first electrode with respect to the gap includes applying a force to a first actuator, and moving the second electrode with respect to the gap includes applying a force to a second actuator.

In some embodiments, moving the second electrode with respect to the gap causes a linear and a rotational movement of the second electrode.

In some embodiments, the method further includes disassembling the pulse applicator by hand without any tools.

In some embodiments, the spacer includes a cavity defining the gap.

Another inventive aspect is a method of using a pulse applicator, the pulse applicator including a first arm having a first electrode, a second arm having a second electrode, and a spacer, where the first arm, the spacer, and the second arm are movably connected and define a gap between the first arm and the second arm. The method includes moving the second arm from a position occluding the first electrode to a position not occluding the first electrode, compressing tissue connecting a tumor to a subject between the spacer and the first arm, whereby the tumor is positioned in the gap, and moving the second electrode of the second arm with respect to the gap to a position adjacent the tumor.

In some embodiments, once the second arm is in the position not occluding the first electrode, the first electrode is observable by a user.

In some embodiments, moving the second electrode of the second arm to the position adjacent the tumor occludes the gap.

In some embodiments, the method further includes delivering an electrical field across the gap in response to an electrical pulse received across the first and second electrodes, where, while delivering the electric field across the gap, the first and second electrodes are spaced apart by a predetermined distance so that the electric field has a magnitude equal to the voltage applied across the first and second electrodes divided by the predetermined distance.

In some embodiments, the first and second electrodes are configured to deliver the electrical field across the gap for a duration of less than 1 ns.

In some embodiments, the spacer includes a cavity defining the gap.

BRIEF DESCRIPTION OF THE DRAWINGS

FIGS. 17A-17H are schematic illustrations of various views of an nsPEF pulse applicator which may be used in the nsPEF treatment system of FIG. 15.

FIG. 19A-19F are schematic illustrations of various views of an nsPEF pulse applicator which may be used in the nsPEF treatment system of FIG. 15.

DETAILED DESCRIPTION

It has been shown that nsPEF treatments can be used to cause cancerous tumor cells to undergo apoptosis, a programmed cell death. Tests have shown that tumors can shrink to nonexistence after treatment. No drugs may be necessary. It has also been shown that the subject's immune system may be stimulated to attack all similar tumor cells, including those of tumors that are not within the nsPEF-treated tumor.

A "tumor" includes any neoplasm or abnormal, unwanted growth of tissue on or within a subject, or as otherwise known in the art. A tumor can include a collection of one or more cells exhibiting abnormal growth. There are many types of tumors. A malignant tumor is cancerous, a pre-malignant tumor is precancerous, and a benign tumor is noncancerous. Examples of tumors include a benign prostatic hyperplasia (BPH), uterine fibroid, pancreatic carcinoma, liver carcinoma, kidney carcinoma, colon carcinoma, pre-basal cell carcinoma, and tissue associated with Barrett's esophagus.

A "disease" includes any abnormal condition in or on a subject that is associated with abnormal, uncontrolled growths of tissue, including those that are cancerous, pre-cancerous, and benign, or other diseases as known in the art.

"Apoptosis" of a tumor or cell includes an orderly, programmed cell death, or as otherwise known in the art.

"Immunogenic apoptosis" of a tumor or cell includes a programmed cell death that is followed by an immune system response, or as otherwise known in the art. The immune system response is thought to be engaged when the apoptotic cells express calreticulin or another antigen on their surfaces, which stimulates dendritic cells to engulf, consume, or otherwise commit phagocytosis of the targeted cells leading to the consequent activation of a specific T cell response against the target tumor or cell.

Pulse lengths of between 10 and 900 nanoseconds for nsPEF have been particularly studied to be effective in stimulating an immune response. Pulse lengths of about 100 nanoseconds are of particular interest in that they are long enough to carry sufficient energy to be effective at low pulse numbers but short enough to be effective in the manner desired.

A time of "about" a certain number of nanoseconds includes times within a tolerance of ±1%, 2%, 3%, 4%, 5%, 7.5%, 10%, 15%, 20%, 25% or other percentages, or fixed tolerances, such as ±0.1, ±0.2, ±0.3, ±0.4, ±0.5, ±0.7, ±1.0, ±2.0, ±3.0, ±4.0±5.0, ±7.0, ±10, ±15, ±20, ±25, ±30, ±40, ±50, ±75 ns, or other tolerances as acceptable in the art in conformance with the effectivity of the time period.

Immune system biomarkers can be measured before and/or after nsPEF treatment in order to confirm that the immune response has been triggered in a patient or experiment subject. Further, nsPEF treatment can be paired with a CD47-blocking antibody treatment to better train CD8+T cells (i.e., cytotoxic T cells) for attacking the cancer.

Figure 1:
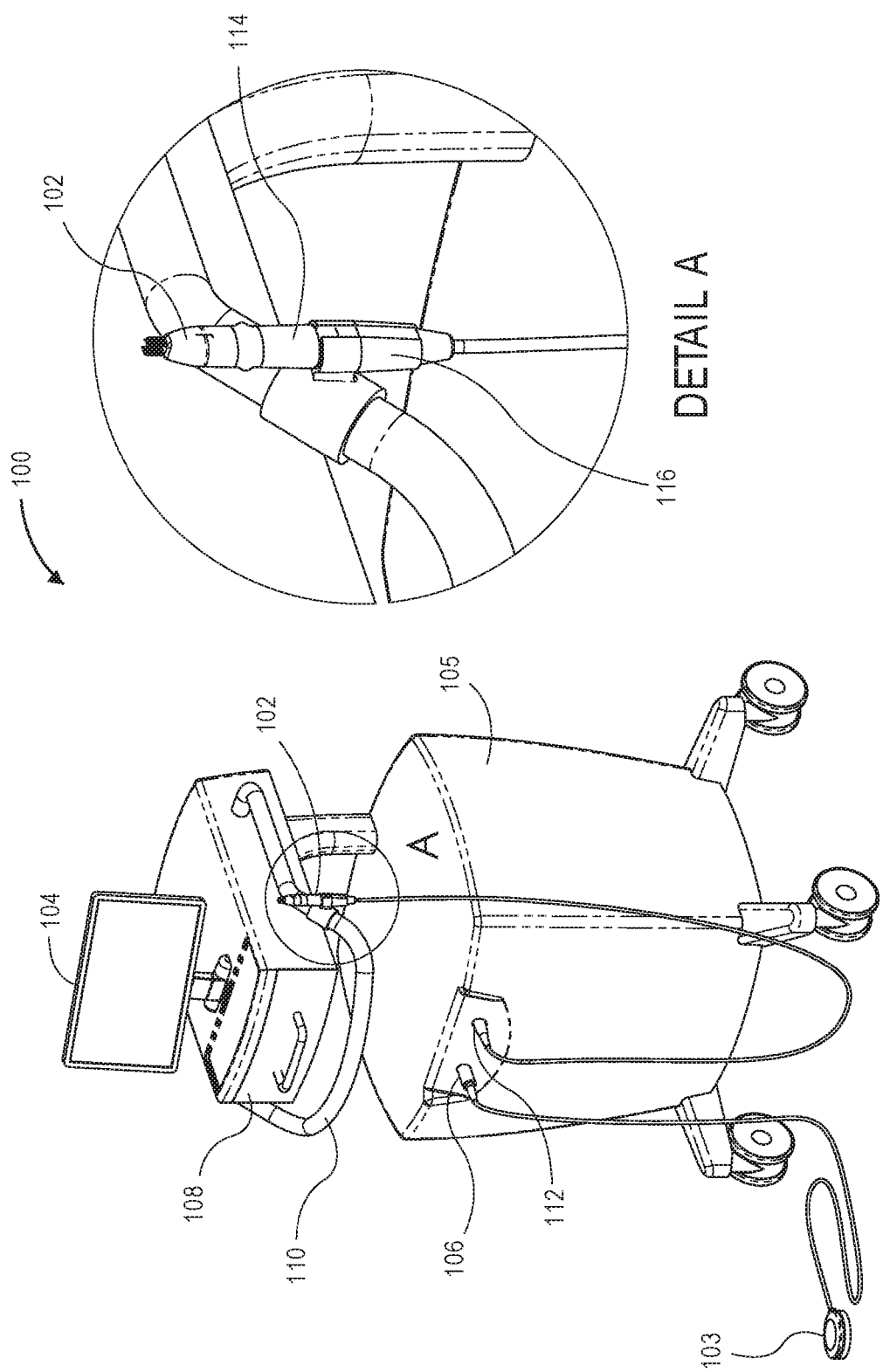
FIG. 1 illustrates a nanosecond pulse generator apparatus in accordance with an embodiment.

FIG. 1 illustrates a nanosecond pulse generator system in accordance with an embodiment. NsPEF system 100 includes nsPEF pulse applicator 102, footswitch 103, and interface 104. Footswitch 103 is connected to housing 105 and the electronic components therein through connector 106. NsPEF pulse applicator 102 is connected to housing 105 and the electronic components therein through high voltage connector 112. NsPEF system 100 also includes a handle 110 and storage drawer 108. As shown in DETAIL A portion of FIG. 1, nsPEF system 100 also includes holster 116, which is configured to hold nsPEF pulse applicator 102 at its handle portion 114.

A human operator inputs a number of pulses, amplitude, pulse duration, and frequency information, for example, into a numeric keypad or a touch screen of interface 104. In some embodiments, the pulse width can be varied. A microcontroller sends signals to pulse control elements within nsPEF system 100. In some embodiments, fiber optic cables allow control signaling while also electrically isolating the contents of the metal cabinet with nsPEF generation system 100, the high voltage circuit, from the outside. In order to further isolate the system, system 100 may be battery powered instead of from a wall outlet.

Figure 2:
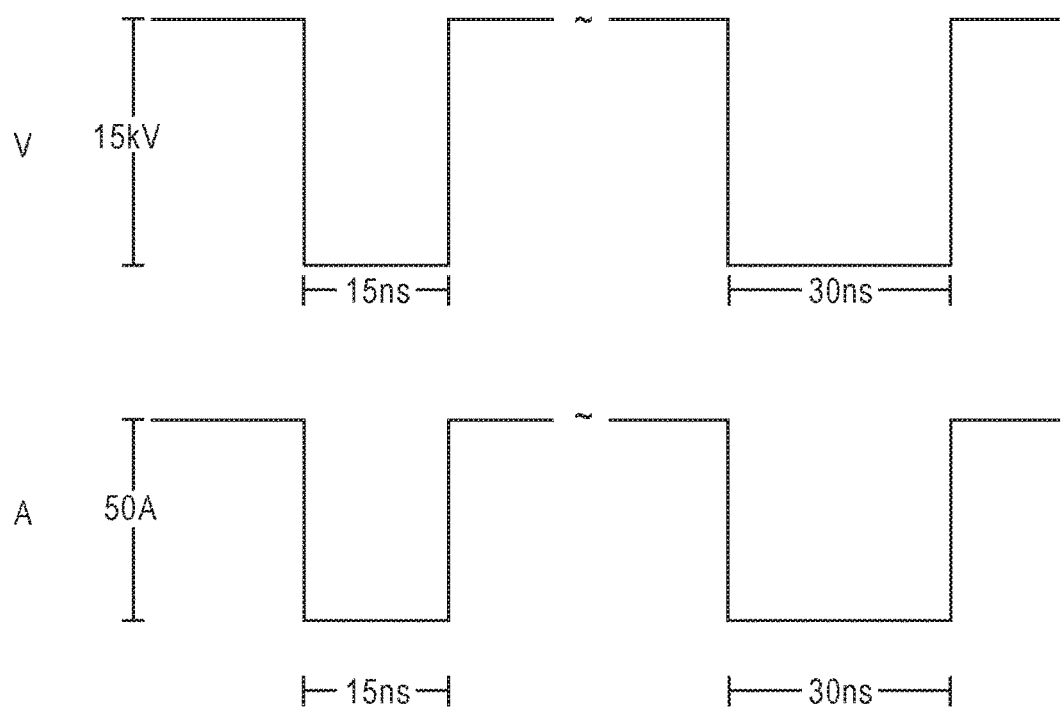
FIG. 2 illustrates a pulse profile for both voltage and current in accordance with an embodiment.

FIG. 2 illustrates a pulse profile for both voltage and current in accordance with an embodiment. Output from the nsPEF system 100 with voltage on the top of the figure and current on the bottom for a first and second pulses. The first pulse has an amplitude of about 15 kV, a current of about 50 A, and a duration of about 15 ns. The second pulse has an amplitude of about 15 kV, a current of about 50 A, and a duration of about 30 ns. If such a pulse had been delivered on suction nsPEF pulse applicators having 4 mm between the plates, the pulse generator would have delivered a pulse of about 50 A and 37.5 kV/cm. Given a voltage, current depends heavily on the nsPEF pulse applicator type and tissue resistance.

While FIG. 2 illustrates a specific example, other pulse profiles may also be generated. For example, in some embodiments, rise and/or fall times for pulses may be less than 20 ns, about 20 ns, about 25 ns, about 30 ns, about 40 ns, about 50 ns, about 60 ns, about 75 ns, or greater than 75 ns. In some embodiments, the pulse voltage may be less than 5 kV, about 5 kV, about 10 kV, about 15 kV, about 20 kV, about 25 kV, about 30 kV, or greater than 30 kV. In some embodiments, the current may be less than 10 A, about 10 A, about 25 A, about 40 A, about 50 A, about 60 A, about 75 A, about 100 A, about 125 A, about 150 A, about 175 A, about 200 A, or more than 200 A. In some embodiments, the pulse duration may be less than 10 ns, about 10 ns, about 15 ns, about 20 ns, about 25 ns, about 30 ns, about 40 ns, about 50 ns, about 60 ns, about 75 ns, about 100 ns, about 125 ns, about 150 ns, about 175 ns, about 200 ns, about 300 ns, about 400 ns, about 500 ns, about 750 ns, about 1 μs, about 2 μs, about 3 μs, about 4 μs, about 5 μs, or greater than 5 μs.

Figure 3:
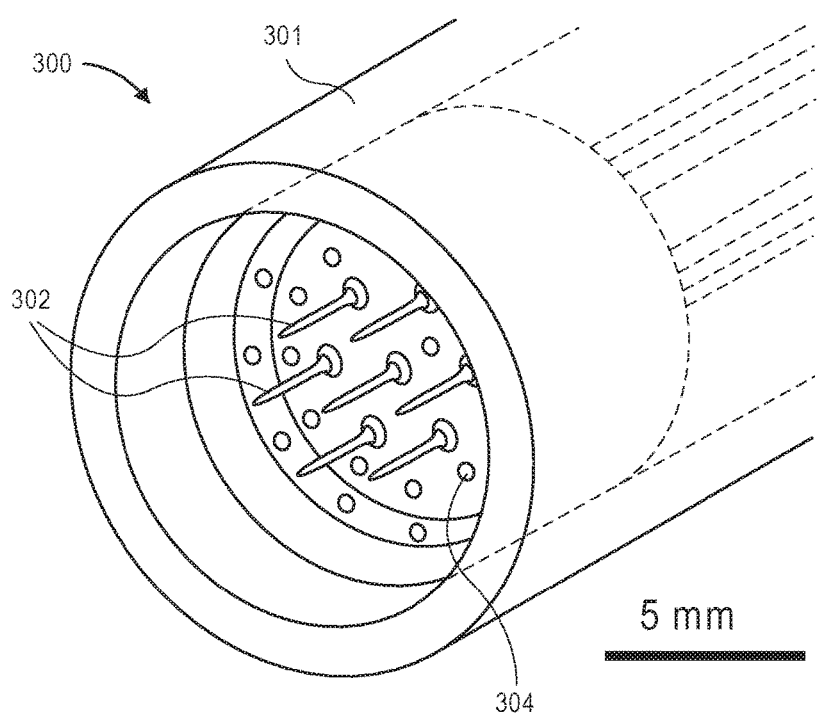
FIG. 3 illustrates a perspective view of a seven-needle nsPEF pulse applicator in accordance with an embodiment.

FIG. 3 illustrates a perspective view of a seven-needle suction nsPEF pulse applicator in accordance with an embodiment. In nsPEF pulse applicator 300, sheath 301 surrounds seven sharp electrodes 302 with an broad opening at a distal end. When the open end is placed against a tumor, air is evacuated from the resulting chamber through vacuum holes 304 to draw the entire tumor or a portion thereof into the chamber. The tumor is drawn so that one or more of the electrodes preferably penetrates the tumor. Sharp ends of the electrodes are configured to pierce the tumor. The center electrode may be at one polarity, and the outer six electrodes may be at the opposite polarity. Nanopulses electric fields can then be precisely applied to the tumor using nsPEF system 100 (see FIG. 1).

The electrodes can be apposed, one of each positive and negative pair of electrodes on one side of a tumor and the other electrode of the pair on an opposing side of the tumor. Opposing sides of a tumor can include areas outside or within a tumor, such as if a needle electrode pierces a portion of the tumor.

Figure 4:
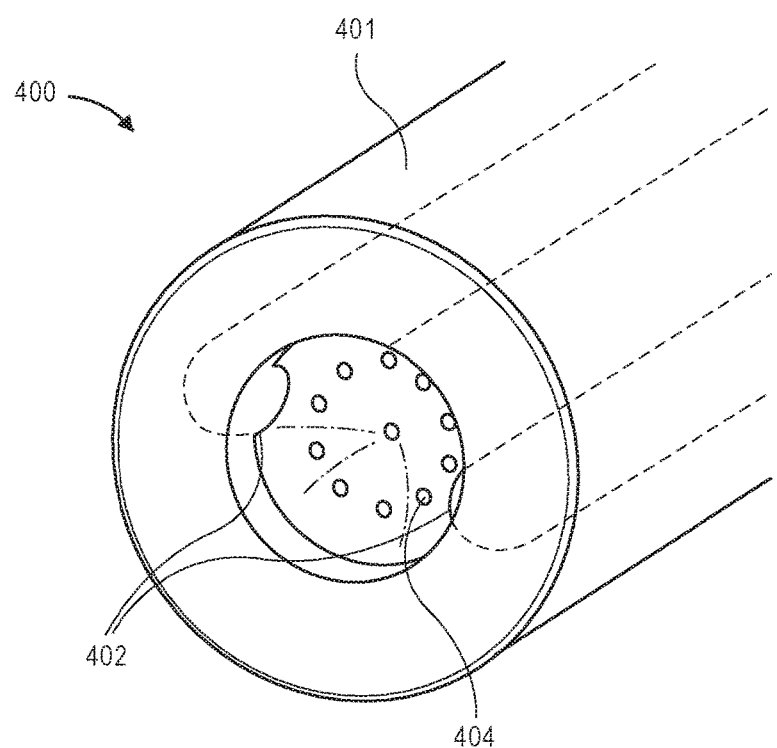
FIG. 4 illustrates a perspective view of a two-pole nsPEF pulse applicator in accordance with an embodiment.

FIG. 4 illustrates a two-pole suction nsPEF pulse applicator 400 in accordance with an embodiment. In nsPEF pulse applicator 400, sheath 401 surrounds two broad electrodes 402 on opposite sides of a chamber. When air is evacuated through vacuum holes 404 and a tumor is pulled within the chamber, the opposing electrodes apply nsPEF pulses to the tumor.

The nature of the nsPEF pulse applicator used mainly depends upon the shape of the tumor. Its physical size and stiffness can also be taken into account in selection of a particular nsPEF pulse applicator type.

U.S. Pat. No. 8,688,227 B2 (to Nuccitelli et al.) discloses other suction nsPEF pulse applicator-based medical instruments and systems for therapeutic electrotherapy, and it is hereby incorporated by reference.

If there are multiple tumors in a subject, a surgeon can select a single tumor to treat based on the tumor's compatibility with nsPEF pulse applicators. For example, a tumor that is adjacent to a stomach wall may be more easily accessible than one adjacent a spine or the brain. Because a nsPEF pulse is preferably applied so that the electric field transits through as much tumor mass as possible while minimizing the mass of non-tumor cells that are affected, a clear path to two opposed 'poles' of a tumor may also be a selection criterion.

For tumors on or just underneath the skin of subject, needle electrodes can be used percutaneously. For locations deeper within a subject, a retractable electrode can fit into a gastroscope, bronchoscope, colonoscope, or other endoscope or laparoscope. For example, a tumor in a patient or experiment subject's colon can be accessed and treated using an nsPEF pulse applicator within a colonoscope.

Barrett's esophagus, in which portions of tissue lining a patient or experiment subject's esophagus are damaged, may be treated using an nsPEF pulse applicator placed on an inflatable balloon.

Embodiments of nanosecond pulsed power generators produce electric pulses in the range of single nanoseconds to single microseconds. The pulses are created by rapid release of energy stored in, for example, a capacitive or inductive energy reservoir to a load in a period that is generally much shorter than the charging time of the energy reservoir.

Conventional capacitive-type pulsed generators include pulse forming networks, which provide fixed pulse duration and impedance. With prior knowledge of a load's resistance, a pulse forming network with impedance that matches the load can be used. But for broader applications, especially when the load resistance is unknown, it is desirable to have a pulse generator with a flexibility of impedance matching and variation of pulse duration. Such flexibility can be implemented by switching a capacitor with a controllable switch. In this case, the capacitor can be regarded as a "voltage source" and can adapt to various load resistance. The switched pulse amplitude can then have the same voltage as the voltage of the capacitor. The pulse width is accordingly determined by the switch "on" time.

The selection of switches in nanosecond pulse generators is limited because of the high voltages, high currents, and fast switching times involved.

Spark gap switches, typically used in pulsed power technology, are capable of switching high voltages and conducting high currents. But they can only be turned on, and stopping the current flow in the middle of conduction is impossible. Besides spark gaps, other types of high voltage, high power switches are available, such as: magnetic switches, vacuum switches (Thyratrons for example), and certain high-voltage semiconductor switches.

Magnetic switches, relying on the saturation of magnetic core, change from high impedance to low impedance in the circuit. They can be turned on above a certain current threshold but will not be turned off until all the current is depleted by the load.

Vacuum switches are a good option for high voltage and high repletion rate operation, but similar to magnetic switches, they also can be only turned on, but cannot be turned off at a predetermined time.

Some types of high-voltage semi-conductor switches may also be considered. Thyristors and insulated gate bipolar transistors (IGBTs) may, in some embodiments be used. However, the turn-on times of Thyristors and IGBTs limit their usefulness.

Metal-oxide-semiconductor field-effect transistors (MOSFETs) have insufficient maximum drain to source voltage ratings (e.g. <1 kV) and insufficient maximum drain to source current ratings (e.g. <50 A) to be used in conventional pulse generator architectures to produce the voltage and current necessary for the applications discussed herein. If they were used, a large number of stages would be needed in order to produce high-amplitude output voltages. However, in conventional Marx generator architectures with a large number of stages, the Marx generator goes into an underdamped mode instead of a critically damped mode, resulting in loss in overshoot. As a result, the overall voltage efficiency decreases. For example, a voltage efficiency of a Marx generator may be 80% at 5 stages but decrease to 50% at 20 stages.

Furthermore, as the number of stages is increased, the impedance of the Marx generator also increases. This reduces the total energy deliverable to the load. This is particularly unfavorable for driving low impedance loads and long pulses.

In addition, the charging losses in the charging resistors also increases with the increased number of stages. As a result, such Marx generators are unsuitable for high repetition rate operation.

Therefore, in order to produce high voltage pulses, simply increasing the number of stages will cause a series of problems, including low efficiency, high impedance, etc. Because there is a tradeoff between the number of the stages and the actual output voltage, using conventional Marx generators cannot produce high voltage pulses which are sufficient for the applications discussed herein.

Some embodiments of this disclosure include a tunable, high voltage, nanosecond pulse generator. The switches may be power MOSFETs, which may, for example, be rated for a voltage of 1 kV and current of up to 30 A. In some embodiments, the switches power MOSFETs rated for a voltage of 1 kV and current of up to continuous 90 A and more than 200 A peak. Voltage is scaled up by a Marx-switch stack hybrid circuit. In each Marx generator stage, a particularly configured stack of MOSFETs is used. As a result, the charging voltage for each stage is greater than the rated maximum for a single switch.

A technical advantage of the configuration is that the overall output voltage can be increased with just a few stages (e.g. <=5). As a result, the problems discussed above with Marx generators having a large number of stages are avoided and high efficiency, low impedance, and large variability in the pulse duration can be achieved.

Such an architecture also allows much easier control as only one trigger circuit may be needed for each stage. One additional benefit is that the pulse generator has low impedance, so it will be able to drive various loads with high current and extended pulse duration. The scaling up of the current is implemented by combining multiple Marx-switch stack circuits in parallel. The pulse duration is controlled by the closing and opening of the switch stack switches.

Figure 5:
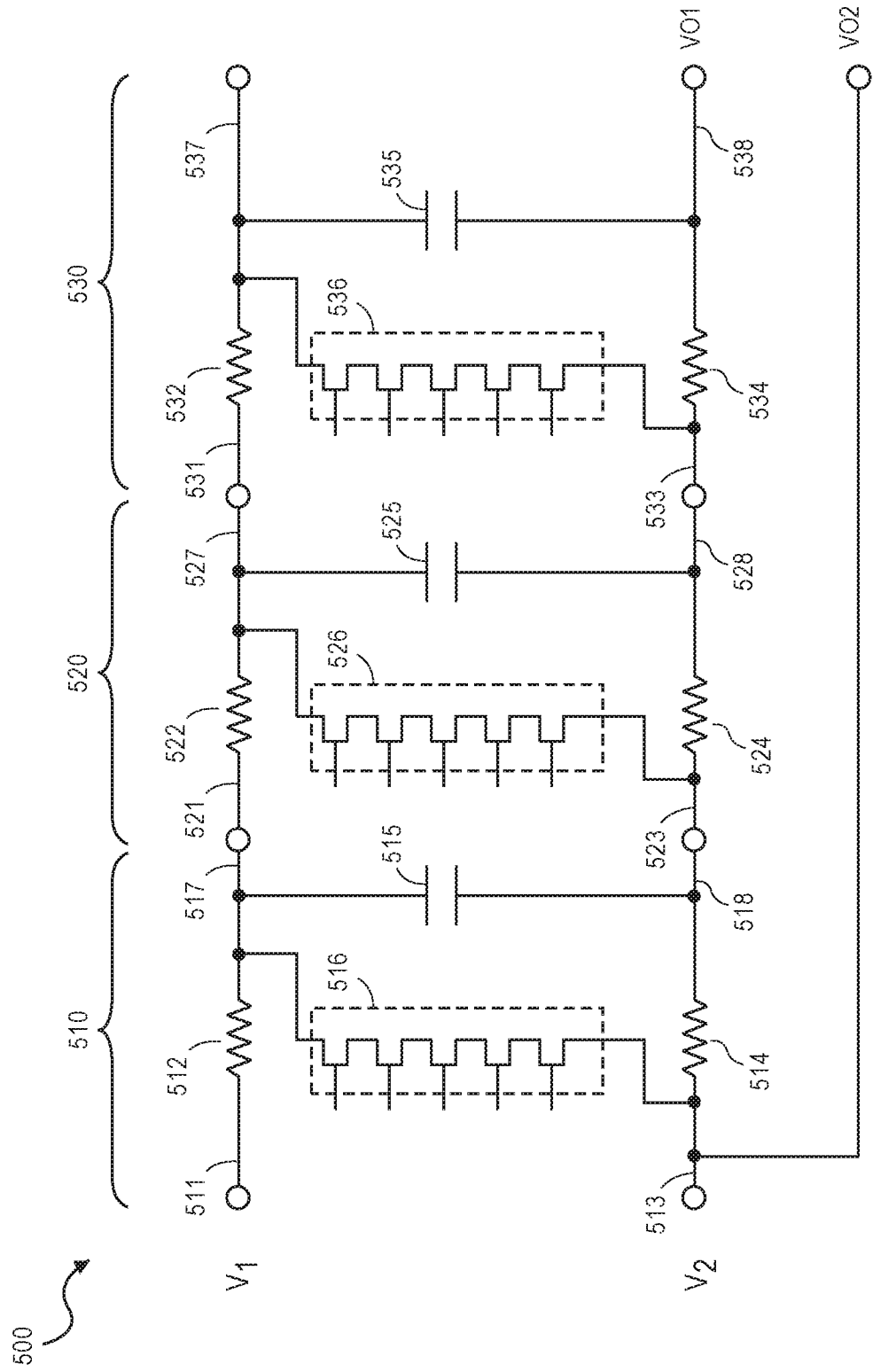
FIG. 5 is an electrical schematic of a pulse generator in accordance with an embodiment.

FIG. 5 illustrates a pulse generator circuit 500 which may be used inside nsPEF system 100 of FIG. 1. Pulse generator circuit 500 illustrates a panel comprising a Marx generator switched by three switch stacks. The nsPEF system can have a single pulse generator circuit panel. In some embodiments, a nsPEF system includes multiple panels in parallel.

Circuit 500 includes three stages—510, 520, and 530. In some embodiments, another number of stages is used. For example, in some embodiments, 2, 4, 5, 6, 7, 8, 9, or 10 stages are used. Stage 510 includes resistors 512 and 514, capacitor 515, and switch stack 516. Likewise, stage 520 includes resistors 522 and 524, capacitor 525, and switch stack 526, and stage 530 includes resistors 532 and 534, capacitor 535, and switch stack 536. Each of these elements have structure and functionality which is similar to the corresponding elements of stage 510.

Stage 510 has first and second input voltage input terminals 511 and 513 and first and second voltage output terminals 517 and 518. Stage 520 has first and second input voltage input terminals 521 and 523, and first and second voltage output terminals 527 and 528. Stage 530 has first and second input voltage input terminals 531 and 533, and first and second voltage output terminals 537 and 538.

The first and second voltage input terminals 511 and 513 of stage 510 are respectively connected to first and second power supply input terminals V1 and V2. The first and second voltage output terminals 517 and 518 of stage 510 are respectively connected to the first and second voltage input terminals 521 and 523 of stage 520. The first and second voltage output terminals 527 and 528 of stage 520 are respectively connected to the first and second voltage input terminals 531 and 533 of stage 530. The second voltage output terminal 538 of stage 530 and second voltage input terminal 513 of stage 510 are respectively connected to first and second power output terminals VO1 and VO2.

Pulse generator circuit 500 operates in a charge mode, and in a discharge mode. During the charge mode, described below with reference to FIG. 6A in more detail, capacitors 515, 525, and 535 are charged by current received from the first and second power supply input terminals V1 and V2. During the discharge mode, described below with reference to FIG. 6B in more detail, capacitors 515, 525, and 535 are discharged to provide a current to a load (not shown) connected across first and second power output terminals VO1 and VO2.

Figure 6A:
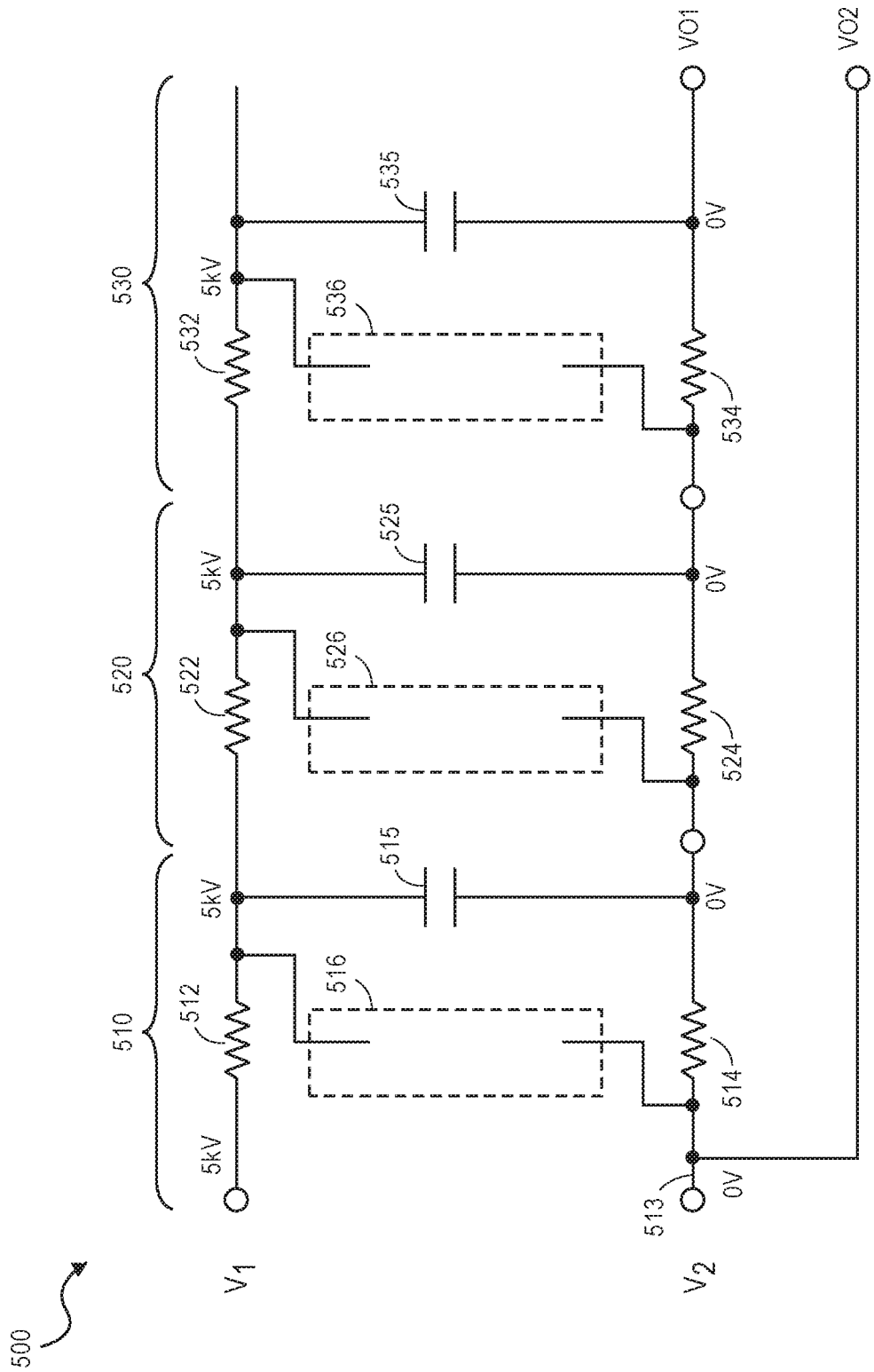
FIG. 6A is a schematic illustrating the pulse generator shown in FIG. 5 during charge mode.

FIG. 6A illustrates pulse generator circuit 500 during charge mode. First and second input voltages are respectively applied to first and second power supply input terminals V1 and V2 while each of switch stacks 516, 526, and 536 are nonconductive or open, and while first and second power output terminals may be disconnected from the load (not shown). Because each of switch stacks 516, 526, and 536 are open, substantially no current flows therethrough, and they are represented as open circuits in FIG. 6A. During the charge mode, each of capacitors 515, 525, and 535 are charged by current flowing through resistors 512, 522, 532, 534, 524, and 514 to or toward a voltage equal to the difference between the first and second input voltages.

Each of the switches of switch stacks 516, 526, and 536 has a breakdown voltage rating which should not be exceeded. However, because the switches are serially connected, the capacitors 515, 525, and 535 may be charged to a voltage significantly greater than the breakdown voltage of the individual switches. For example, the breakdown voltage of the switches may be 1 kV, and the capacitors 515, 525, and 535 may be charged to a voltage of 5 kV, when 5 or more switches are used in each switch stack.

For example, the first and second input voltages may respectively be 5 kV and 0V. In such an example, each of the capacitors 515, 525, and 535 is charged to or toward a voltage equal to 5 kV. In some embodiments, the difference between the first and second input voltages is limited to be less than 10 kV.

Figure 6B:
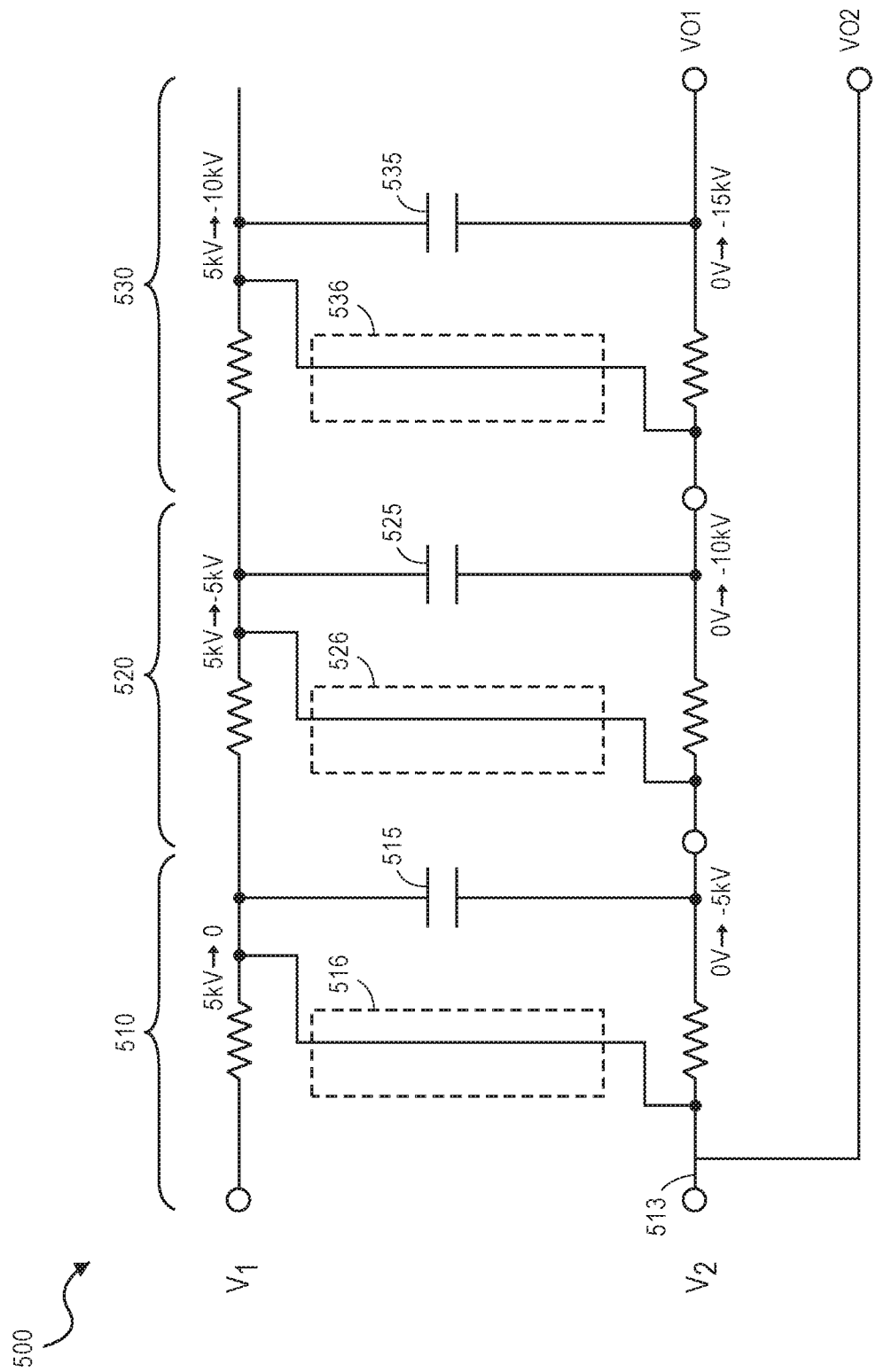
FIG. 6B is a schematic illustrating the pulse generator shown in FIG. 5 during discharge mode.

FIG. 6B illustrates pulse generator circuit 500 during discharge mode. First power supply input terminal V1 may be disconnected from the first input voltage. In some embodiments, first power supply input terminal V1 remains connected to the first input voltage. Second power supply input terminal V2 remains connected to the second input voltage. In addition, each of switch stacks 516, 526, and 536 are conductive or closed. Because each of switch stacks 516, 526, and 536 are closed, current flows therethrough, and they are represented as conductive wires in FIG. 6B. As a result, a low impedance electrical path from power supply input terminal V2 to power output terminal VO1 is formed by switch stack 516, capacitor 515, switch stack 526, capacitor 525, switch stack 536, and capacitor 535. Consequently, the difference between the voltages at the power output terminals VO1 and VO2 is equal to the number of stages (in this example, 3) times the difference between the first and second input voltages.

Where the first and second input voltages are respectively 5 kV and 0V, a voltage difference of 15 kV is developed across the power output terminals VO1 and VO2.

Figure 7:
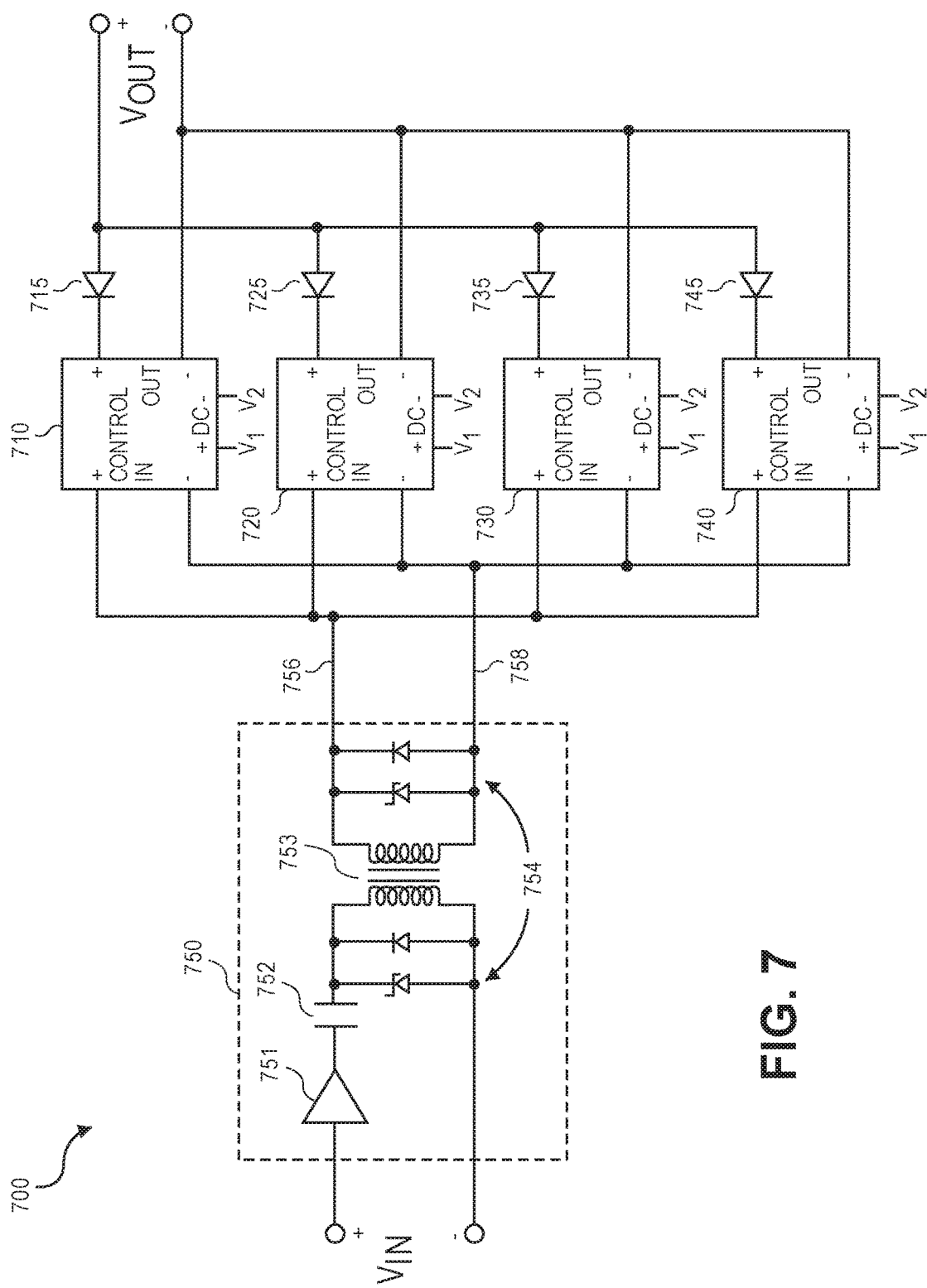
FIG. 7 is an electrical schematic of an assembly of pulse generator circuits.

FIG. 7 illustrates an alternative pulse generator circuit 700 which may be used inside nsPEF system 100 of FIG. 1. This pulse generator includes panels in parallel. The number of panels can be adjusted to allow the system to generate different amounts of current and power.

Pulse generator circuit 700 receives input pulses across input port Vin, and generates output pulses across output port Vout in response to the received input pulses.

Pulse generator circuit 700 includes multiple panels or pulse generator circuits 710, 720, 730, and 740. Pulse generator circuit 700 also includes driver 750. In this embodiment, four pulse generator circuits are used. In alternative embodiments, fewer or more pulse generator circuits are used. For example, in some embodiments, 2, 3, 5, 6, 7, 8, 9, 10 or another number of pulse generator circuits are used.

Each of the pulse generator circuits 710, 720, 730, and 740 may have characteristics similar to other pulse generator circuits discussed herein. For example, each the pulse generator circuits 710, 720, 730, and 740 may have characteristics similar to pulse generator circuit 500 discussed above with reference to FIGS. 5, 6A, and 6B.

Each of pulse generator circuits 710, 720, 730, and 740 has positive and negative DC input terminals, positive and negative control input terminals, and positive and negative output terminals, and is configured to generate output voltage pulses across the positive and negative output terminals in response to driving signal pulses applied across the positive and negative control input terminals. The output voltage pulses are also based on power voltages received across positive and negative DC power input terminals.

The driving signal pulses are generated across conductors 756 and 758 by driver 750, which includes amplifier circuit 751, capacitor 752, and transformer 753. In some embodiments, driver 750 also includes clamp circuits 754.

Driver 750 receives an input signal pulse at input port Vin and generates a driving signal pulse across conductors 756 and 758 in response to the input signal pulse. Amplifier circuit 751 receives the input signal pulse and drives transformer 753 through capacitor 752, which blocks low frequency and DC signals. In response to being driven by amplifier circuit 751, transformer 753 generates an output voltage pulse across conductors 756 and 758, such that the duration of the output voltage pulse is equal to or substantially equal (e.g. within 10% or 1%) to the duration of the input signal pulse at input port Vin.

In some embodiments, clamp circuits 754 are included at least to dampen potential signals, which may otherwise be caused by resonance. Clamp circuits 754 include parallel diodes, which provide a short-circuit path for any current reversal, and also clamp the maximum voltage across the components connected to the clamp circuits 754.

In some embodiments, transformer 753 has a 1:1 turns ratio. In alternative embodiments, a different turns ratio is used.

Each of pulse generator circuits 710, 720, 730, and 740 receives the voltage pulses from driver 750 across the positive and negative control input terminals and generates corresponding voltage pulses across the positive and negative output terminals in response to the received voltage pulses from driver 750. The voltage pulses generated across the positive and negative output terminals have durations which are equal to or substantially equal (e.g. within 10% or 1%) to the durations of the voltage pulses received from driver 750.

In this embodiment, the negative output terminals of pulse generator circuits 710, 720, 730, and 740 are directly connected to the negative Vout terminal of the output port Vout of pulse generator circuit 700. In addition, in this embodiment, the positive output terminals of pulse generator circuits 710, 720, 730, and 740 are respectively connected to the positive Vout terminal of the output port Vout of pulse generator circuit 700 through diodes 715, 725, 735, and 745. Diodes 715, 725, 735, and 745 decouple pulse generator circuits 710, 720, 730, and 740 from one another. As a consequence, interference and the associated pulse distortion that would otherwise occur is substantially eliminated. For example, diodes 715, 725, 735, and 745 prevent current from one of pulse generator circuits 710, 720, 730, and 740 to another of pulse generator circuits 710, 720, 730, and 740 if the switching is not perfectly synchronous. Diodes 715, 725, 735, and 745 also prevent current from flowing from the pulse generator circuits 710, 720, 730, and 740 while they are charging.

In this embodiment, diodes 715, 725, 735, and 745 each include a single diode. In alternative embodiments, diodes 715, 725, 735, and 745 each include multiple diodes connected serially based at least upon voltage ratings of the serially connected diodes.

In this embodiment, diodes 715, 725, 735, and 745 are connected so as to conduct current from the positive terminal of output port Vout toward pulse generator circuits 710, 720, 730, and 740, as pulse generator circuits 710, 720, 730, and 740 in this embodiment are configured to generate negative pulses. In alternative embodiments, where pulse generator circuits are configured to generate positive pulses, diodes may be similarly connected so as to conduct current from the pulse generator circuits to the positive terminal of the output port.

Figure 8:
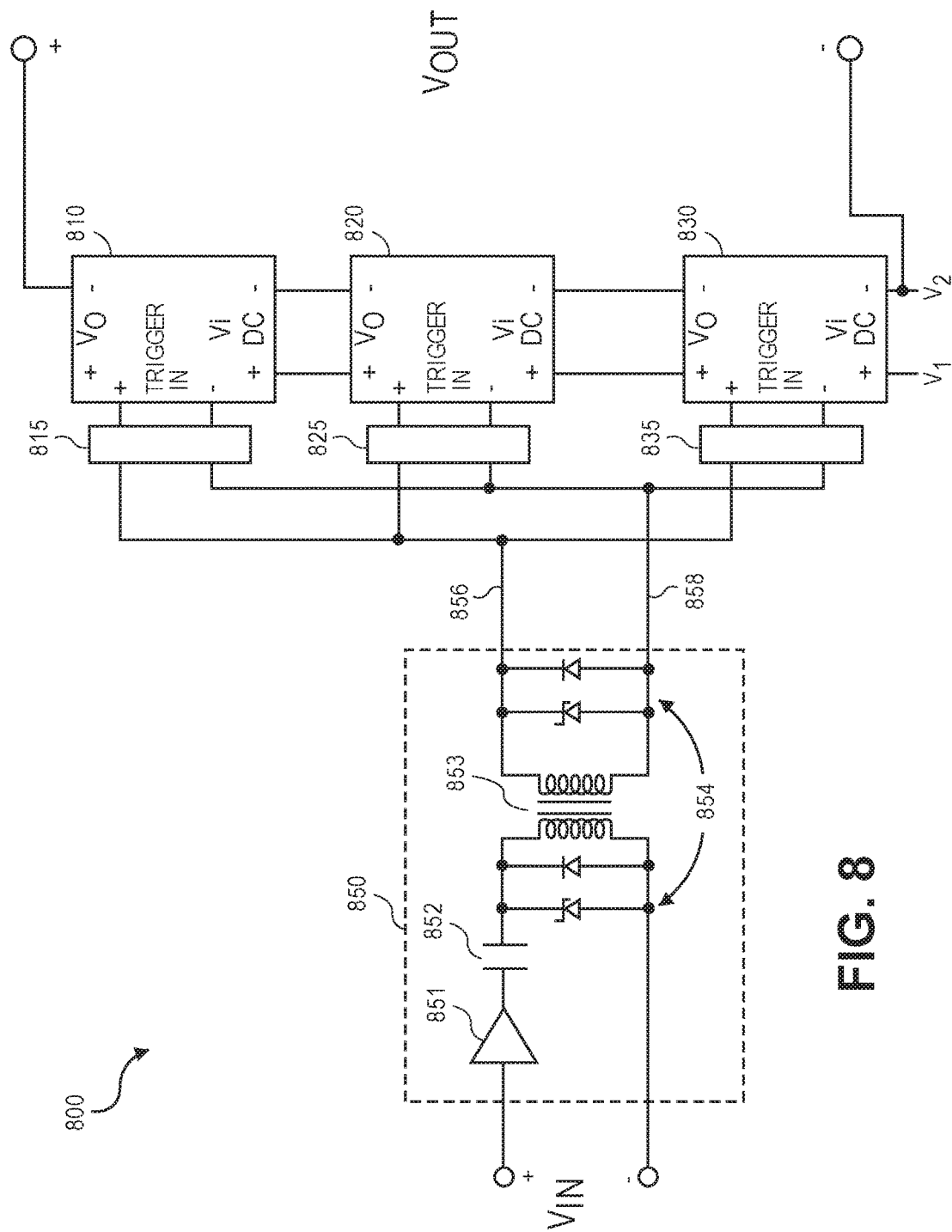
FIG. 8 is an electrical schematic of one of the pulse generator circuits shown in FIG. 7.

FIG. 8 illustrates a pulse generator circuit 800 which may be used for pulse generator circuits 710, 720, 730, and 740 of pulse generator circuit 700 of FIG. 7.

Pulse generator circuit 800 receives input pulses across input port Vin, and generates output pulses across output port Vout in response to the received input pulses.

Pulse generator circuit 800 includes multiple pulse generator stages 810, 820, and 830. In this embodiment, pulse generator circuit 700 also includes driver 850, and optional common mode chokes 815, 825, and 835.

Each of the pulse generator stages 810, 820, and 830 may have characteristics similar to other pulse generator stages discussed herein. For example, each the pulse generator stages 810, 820, and 830 may have characteristics similar to stages 510, 520, and 530 of pulse generator circuit 500 discussed above with reference to FIGS. 5, 6A, and 6B. In some embodiments, fewer or more pulse generator stages may be used.

Each of pulse generator stages 810, 820, and 830 has positive and negative trigger input terminals, power positive and negative DC input terminals, and positive and negative Vo output terminals, and is configured to generate output voltage pulses across the positive and negative Vo output terminals in response to driving signal pulses applied across the positive and negative trigger input terminals. The output voltage pulses are also based on power voltages V1 and V2 respectively received at power positive and negative DC input terminals.

In this embodiment, the negative Vi input terminal of pulse generator stage 830 is connected with the negative terminal of the output port Vout of pulse generator circuit 800. In addition, in this embodiment, the negative Vo output terminal of pulse generator stage 810 is connected with the positive terminal of the output port Vout of pulse generator circuit 800.

In addition, as shown, the positive Vo output terminal of pulse generator 830 is connected with the positive Vi input terminal of pulse generator 820, and the negative Vo output terminal of pulse generator 830 is connected with the negative Vi input terminal of pulse generator 820. Furthermore, the positive Vo output terminal of pulse generator 820 is connected with the positive Vi input terminal of pulse generator 810, and the negative Vo output terminal of pulse generator 820 is connected with the negative Vi input terminal of pulse generator 810.

The driving signal pulses for pulse generator stages 810, 820, and 830 are generated across conductors 856 and 858 by driver 850, which includes amplifier circuit 851, capacitor 852, and transformer 853. In some embodiments, driver 850 also includes clamp circuits 854.

Driver 850 receives an input signal pulse at input port Vin, which is connected to conductors 756 and 758, as shown in FIG. 7 discussed above. Driver 850 generates a driving signal pulse across conductors 856 and 858 in response to the input signal pulse. Amplifier circuit 851 receives the input signal pulse, and drives transformer 853 through capacitor 852, which reduces or blocks low frequency and DC signals. In response to being driven by amplifier circuit 851, transformer 853 generates an output voltage pulse across conductors 756 and 758, such that the duration of the output voltage pulse is equal to or substantially equal (e.g. within 10% or 1%) to the duration of the input signal pulse at input port Vin.

In some embodiments, clamp circuits 854 are included at least to dampen potential signals, which may otherwise be caused by resonance. Clamp circuits 854 include parallel diodes, which provide a short-circuit path for any current reversal, and also clamp the maximum voltage across the components connected to the clamp circuits 854.

In some embodiments, transformer 853 has a 1:1 turns ratio. In alternative embodiments, a different turns ratio is used.

Each of pulse generator stages 810, 820, and 830 receives the voltage pulses from driver 850 through a corresponding choke 815, 825, or 835, which blocks high frequency signals, for example, from coupling from the high voltage pulse generator stages 810, 820, and 830. The voltage pulses are received at the positive and negative trigger input terminals and the pulse generator stages 810, 820, and 830 each generate corresponding voltage pulses across the positive and negative Vo output terminals in response to the received voltage pulses from driver 850. The voltage pulses generated across the positive and negative Vo output terminals have durations which are equal to or substantially equal (e.g. within 10% or 1%) to the durations of the voltage pulses received from driver 850.

Figure 9:
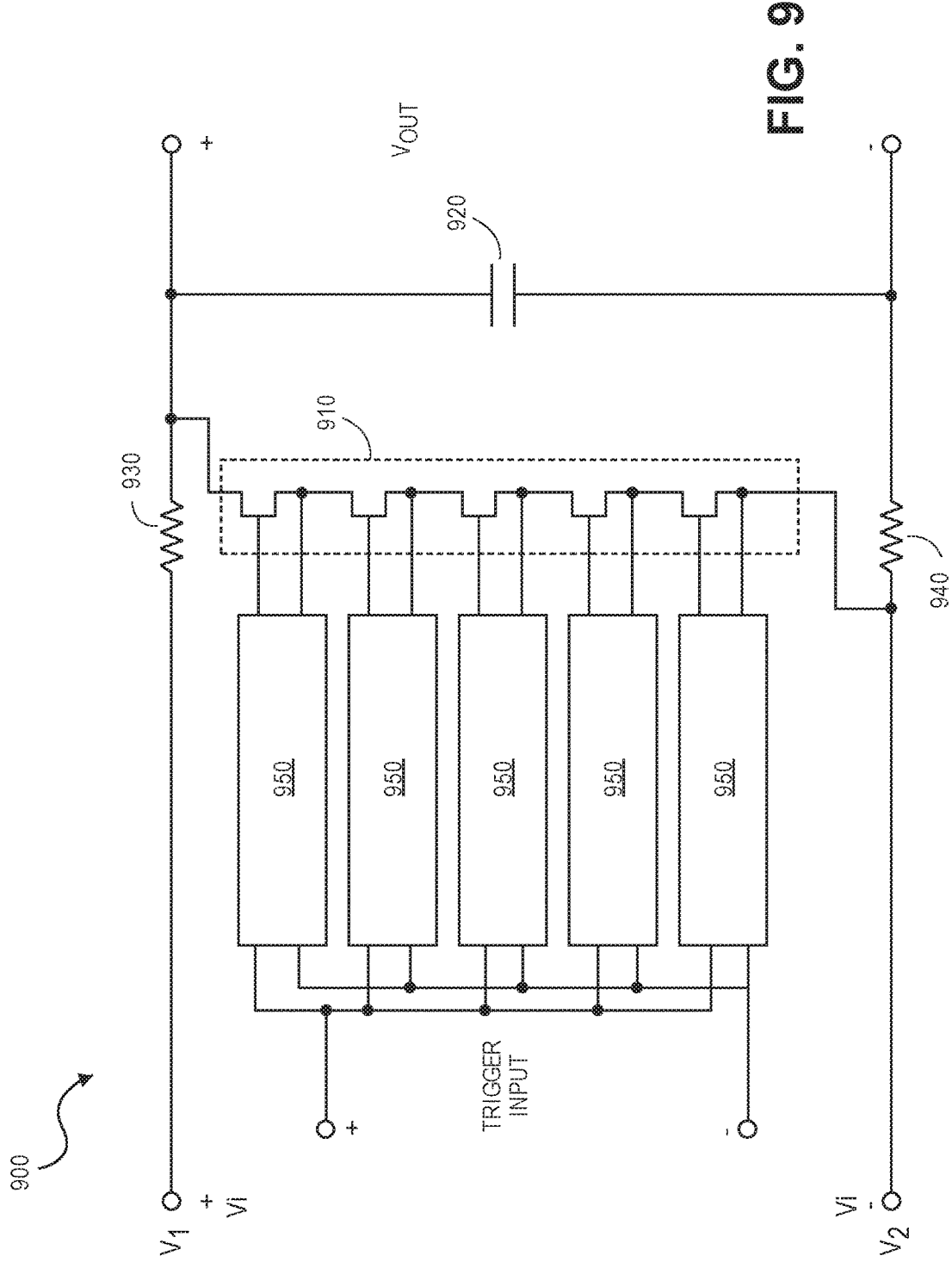
FIG. 9 is an electrical schematic of one of the pulse generator stages shown in FIG. 8.

FIG. 9 illustrates a pulse generator stage 900 which may be used as one of the pulse generator stages 810, 820, and 830 of pulse generator circuit 800 shown in FIG. 8.

Pulse generator stage 900 receives trigger pulses across input port trigger input, and generates output voltages at output port Vout in response to the received trigger pulses. The output voltages are also generated based on power voltages received at power input terminals V1 and V2. Pulse generator stage 900 includes multiple switch drivers 950.

Pulse generator stage 900 also includes switch stack 910, capacitor 920, and resistors 930 and 940.

Switch drivers 950 are configured to receive the trigger pulses, and to generate control signals for the switches of switch stack 910 in response to the received trigger pulses, as discussed in further detail below. Each of the control signals is referenced to a voltage specific to the switch being driven. Accordingly, a first switch receives a control signal pulse between first and second voltages, and a second switch receives a control signal pulse between third and fourth voltages, where each of the first, second, third, and fourth voltages are different. In some embodiments, the difference between the first and second voltages is substantially the same as the difference between the third and fourth voltages.

Switch stack 910, capacitor 920, and resistors 930 and 940 cooperatively function with corresponding elements in the other pulse generator stages of pulse generator circuit 800, discussed above with reference to FIG. 8, to generate the voltage pulses across the positive and negative Vo output terminals of pulse generator circuit 800. These elements may, for example, cooperatively function as the corresponding elements discussed above with reference to pulse generator circuit 500 shown in FIGS. 5, 6A, and 6B. For example, these elements may cooperate to generate the voltage pulses across the positive and negative Vo output terminals of pulse generator circuit 800 in response to the power voltages applied to power input terminals V1 and V2 and to the control signals applied to the switches of switch stack 910.

Because the control signals are generated in response to the input pulses received across input port Vin of pulse generator circuit 700 illustrated in FIG. 7 through multiple stages of driving, the control signals cause all of the switches of the switch stacks of pulse generator circuit 700 to be turned on and to be turned off substantially simultaneously. For example, a 15V input pulse having a duration of, for example 100 ns, received at input port Vin of pulse generator circuit 700 may cause the pulse generator circuit 700 to generate a high-voltage (e.g. ~15 kV) output pulse having a duration of about 100 ns. Similarly, a 15V input pulse having a duration of, for example 5 μs, received at input port Vin of pulse generator circuit 700 may cause the pulse generator circuit 700 to generate a high-voltage (e.g. ~15 kV) output pulse having a duration of about 5 μs. Accordingly, the duration of the high-voltage output pulse is substantially the same as a selected duration of an input pulse.

Figure 10:
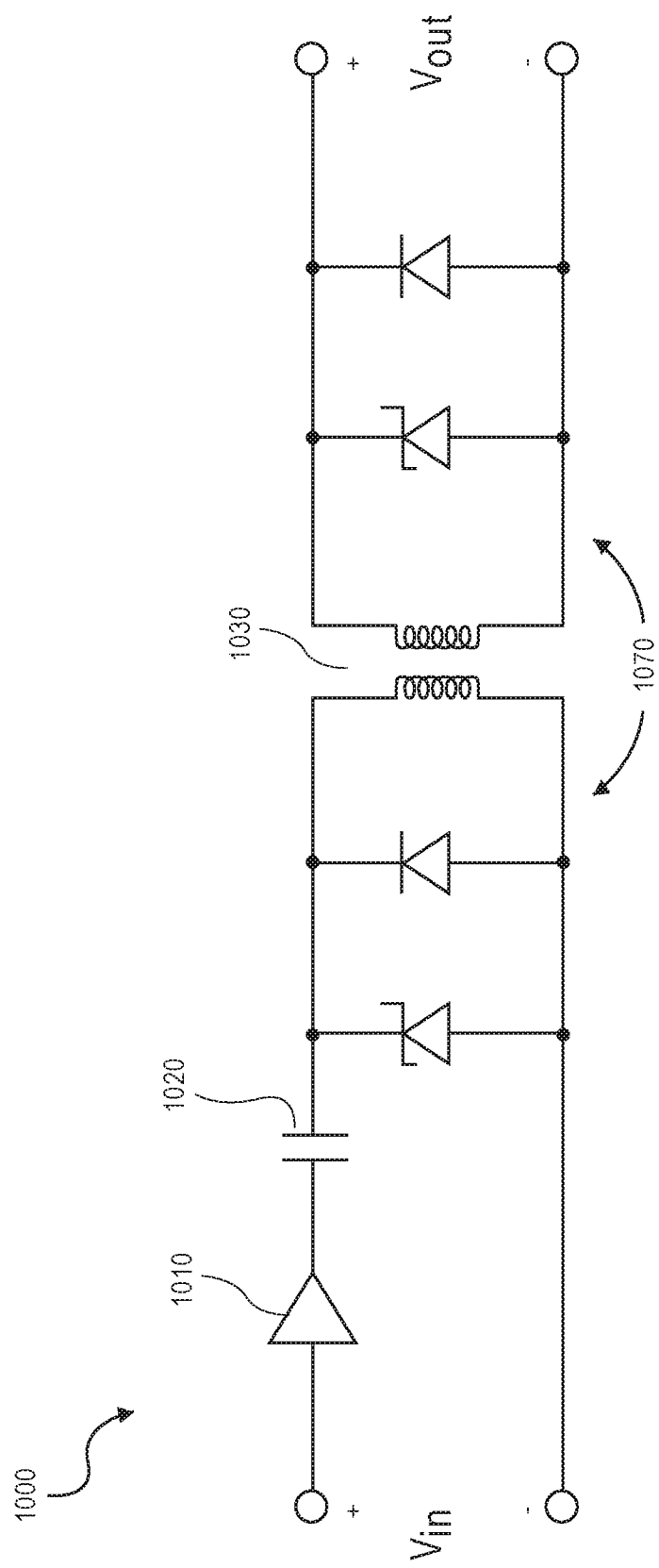
FIG. 10 is an electrical schematic of one of the switch drivers shown in FIG. 9.

FIG. 10 illustrates a switch driver 1000 which may be used as one of the switch drivers shown in FIG. 9.

Switch driver 1000 receives trigger pulses across input port Vin, and generates control signal pulses at output port Vout in response to the received trigger pulses. Switch driver 1000 includes amplifier circuit 1010, capacitor 1020, and transformer 1030. In some embodiments, switch driver 1000 also includes clamps circuits 1070.

Amplifier circuit 1010 receives the trigger pulses, and drives transformer 1030 through capacitor 1020, which reduces or blocks low frequency and DC signals. In response to being driven by amplifier circuit 1010, transformer 1030 generates control signal pulses at output port Vout, such that the duration of the control signal pulses is equal to or substantially equal (e.g. within 10% or 1%) to the duration of the trigger pulses at input port Vin.

In some embodiments, amplifier circuit 1010 includes multiple amplifier integrated circuits. For example, for increased current driving capability, multiple amplifier integrated circuits may be connected in parallel to form amplifier circuit 1010. For example, 2, 3, 4, 5, 6, 7, 8 or another number of amplifier integrated circuits may be used.

In some embodiments, clamp circuits 1070 are included at least to dampen potential signals, which may otherwise be caused by resonance. Clamp circuits 1070 include parallel diodes, which provide a short-circuit path for any current reversal, and also clamp the maximum voltage across the components connected to the clamp circuits 1070.

In some embodiments, the drivers 750, 850, and 1000 receive power from a DC-DC power module which is isolated from the power supply for the Marx generator. This ensures the cutoff of ground coupling.

In some embodiments, transformer 1030 has a 1:1 turns ratio. In alternative embodiments, a different turns ratio is used.

In some embodiments, in order to obtain very fast switching, the transformers 1030 has fewer than 5 turns in the primary winding and fewer than 5 turns in the secondary winding. For example, in some embodiments, the transformer 1030 has 1, 2, 3, or 4 turns in each of the primary and secondary windings. In some embodiments, the transformer 1030 has less than a complete turn, for example, ½ turn in the primary and secondary windings. The low number of turns in each of the primary and secondary windings allows for a low inductance loop and increases the current risetime in the secondary winding, which charges the input capacitance of the MOSFET switches.

Transformers for triggering MOSFETs in conventional applications require high coupling, high permeability, and a low-loss core in order to ensure current transfer efficiency. From pulse to pulse, the residual flux in the core needs to be cleared in order to avoid saturation when the transformer is operated at high frequency. Conventionally, a resetting circuit, which involves a third winding, to dissipate the core energy is used.

In some embodiments, lossy transformers, such as that typically used as an electromagnetic interference (EMI) choke to confine high frequency signals and dissipate their energy as heat are used to trigger the switches. For example, the transformers may have a voltage time constant less than 100Vμs. In some embodiments, the Transformers have a voltage time constant less than 50Vμs, 30Vμs, 20Vμs, 10Vμs, or 5Vμs. The use of the lossy transformer is contrary to the common practice in power electronics.

Although the high frequency flux is dampened due to the loss of the core (eddy loss, hysteresis loss, and resistive loss), the lossy transformers still allow sufficient confinement of the magnetic flux and provides sufficient coupling. In addition, the flux also decreases quickly in response to the signal on the primary winding being removed. The flux decay process usually takes approximately several microseconds.

Having such a transformer conventionally seems disadvantageous, but for coupling nanosecond to a few microsecond pulses, such a transformer is preferably used. Consequently, the following benefits are achieved: 1) high voltage, high frequency transient coupling from the high-voltage Marx generators to the low-voltage drivers is suppressed; 2) because of the loss in the transformer cores, the residual flux from previous pulses are dissipated faster than common low-loss transformer cores, such that the resetting winding is not needed and is not present.

A benefit of the switch driver 1000 is that it limits the output pulse duration. Because the switch control signals are generated by transformer 1030, even if circuitry generating the input trigger signals at input port Vin were to generate a pulse of indefinite length, the transformer would saturate, causing the control signals to turn off the switches.

Figure 11:
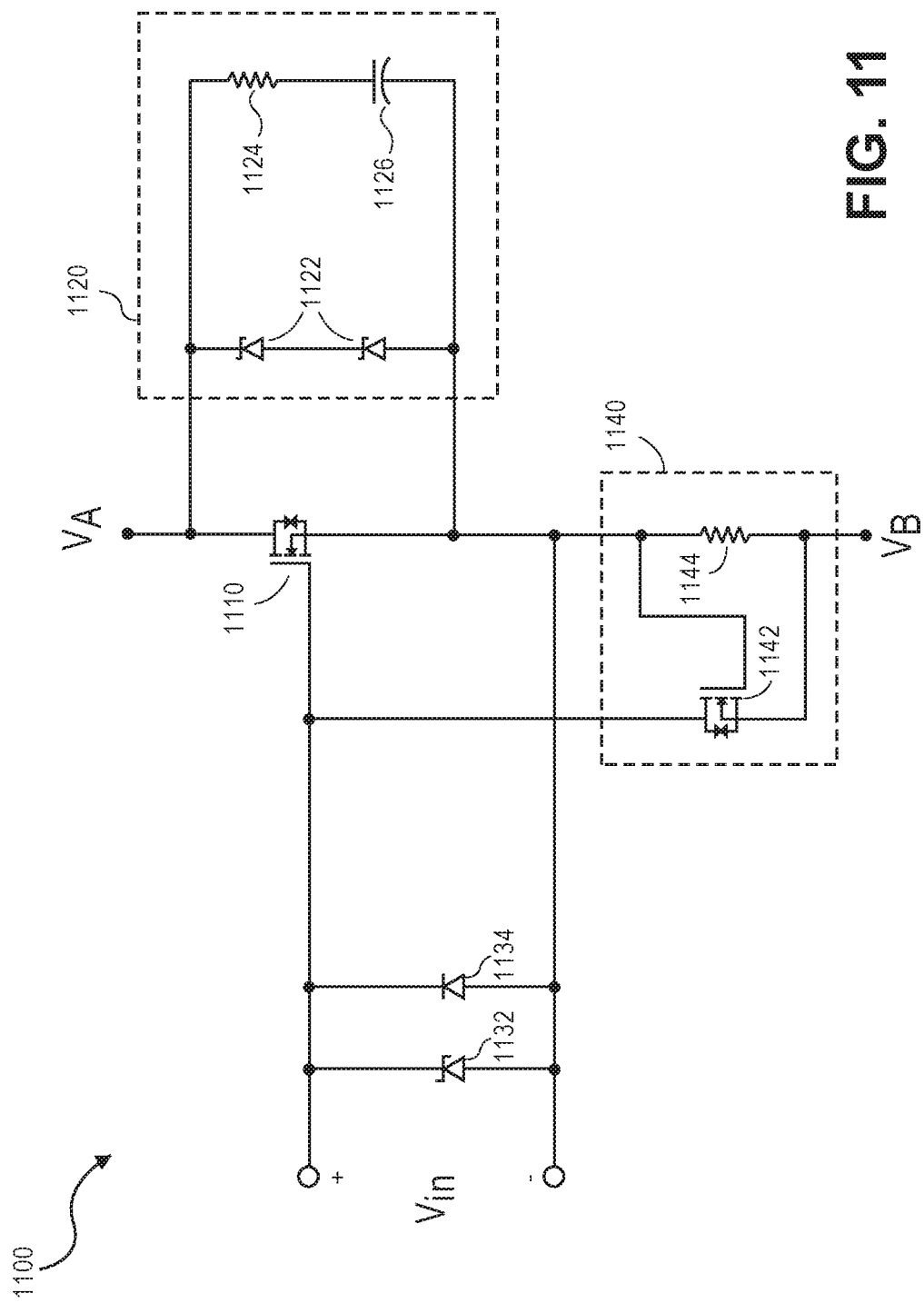
FIG. 11 is an electrical schematic of an alternative switch element.

FIG. 11 illustrates an example of a switch element 1100 comprising components which may be used in the switch stacks discussed here. Switch element 1100 includes switch 1110, and selectively forms a conductive or low resistance path between terminals VA and VB in response to a control voltage applied to input port Vin.

In some embodiments, switch 1110 is a transistor, such as a MOSFET. In some embodiments, switch 1110 is another type of switch. In some embodiments, switch 1110 has a turn on time of less than 5 ns, about 5 ns, about 10 ns, about 25 ns, about 15 ns, about 75 ns, about 100 ns, or greater than 100 ns.

In some embodiments, switch element 1100 also includes snubber circuit 1120. In some embodiments, the turn on times of the switches of the switch stacks are not identical. In order to prevent voltages greater than that which switch 1110 can tolerate, snubber circuit 1120 provides a current shunt path bypassing switch 1110. Diodes 1122 provide a low-frequency current path, and the combination of the capacitor 1126 and resistor 1124 provide a high-frequency current path.

In some embodiments, switch element 1100 also includes optional overcurrent protection circuit 1140. Overcurrent protection circuit 1140 includes switch 1142 and sense resistor 1144.

Current flowing from terminal VA to terminal VB is conducted through sense resistor 1144. Accordingly, a voltage is generated across sense resistor 1144 when the current flows from terminal VA to terminal VB. The generated voltage controls a conductive state of switch 1142. If the current flowing from terminal VA to terminal VB is greater than a threshold, the generated voltage causes the switch 1142 to conduct. As a result, switch 1142 reduces the control voltage of switch 1110. In response to the reduced control voltage, switch 1110 becomes less conductive or turns off. Consequently, the current which may be conducted from terminal VA to terminal VB is limited by overcurrent protection circuit 1140.

In some embodiments, a current limiting resistor is placed between the gate of switch 1110 and the drain of switch 1142 to prevent switch 1142 from experiencing current greater than that which would cause damage.

In the embodiments discussed herein, MOSFET switches are used. In alternative embodiments, other switches are used. For example, in some embodiments, thyristors, IGBTs or other semiconductor switches are used.

Figure 12:
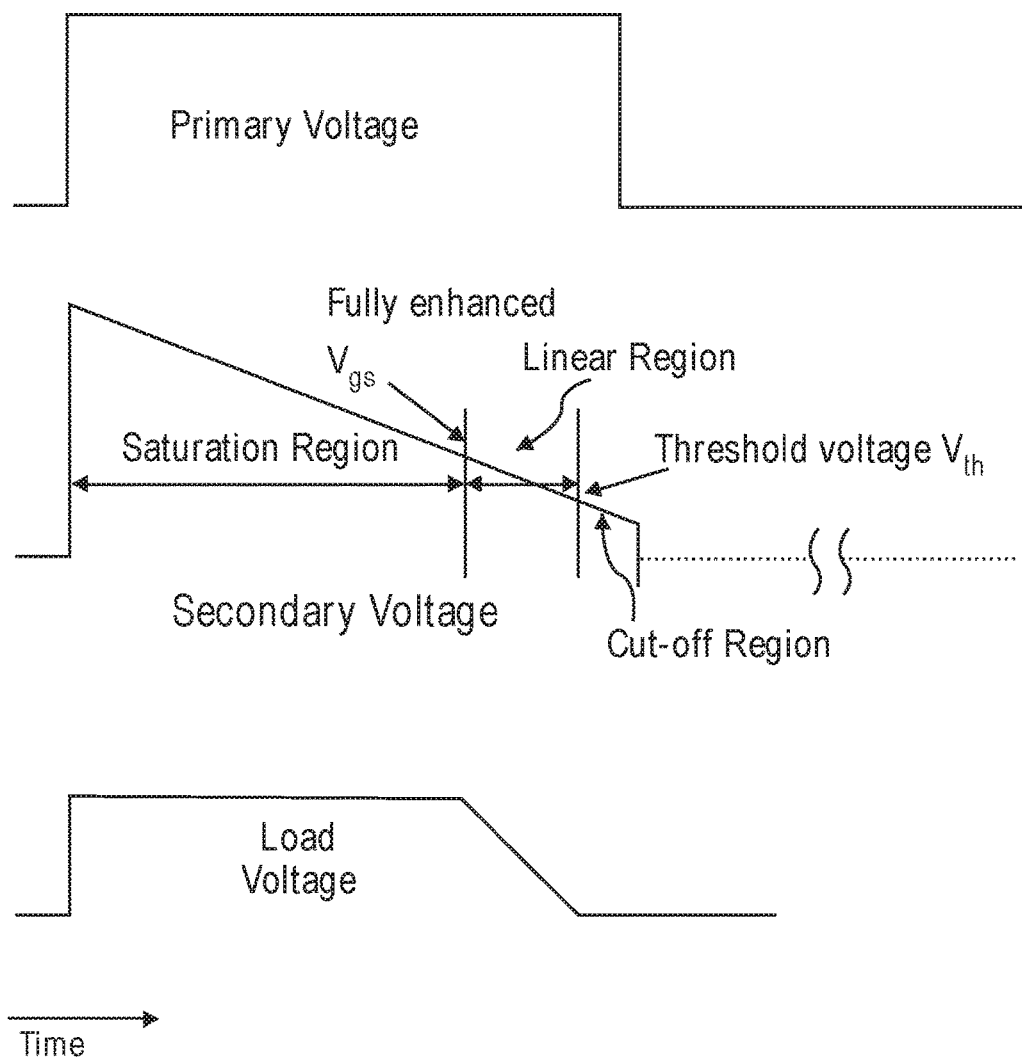
FIG. 12 is a waveform diagram illustrating the operation of a transformer and a control voltage to a MOSFET gate.

An example of the operation of the transformer is illustrated in FIG. 12. The voltage at the input primary inductor is substantially a square waveform, but the voltage at the secondary inductor, which is the MOSFET's gate-source voltage, tapers as the voltage magnitude decreases toward zero, for example, within a period of several microseconds. After a reduction in voltage at the secondary inductor due to transformer saturation, the switch receiving the voltage enters a linear region of operation from a saturation region of operation when the voltage is lower than the fully enhanced Vgs. As a result, the resistance of the switch increases and the output voltage across the load also shows a tapered profile. When the voltage at the secondary inductor decreases to a value less than the turn-on threshold of a MOSFET (Vth), the MOSFET will be shut off. Once the MOSFET is off, even if the duration of the trigger signal is extended, the switch no longer conducts and can be considered an open circuit. The waveform of the voltage at the secondary inductor therefore limits the duration of high voltage output pulses from each panel, for example, to be several microseconds or less.

In some embodiments, the duration of the trigger signal is short enough that the switches remain in saturation because the reduction in voltage at the secondary inductor is insufficient to cause the switches to enter linear region operation. In such embodiments, the load voltage pulses do not exhibit the tapering illustrated in FIG. 12. For example, in such embodiments the load voltage pulses may be substantially square.

In some embodiments, the switch stacks discussed herein include switches, as discussed above, as well as other components.

In some embodiments, when generating pulses of a duration less than a threshold, the shape of the pulses are substantially square. In some embodiments, when generating pulses of the duration greater than a threshold, the shape of the pulses are substantially square for a duration substantially equal (e.g. within 10% or 1%) to the threshold. During the time after the threshold, the voltage of such long pulses drops toward 0 V. In some embodiments, the drop toward 0 V is substantially linear. In some embodiments, the drop toward 0 V is substantially exponential.

Figure 13:
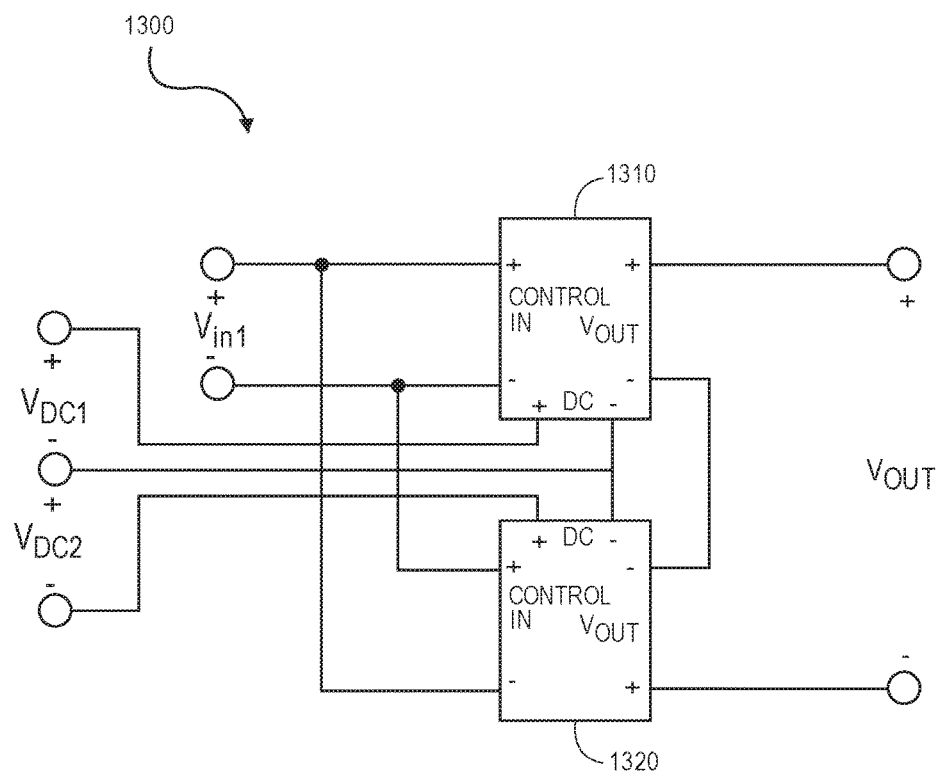
FIG. 13 is an alternative electrical schematic of a pulse generator shown in FIG. 1.

FIG. 13 illustrates an alternative pulse generator circuit 1300 which may be used inside nsPEF system 100 of FIG. 1.

Pulse generator circuit 1300 receives input pulses across input port Vin and DC voltages at input ports VDC1 and VDC2, and generates output pulses across output port Vout in response to the received input pulses and DC voltages.

Pulse generator circuit 1300 includes multiple pulse generator circuits 1310 and 1320. In this embodiment, two pulse generator circuits are used. In alternative embodiments, more pulse generator circuits are used. For example, in some embodiments, 3, 4, 5, 10 or another number of pulse generator circuits having their output ports serially connected, as discussed below with reference to pulse generator circuit 1300, are used.

Each of pulse generator circuits 1310 and 1320 may be similar to the other pulse generator circuits discussed herein. For example pulse generator circuits 1310 and 1320 may be similar to or may be substantially identical to pulse generator circuit 700 discussed above with reference to FIG. 7.

Each of pulse generator circuits 1310 and 1320 receive the same input pulse signal across their respective Control In input ports. In response, each of pulse generator circuits 1310 and 1320 generate high voltage pulses across their respective Vout output ports. Because the Vout output ports of pulse generator circuits 1310 1320 are serially connected, the voltage pulse generated by pulse generator circuits 1310 and 1320 across output port Vout of pulse generator circuit 1300 is substantially equal (e.g. within 10% or 1%) to the sum of the voltages of the pulses respectively generated by pulse generator circuits 1310 and 1320.

Figure 14:
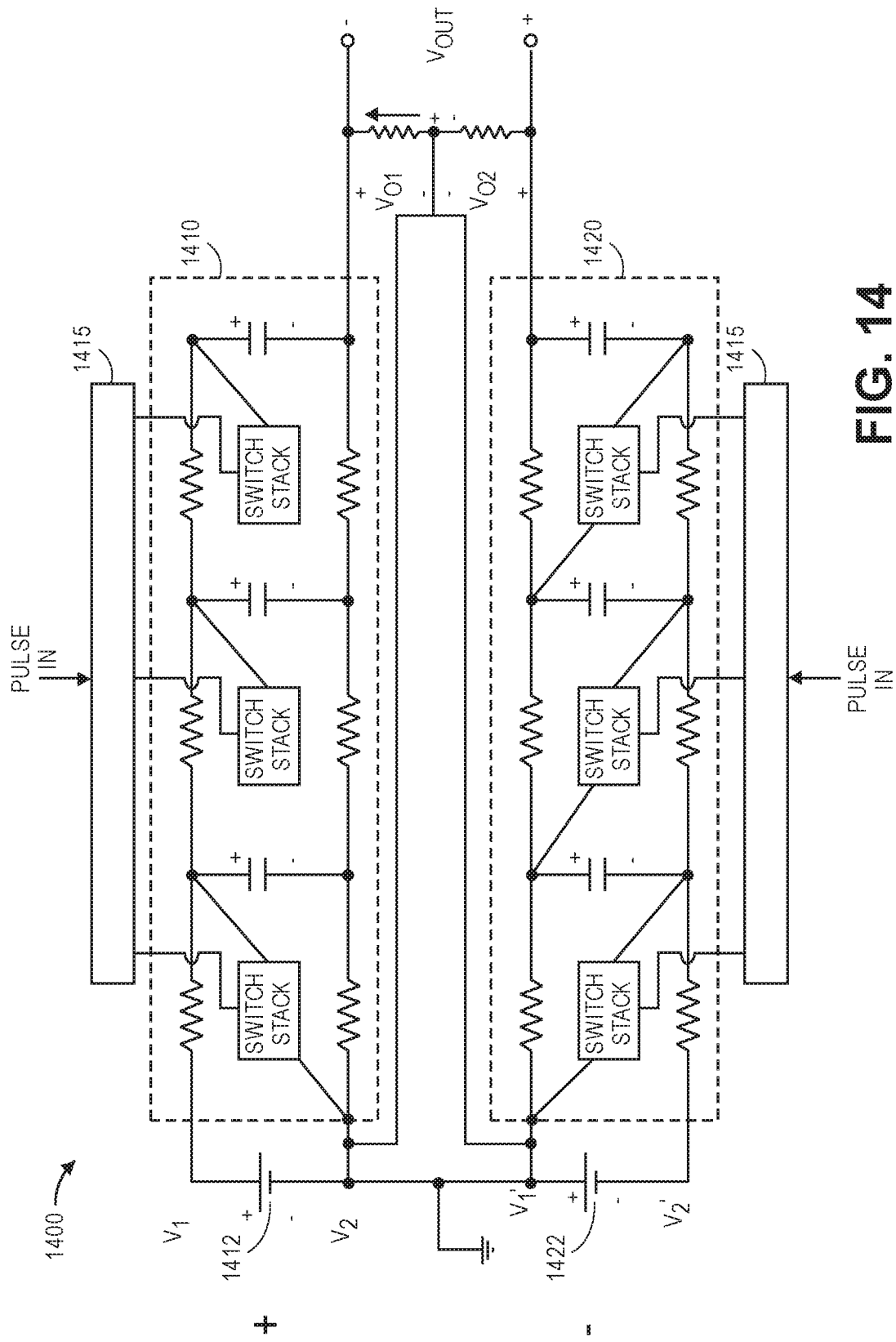
FIG. 14 is an alternative electrical schematic of a pulse generator shown in FIG. 1.

FIG. 14 illustrates an alternative pulse generator circuit 1400 which may be used inside nsPEF system 100 of FIG. 1, and which has characteristics similar to the pulse generator 1300 of FIG. 13. Pulse generator circuit 1400 includes pulse generators 1410 and 1420, drivers 1415 and 1425, and power supplies 1412 and 1422.

Pulse generator circuit 1400 includes multiple pulse generator circuits 1410 and 1420. In this embodiment, two pulse generator circuits are used. In alternative embodiments, more pulse generator circuits are used. Each of pulse generator circuits 1410 and 1420 may be similar to the other pulse generator circuits discussed herein.

Pulse generator circuit 1400 receives input pulses at each of drivers 1415 and 1425, which may be similar to driver 850 discussed above with reference to FIG. 8. Pulse generator circuit 1400 generates output pulses across output port Vout in response to the received input pulses. The output voltage pulses are also based on power voltages received from power supplies 1412 and 1422.

Each of drivers 1415 and 1425 receive an input pulse signal. In response to the received input signals, drivers 1415 and 1425 respectively generate driving signal pulses for pulse generator circuits 1410 and 1420. In response to the driving signal pulses, each of pulse generator circuits 1410 and 1420 generate high voltage pulses across their respective output ports Vo1 and Vo2. Because the Vo1 and Vo2 output ports of pulse generator circuits 1410 and 1420 are serially connected, the voltage pulse generated by pulse generator circuits 1410 and 1420 across output port Vout of pulse generator circuit 1400 is substantially equal (e.g. within 10% or 1%) to the sum of the voltages of the pulses respectively generated by pulse generator circuits 1410 and 1420.

In this embodiment, pulse generator circuit 1410 generates a high voltage pulse across its output port Vo1 which is substantially equal (e.g. within 10% or 1%) to three times the voltage of power supply 1412, $(-3\times[V1-V2])$. In addition, pulse generator circuit 1420 generates a high voltage pulse across its output port Vo2 which is substantially equal (e.g. within 10% or 1%) to three times the voltage of power supply 1414 $(3\times[V'1-V'2])$. As a result, pulse generator circuit 1400 generates a voltage of $(3\times[V'1-V'2])-(-3\times[V1-V2])$ across its output port Vout.

In some embodiments, a single driver circuit connected to both pulse generator circuit 1410 and 1420 is used instead of drivers 1415 and 1425. In such embodiments, the single driver circuit generates driving signal pulses for both pulse generator circuits 1410 and 1420 in response to an input pulse signal.

Figure 15:
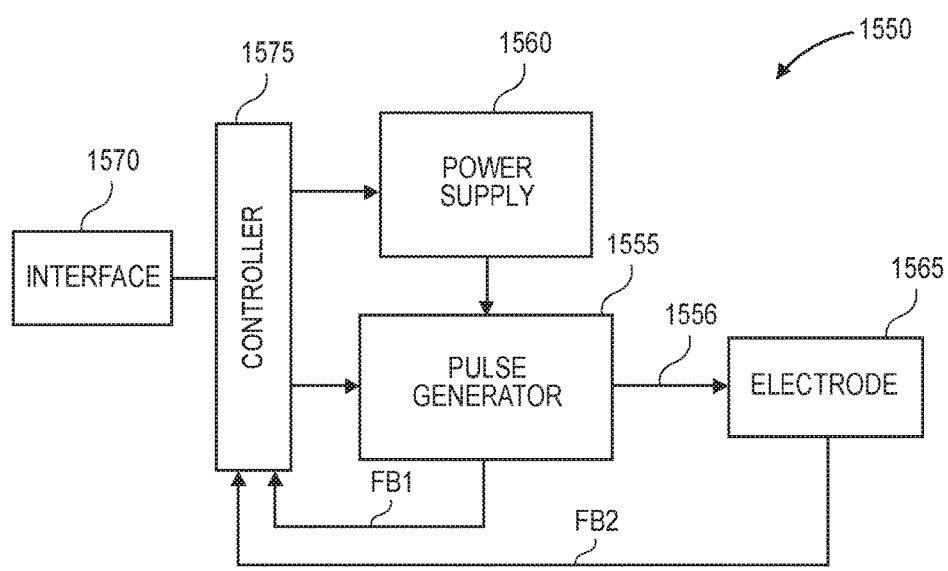
FIG. 15 is a block diagram of a nsPEF treatment system.

FIG. 15 is a block diagram of a nsPEF treatment system 1550, which has characteristics similar to or identical to those of nsPEF system 100 illustrated in FIG. 1. NsPEF treatment system 1550 includes pulse generator 1555, power supply 1560, nsPEF pulse applicator 1565, interface 1570, and controller 1575.

Pulse generator 1555 may be similar or identical to any of the pulse generator circuits discussed herein. For example, pulse generator 1555 may be configured to generate pulses having a voltage magnitude corresponding with power voltages received from power supply 1560 and having pulse widths and other characteristics corresponding with control signals received from controller 1575. In alternative embodiments, other pulse generator circuits may be used.

NsPEF pulse applicator 1565 may be similar or identical to any of the nsPEF pulse applicators discussed herein. For example, nsPEF pulse applicator 1565 may be similar or identical to nsPEF pulse applicators 300 and 400 discussed above with reference to FIGS. 3 and 4. NsPEF pulse applicator 1565 is configured to receive nsPEF pulses generated by pulse generator 1555 from conductor 1556 and is configured to deliver nsPEF pulses to a patient or experiment subject undergoing therapeutic nsPEF treatment. In alternative embodiments, other therapeutic nsPEF pulse applicators may be used.

Sensor 1566 may include one or more of a thermocouple, a voltage probe, a current probe, an impedance probe, a capacitance probe, a light sensor, a humidity sensor, a tissue monitoring probe, and a chemical analysis probe. Sensor 1566 may be configured to sense one or more characteristics of the patient or experiment subject, the nsPEF pulse applicator 1565, the nsPEF pulses delivered by the nsPEF pulse applicator 1565, and effects of the nsPEF pulses delivered by the nsPEF pulse applicator 1565.

Power supply 1560 is configured to provide power voltages to pulse generator 1555. For example, in embodiments where pulse generator 1555 is similar to pulse generator circuit 700 illustrated in FIG. 7, power supply 1560 may be configured to provide power voltages corresponding with power voltages V1 and V2 of pulse generator circuit 700. In some embodiments, power supply 1560 generates and provides power voltages which have a voltage level corresponding with a control signal from controller 1575.

Interface 1570 is configured to receive input from a user identifying various parameters and characteristics of the nsPEF pulses to be applied to the patient or experiment subject. For example, interface 1570 may be configured to receive input identifying or specifying values for one or more characteristics of one or more nsPEF pulses to be applied to the patient or experiment subject. For example, the characteristics may include one or more of an amplitude, a polarity, a width, a rise time, and a fall time of one or more nsPEF pulses to be applied to the patient or experiment subject. Additionally or alternatively, the characteristics may include one or more of a frequency and a pulse quantity of a sequence of nsPEF pulses to be applied to the patient or experiment subject. Furthermore, the characteristics may additionally or alternatively include a result of the nsPEF pulses to be applied to the patient or experiment subject, such as a maximum temperature for the treated tissue of the patient or experiment subject. Other characteristics may additionally or alternatively be identified or specified by the received input.

In addition, interface 1570 is configured to communicate the characteristics identified or specified by the received input to controller 1575.

Controller 1575 is configured to generate and provide one or more control signals to pulse generator 1555 and to power supply 1560 based at least partly on the communicated characteristics received from interface 1570. Additionally, pulse generator 1555, power supply 1560, and nsPEF pulse applicator 1565 are collectively configured to, in response to the control signals from controller 1575, generate nsPEF pulses having characteristics corresponding with the control signals.

In this embodiment, one or more of pulse generator 1555, nsPEF pulse applicator 1565, and sensor 1566 are configured to generate corresponding feedback signals FB1, FB2, and FB3 representing measured parametric characteristics of the nsPEF pulses applied to the patient or experiment subject or other signals of nsPEF treatment system 1550. In some embodiments, the parametric characteristics of the nsPEF pulses represented by the feedback signals FB1, FB2, and FB3 include one or more of an amplitude, a polarity, a width, a rise time, and a fall time of the nsPEF pulses. In some embodiments, the parametric characteristics of the nsPEF pulses represented by the feedback signals, FB2, and FB3 additionally or alternatively include one or more of current and voltage applied to the tissue so that one or more of tissue impedance, tissue inductance, tissue capacitance, instantaneous power applied to the tissue, and energy applied to the tissue may be calculated. In some embodiments, the parametric characteristics represented by the feedback signal FB1 may additionally or alternatively include one or more of a voltage at a capacitor being charged during a charge mode of pulse generator 1555, voltage and/or current characteristics of a control signal of pulse generator 1555, voltage and/or current characteristics of a power supply signal of pulse generator 1555, voltage and/or current characteristics of a pulse generated by pulse generator 1555, and voltage and/or current characteristics of another input, output, or internal signal of pulse generator 1555. Additionally or alternatively, the parametric characteristics may include a frequency of a sequence of nsPEF pulses. Furthermore, the parametric characteristics may additionally or alternatively include a temperature of the treated tissue of the patient or experiment subject. The feedback signals, FB2, and FB3 may correspond or represent other measured parametric characteristics of one or more of the nsPEF pulses applied to the patient or experiment subject, the patient or experiment subject, the environment, and the nsPEF treatment system 1550.

In some embodiments, controller 1575, power supply 1560, pulse generator 1555, nsPEF pulse applicator 1565, and optionally sensor 1566 collectively form a feedback loop which causes one or more parametric characteristics of the nsPEF pulses applied to the patient or experiment subject to have measured values substantially equal (e.g. within 10% or 1%) to the values of corresponding characteristics identified in the input received by interface 1570.

For example, interface 1570 may receive input specifying a value of 15 kV for an amplitude of the nsPEF pulses applied to the patient or experiment subject. In addition, the controller 1575 may be configured to, in response to a feedback signal FB2 from nsPEF pulse applicator 1565, a feedback signal FB1 from pulse generator 1555, or a feedback signal FB3 from sensor 1566 indicating that the measured amplitude of the nsPEF pulses applied to the patient or experiment subject is less than (or greater than) 15 kV, change a control signal provided to power supply 1560. In response to the changed control signal, power supply 1560 may be configured to increase (or decrease) the voltage of power signals provided to pulse generator 1555 such that the amplitude of the nsPEF pulses generated and applied to the patient or experiment subject increases (or decreases) to or toward 15 kV.

Similarly, interface 1570 may receive input specifying a value of 150 ns for a pulse width of the nsPEF pulses applied to the patient or experiment subject. The controller 1575 may be configured to, in response to a feedback signal FB3 from sensor 1566, a feedback signal FB2 from nsPEF pulse applicator 1565, or a feedback signal FB1 from pulse generator 1555 indicating that the measured pulse width of the nsPEF pulses applied to the patient or experiment subject is greater than (or less than) 150 ns, change a control signal provided to pulse generator 1555. In response to the changed control signal, pulse generator 1555 may be configured to generate and apply to the patient or experiment subject nsPEF pulses having decreased (or increased) pulse width. As a result, one or more of the feedback signals FB1, FB2, and FB3 causes the controller 1575 to generate control signals which cause the pulse generator 1555 to generate and apply nsPEF pulses having pulse widths decreased (or increased) to or toward 150 ns.

In some embodiments, the feedback loop is controlled using a Proportional-Integral-Derivative (PID) method. For example, using the PID method, controller 1575 may be configured to continuously or substantially continuously calculate an error value as the difference between a desired value perceived at interface 1570 and a corresponding measured parameter. In addition, using the PID method, controller 1575 may be configured to continuously or substantially continuously calculate the control signals as a sum of one or more of: a first constant times the error signal, a second constant times an integral of the error signal, and a third constant times a derivative of the error signal, where the first, second, and third constants may be positive, negative, or equal to zero. Other custom or standard control methods may additionally or alternatively be used.

In some embodiments, the feedback loop is controlled using a lookup table to determine a next value based on a measured value. In some embodiments, the feedback loop is controlled by reducing or increasing a value by a fixed amount or step size based on a determination of whether a measured value is greater than or less than a threshold.

Figure 16:
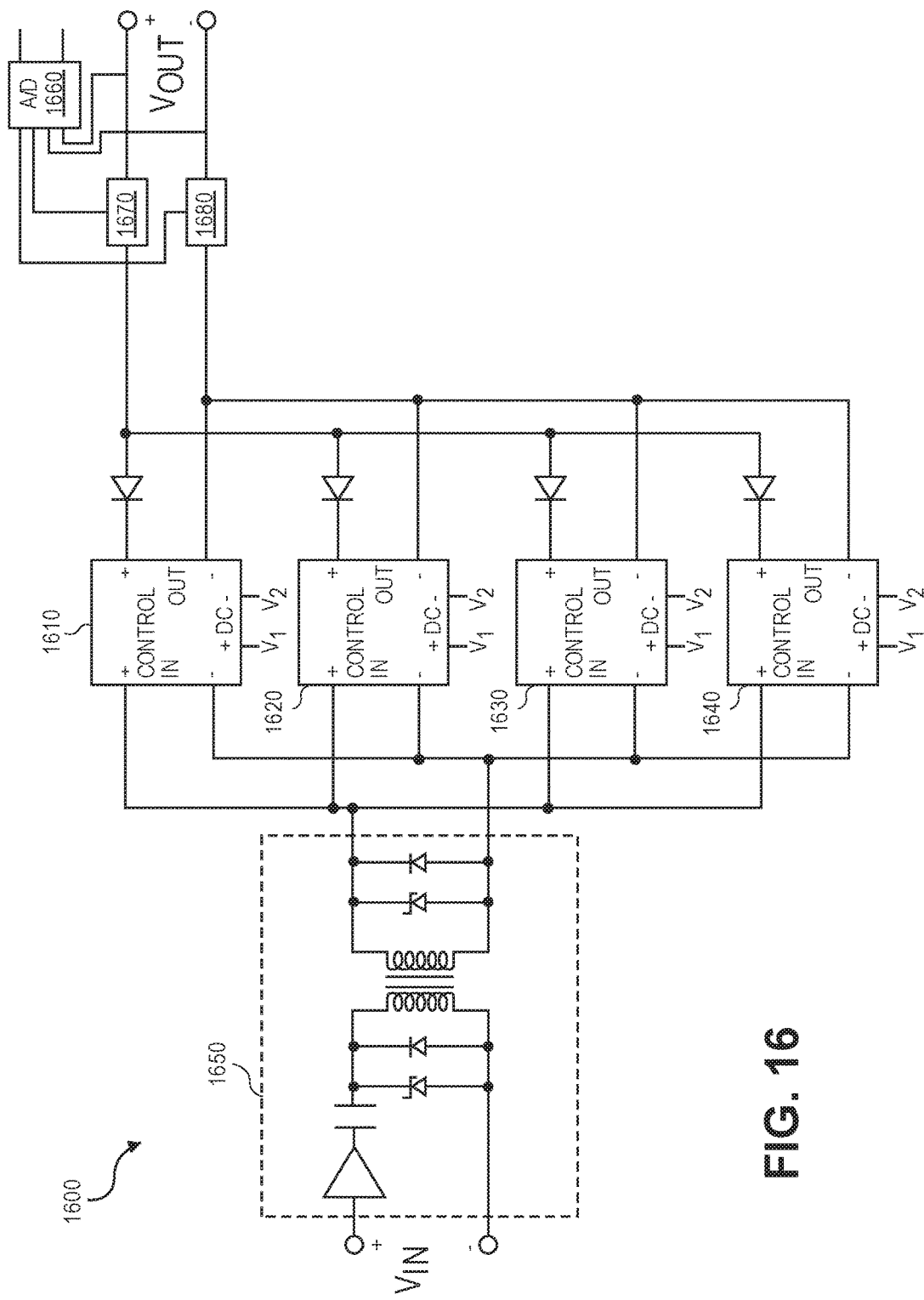
FIG. 16 is a schematic illustration of an alternative pulse generator.

FIG. 16 illustrates an alternative pulse generator 1600 which may be used as pulse generator 1555 of nsPEF treatment system 1550 illustrated in FIG. 15. Pulse generator 1600 may have features similar to or identical to other pulse generator circuits discussed herein. For example, pulse generator circuit 1600 may have features similar to or identical to pulse generator circuit 700 of FIG. 7.

For example, pulse generator 1600 includes the driver circuit 1650 which may be similar to or identical to driver 750 of pulse generator circuit 700. In addition, pulse generator 1600 includes pulse generator circuits 1610, 1620, 1630, and 1640, which may respectively be similar or identical to pulse generator circuits 710, 720, 730, and 740.

Pulse generator 1600 also includes, or in some embodiments is connected to, analog-to-digital converter 1660. Furthermore, pulse generator 1600 additionally or alternatively includes, or in some embodiments is connected to, current monitors 1670 and 1680.

In this embodiment, analog-to-digital (A/D) converter 1660 includes a first channel having inputs which are respectively connected to the positive (+) and negative (−) voltage output terminals of pulse generator 1600. In some embodiments, a first low input impedance differential buffer (not shown) is connected to the positive (+) and negative (−) voltage output terminals of pulse generator 1600, and drives the inputs of analog-to-digital converter 1660. In some embodiments, a probe, such as a Tektronix P6015 A Passive High Voltage Probe (not shown) is connected to the positive (+) and negative (−) voltage output terminals of pulse generator 1600, and drives the inputs of analog-to-digital converter 1660.

In some embodiments, only the positive (+) voltage output terminal is connected to analog-to-digital converter 1660. In some embodiments, the positive (+) voltage output terminal is connected to analog-to-digital converter 1660 through a voltage divider. In such embodiments, the voltage at the positive (+) voltage output terminal is ground referenced, and the ground is also connected to analog-to-digital converter 1660. For example, the positive (+) voltage output terminal is ground referenced if the negative (−) voltage output terminal of pulse generator 1600 is at the ground voltage.

In addition, analog-to-digital converter 1660 is configured to generate a first digital output representing the voltage difference between the positive (+) and negative (−) voltage output terminals of pulse generator 1600. When used in the nsPEF treatment system 1550 of FIG. 15, the first digital output may be used as a feedback signal for controller 1675. In some embodiments, analog-to-digital converter 1660 generates the first digital output based on either, but not both, of the voltages at the positive (+) and negative (−) voltage output terminals.

In this embodiment, analog-to-digital converter 1660 also includes a second channel having inputs which are respectively connected to the current monitors 1670 and 1680, and the current monitors 1670 and 1680 are respectively connected to the positive (+) and negative (−) voltage output terminals of pulse generator 1600. In some embodiments, a second low input impedance differential buffer (not shown) is connected to the current monitors 1670 and 1680, and drives the inputs of analog-to-digital converter 1660.

In addition, analog-to-digital converter 1660 is configured to generate a second digital output representing the current difference between the currents flowing through positive (+) and negative (−) voltage output terminals of pulse generator 1600. When used in the nsPEF treatment system 1550 of FIG. 15, the second digital output may be used as a feedback signal for controller 1575. In some embodiments, analog-to-digital converter 1660 generates the second digital output based on either, but not both, of inputs from the current monitors 1670 and 1680.

In some embodiments, current monitors 1670 and 1680 each include a sense resistor and an amplifier. The sense resistor is configured to generate a voltage response of the current flowing therethrough, and the amplifier generates an input for the analog-to-digital converter based on the voltage across the sense resistor.

In some embodiments, current monitors 1670 and 1680 include a current monitor, such as Pearson Current Monitor 2878, which generates a voltage in response to a sensed current.

In some embodiments, pulse generator 1600 generates either, but not both, of the first and second digital outputs. In some embodiments, one or more single channel analog-to-digital converters are used instead of or in addition to analog-to-digital converter 1660.

In some embodiments, only single current monitor is used. The single current monitor may monitor the current of either of the positive (+) and negative (−) voltage output terminals of pulse generator 1600.

FIGS. 17A-17H schematically illustrate multiple views of an nsPEF pulse applicator 1700 which may, for example, be used as nsPEF pulse applicator 1565 in nsPEF treatment system 1550 of FIG. 15. NsPEF pulse applicator 1700 may have characteristics similar to or identical to any of the nsPEF pulse applicators discussed herein. For example, nsPEF pulse applicator 1700 may have characteristics similar to or identical to nsPEF pulse applicators 300 and 400 discussed above with reference to FIGS. 3 and 4.

NsPEF pulse applicator 1700 includes bottom arm 1710, spacer 1720, and top arm 1730 connected together by fastener 1750. Bottom arm 1710 includes bottom electrode 1715, which is connected to one of the conductive wires 1740. Top arm 1730 includes top electrode 1735, which is connected to the other of the conductive wires 1740.

NsPEF pulse applicator 1700 is configured to receive nsPEF pulses across conductive wires 1740 and to deliver nsPEF pulses to a patient or experiment subject undergoing nsPEF treatment through top and bottom electrodes 1715 and 1735. The nsPEF pulses may, for example, be applied to a tumor of the patient or experiment subject which is positioned within a cavity 1725 of spacer 1720. Cavity 1725 forms a gap between top and bottom electrodes 1715 and 1735. In some applications, the tumor is connected to the patient or experiment subject by tissue which passes from the tumor within cavity 1725 to the patient or experiment subject between spacer 1720 and bottom arm 1710. In some embodiments, cavity 1725 is formed such that the gap between top and bottom electrodes 1715 and 1735 is open. For example, a portion of the gap may not be bounded by spacer 1720, top arm 1730, or bottom arm 1710.

Figure 17A:
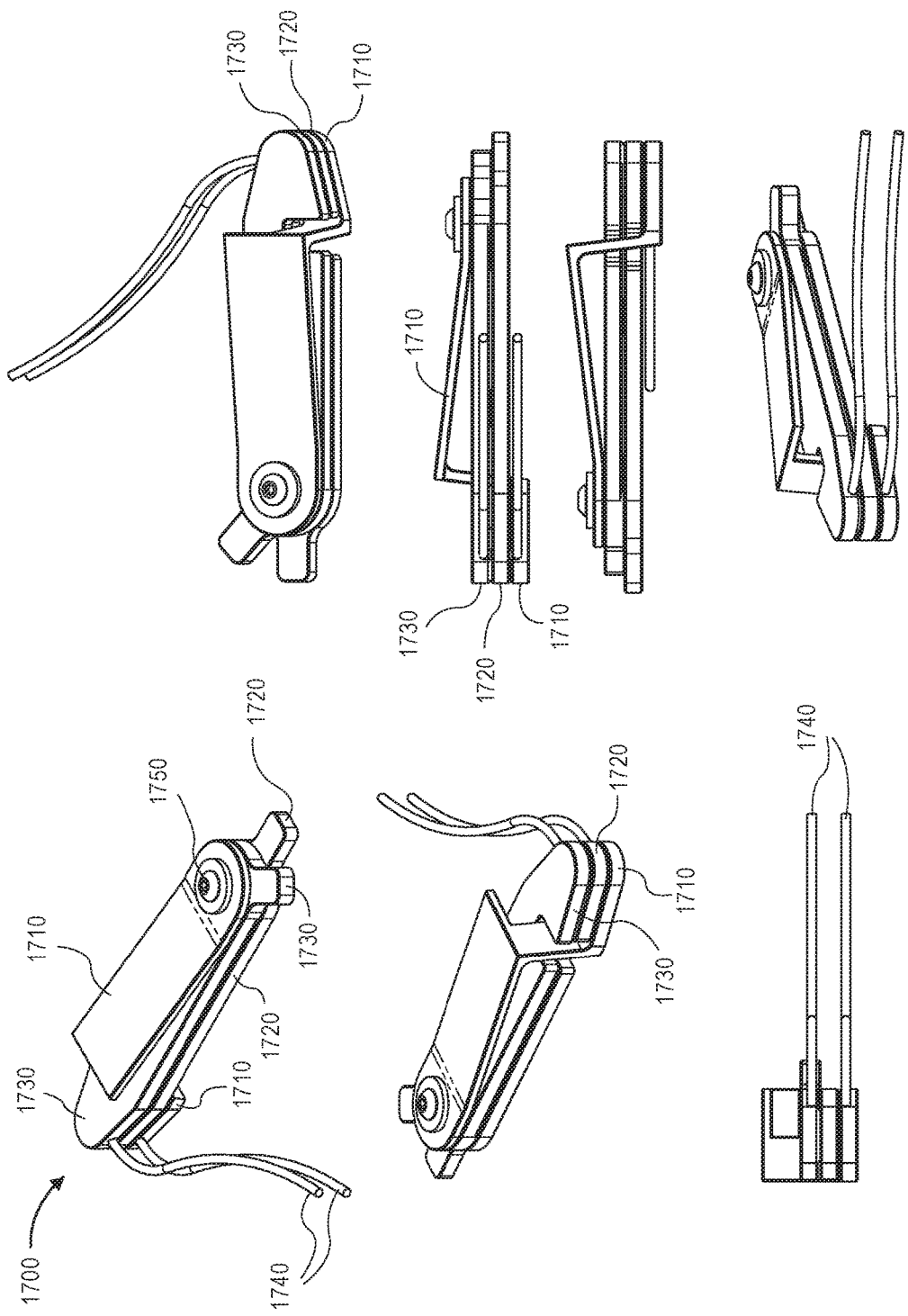
Figure 17B:
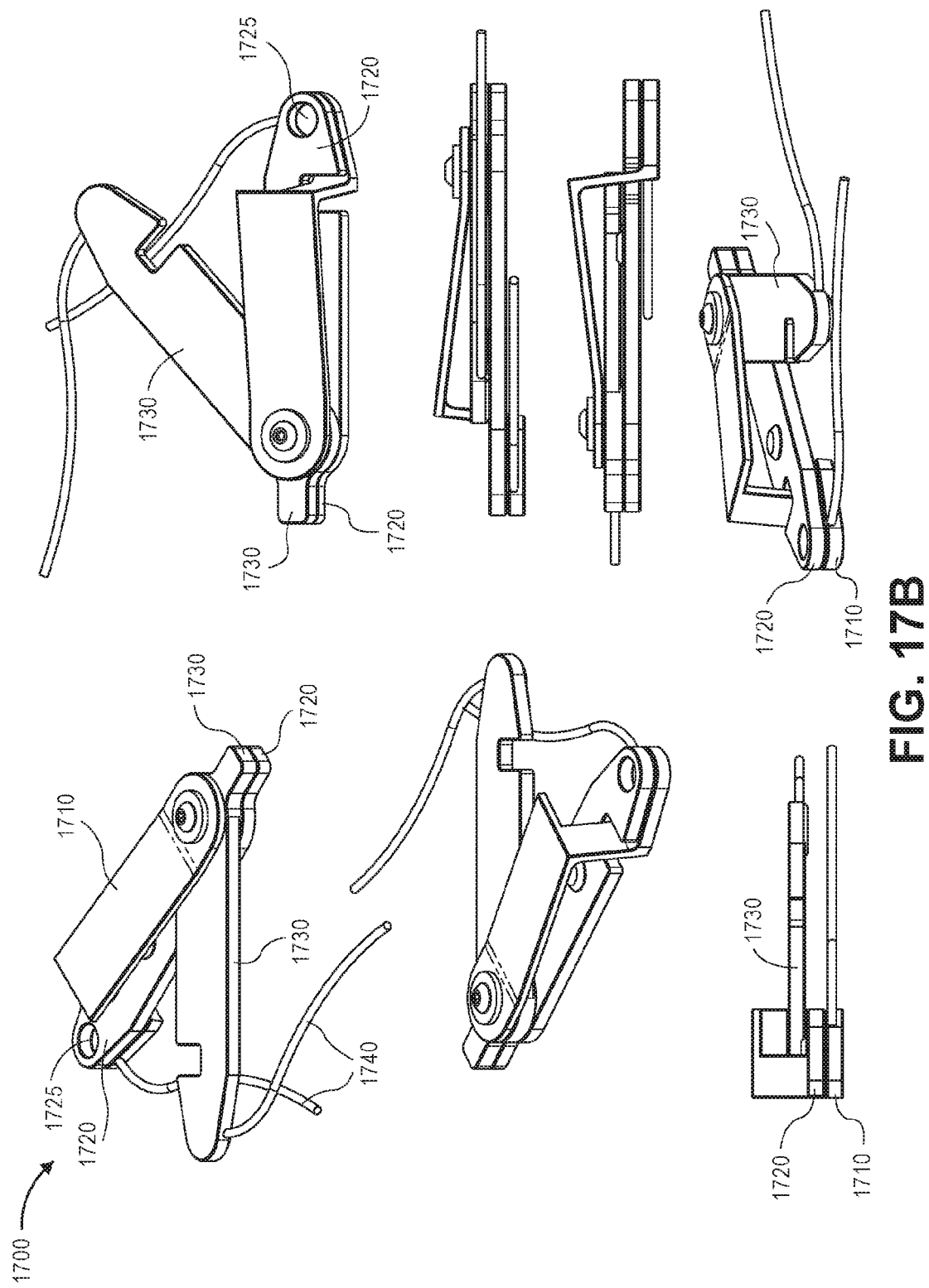
Figure 17C:
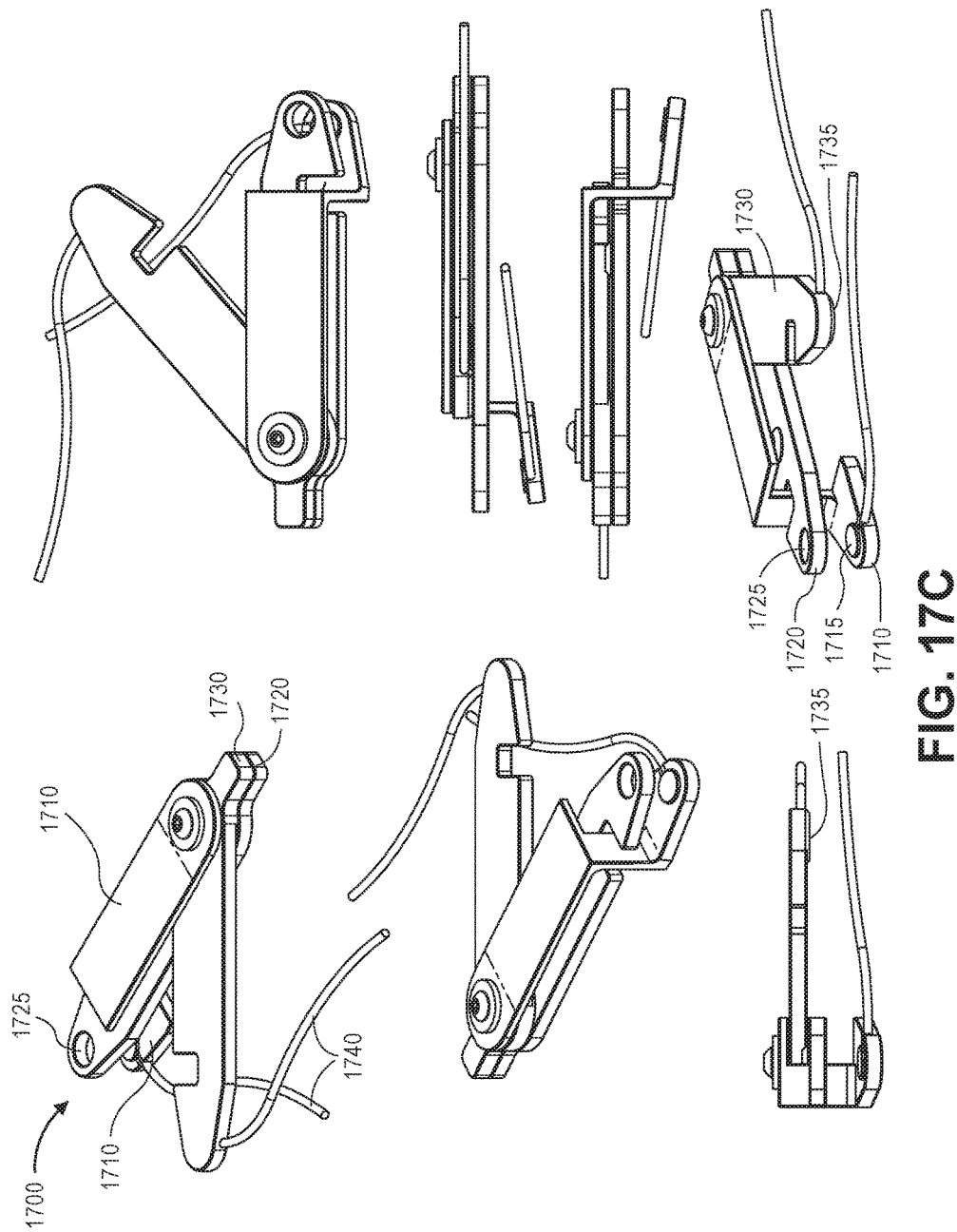

As shown, for example in FIG. 17A, bottom arm 1710 is separated from top arm 1730 by spacer 1720 near cavity 1725. In addition, near fastener 1750, bottom arm 1710 is adjacent to top arm 1730. In FIG. 17C, NsPEF pulse applicator 1700 is illustrated as if an external force is applied to bottom arm 1710 causing bottom arm 1710 to be separated from spacer 1720 near cavity 1725. In FIG. 17A, NsPEF pulse applicator 1700 is illustrated as if the external force is not applied to bottom arm 1710. As a result, bottom arm 1710 is substantially not separated from spacer 1720 near cavity 1725, as illustrate in FIG. 17A. In some embodiments, if no external force is applied causing bottom arm 1710 to be separated from spacer 1720 near cavity 1725, bottom arm 1710 is pressed against spacer 1720 by a force exerted by fastener 1750.

Figure 17D:
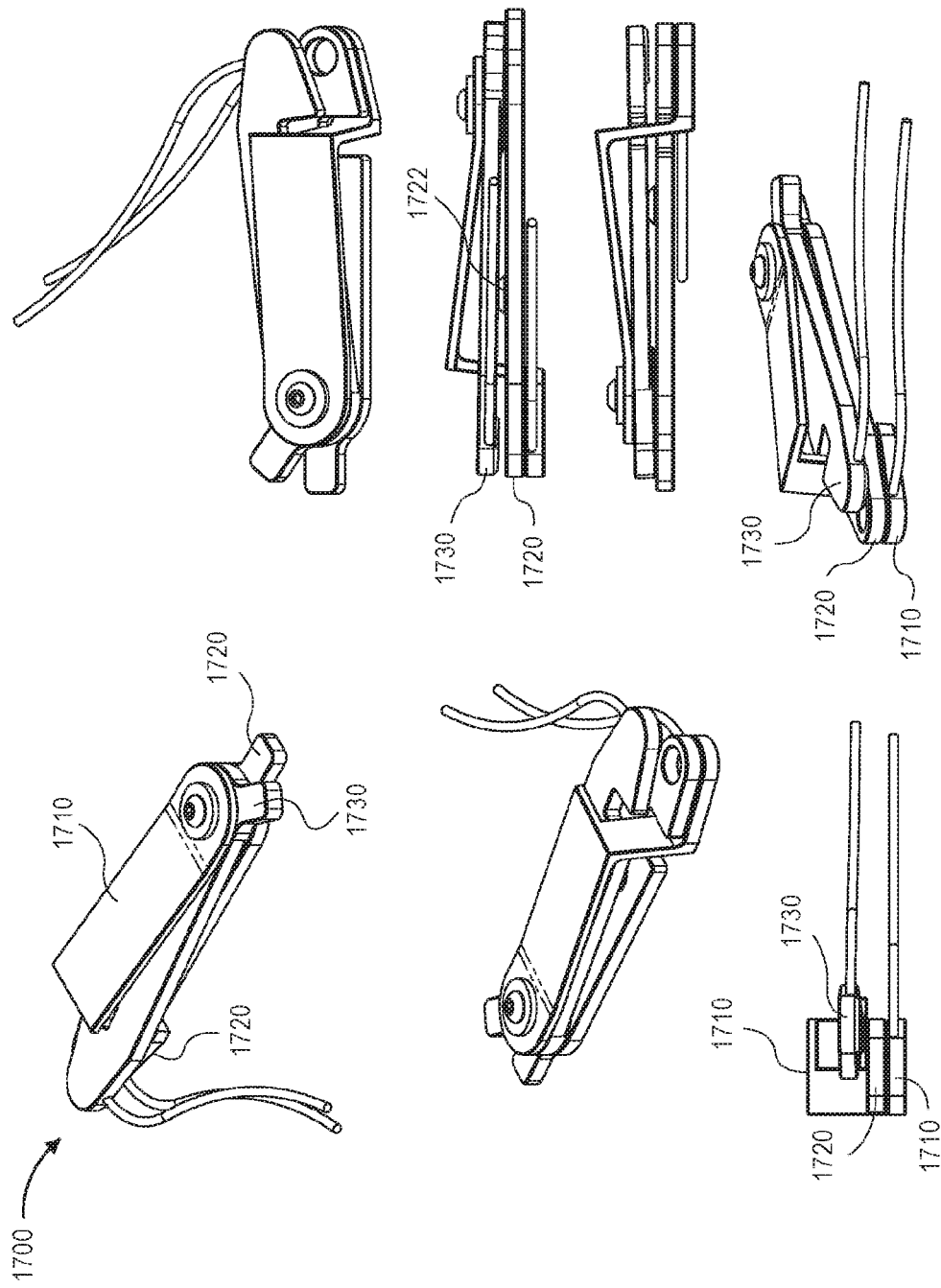
Figure 17F:
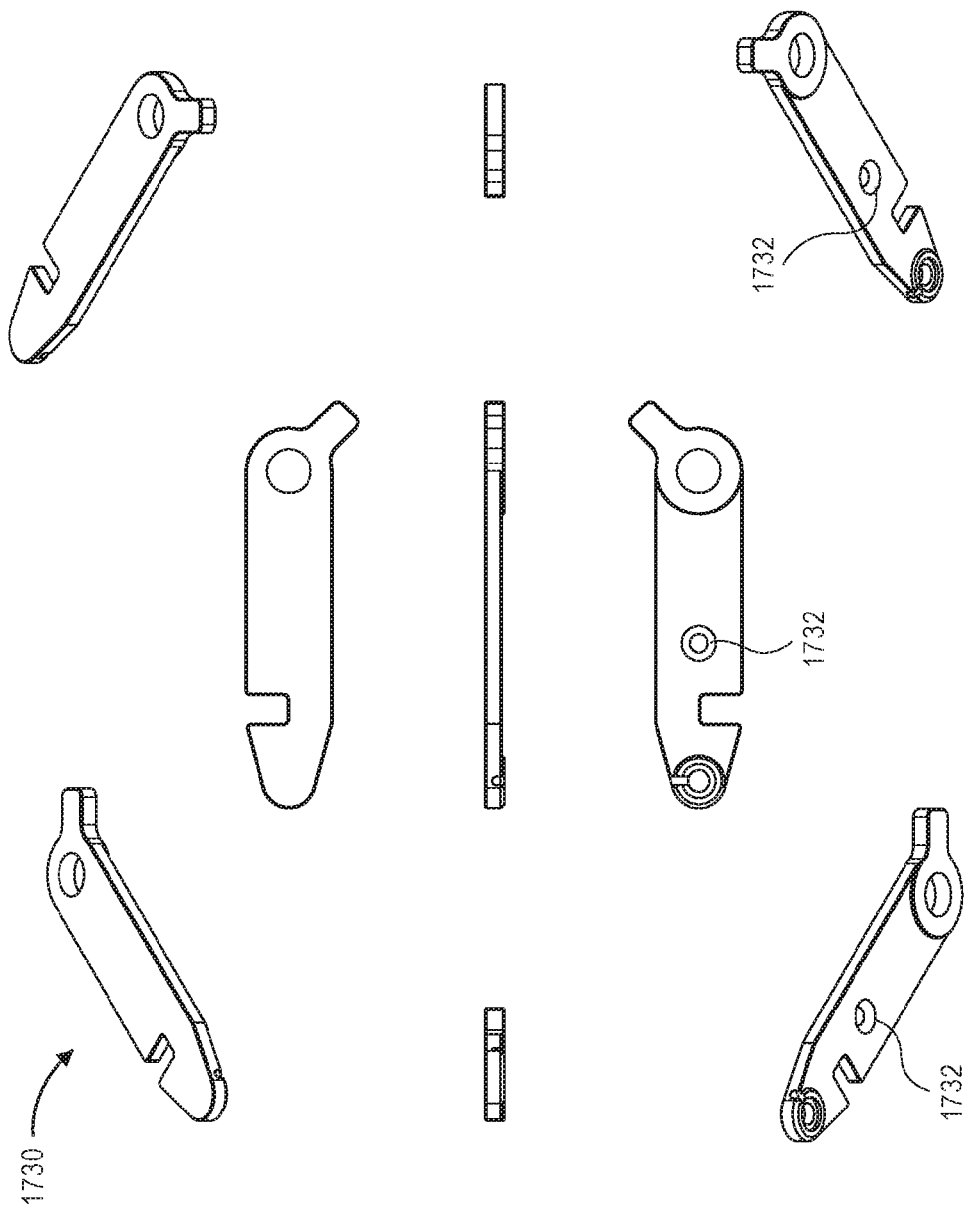
Figure 17H:
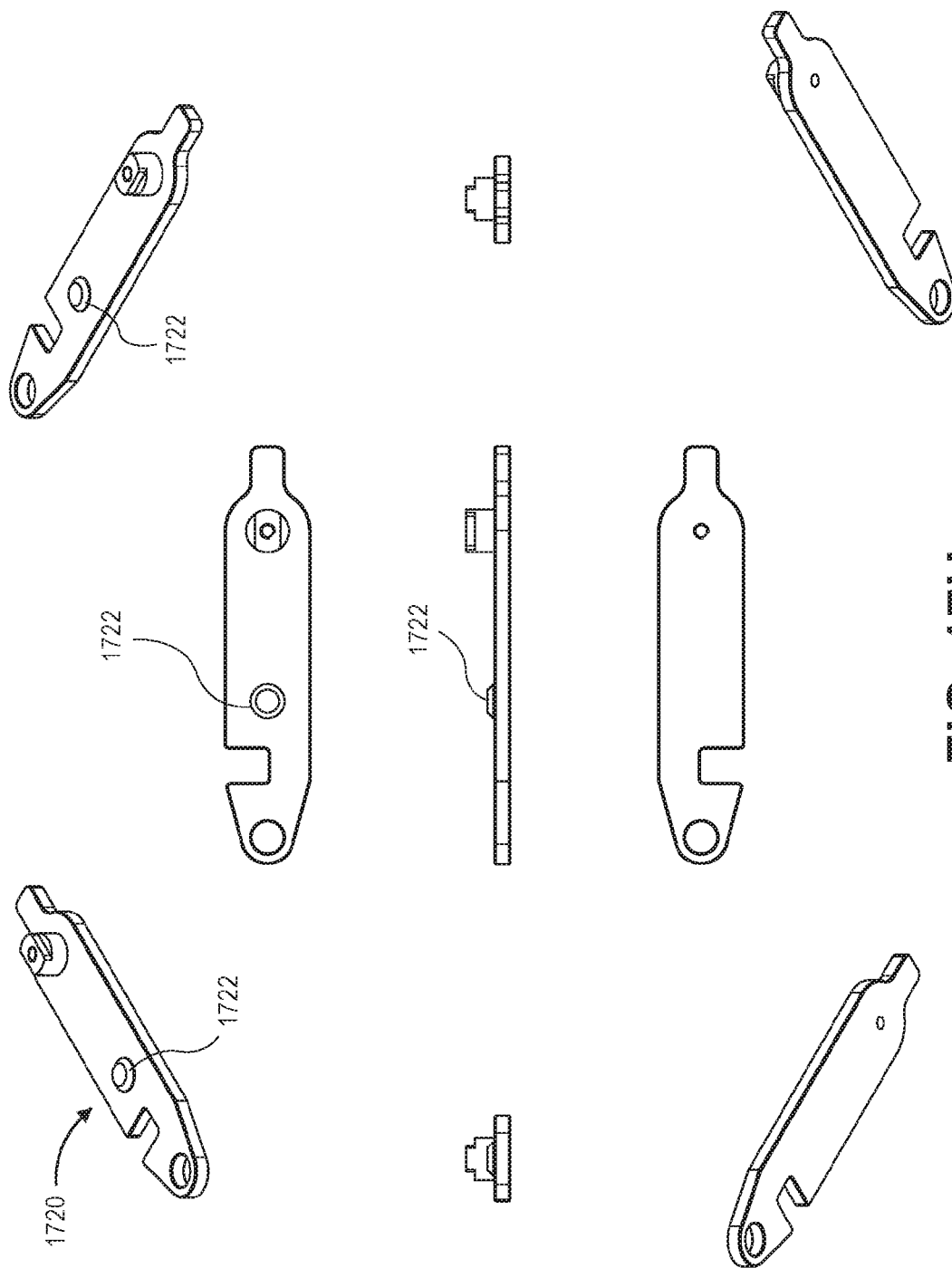

When the top arm 1730 and the spacer 1720 are positioned relative to one another as shown in FIG. 17D, top arm 1730 is spaced apart from spacer 1720 by bump feature 1722. In addition, when the top arm 1730 and the spacer 1720 are positioned relative to one another as shown in FIG. 17E, top arm 1730 is substantially not spaced apart from or contacts spacer 1720. This occurs because when the top arm 1730 and the spacer 1720 are positioned as shown in FIG. 17D, bump feature 1722 is not aligned with divot 1732 of top arm 1730, illustrated, for example in FIG. 17F. When not aligned, bump feature 1722 presses against top arm 1730 causing the separation of spacer 1720 and top arm 1730. In contrast, when the top arm 1730 and the spacer 1720 are positioned as shown in FIG. 17E, bump feature 1722 aligns with divot 1732 of top arm 1730 and prevents the top arm 1730 from rotating with respect to spacer 1720, and top arm 1730 and the spacer 1720 are near or in contact with one another as a result of a force applied by fastener 1750. In some embodiments, the same or similar result may be achieved with a bump feature in top arm 1730 and a corresponding divot in spacer 1720.

To insert a tumor into nsPEF pulse applicator 1700, top arm 1730 may be rotated such that top electrode 1735 is out of alignment with cavity 1725, and such that cavity 1725 is viewable, for example, as illustrated in FIG. 17C. A force may also be applied to bottom arm 1710 causing bottom arm 1710 to separate from spacer 1720 near cavity 1725, for example, as illustrated in FIG. 17C. The tumor may then be placed in the cavity 1725 such that tissue connecting the tumor with the patient is between bottom arm 1710 and spacer 1720. In some applications, the tumor is not connected to the subject, and the tumor is enclosed within cavity 1725.

An advantageous aspect of nsPEF pulse applicator 1700 is that while the tumor is placed in the cavity 1725, top arm 1730 is spaced apart from cavity 1725, and the cavity 1725 is viewable to visually confirm that the tumor is properly placed.

The applied force may then be removed such that bottom arm 1710 presses the connecting tissue against spacer 1720. The bottom arm 1710 presses the connecting tissue against spacer 1720 in response to the removal of the applied force because of a restorative force generated by the shape of the compliant top arm 1730 and the fastener 1750. In alternative embodiments, the bottom arm 1710 may press the connecting tissue against spacer 1720 in response to a force generated by a compression spring, for example between 1730 and bottom arm 1710 near or circumscribing fastener 1750.

An advantageous aspect of nsPEF pulse applicator 1700 is that while bottom arm 1710 is allowed to press the connecting tissue against spacer 1720, top arm 1730 is spaced apart from cavity 1725, and the cavity 1725 is viewable to visually confirm that the tumor is properly placed when secured by bottom arm 1710.

Top arm 1730 may then be rotated so as to align or substantially align top electrode 1735 with the cavity 1725 containing the tumor. As discussed above, when top arm 1730 is rotated, bump feature 1722 causes top arm 1730 to separate from spacer 1720 until top arm 1730 is at or near the desired alignment, where the top arm 1730 is pressed toward or against spacer 1720. In some embodiments, bump feature 1722 prevents the combination of top arm 1730 and spacer 1720 from generating shearing forces on any connecting tissue or tumor protruding from the cavity 1725, which could otherwise damage the protruding connecting tissue or tumor.

An advantageous aspect of nsPEF pulse applicator 1700 is that while top arm 1730 is rotated, the cavity 1725 is viewable to visually confirm that the tumor is properly placed during the rotation.

Once the tumor is inserted into the cavity 1725 and the top and bottom electrodes 1735 and 1715 are positioned, the nsPEF pulse applicator 1700 may be used to apply nsPEF pulses to the tumor by applying nsPEF pulses to the conductive wires 1740. In response to the nsPEF pulses applied to the wires, the top and bottom electrodes 1735 and 1715 generate an electric field across the cavity and therefore across the tumor within the cavity.

Once the nsPEF treatment is finished, the tumor may be removed from the nsPEF pulse applicator 1700 by applying a force to bottom arm 1710 causing bottom arm 1710 to separate from spacer 1720 near cavity 1725, for example, as illustrated in FIG. 17C, and removing the tumor.

In alternative embodiments, a bottom arm having features similar to bottom arm 1710 is spaced apart from a top arm having features similar to top arm 1730 by a spacer, such that without a force applied, the bottom and top arms are spaced apart from the spacer, and in response to a force applied thereto the bottom and top arms may be pressed against the spacer.

FIGS. 18A-18E schematically illustrate multiple views of an nsPEF pulse applicator 1800 which may, for example, be used as nsPEF pulse applicator 1565 in nsPEF treatment system 1550 of FIG. 15. NsPEF pulse applicator 1800 may have characteristics similar to or identical to any of the nsPEF pulse applicators discussed herein. For example, nsPEF pulse applicator 1800 may have characteristics similar to or identical to nsPEF pulse applicators 300, 400, and 1700 discussed above with reference to FIGS. 3, 4, and 17A-17H.

NsPEF pulse applicator 1800 includes bottom arm 1810, spacer 1820, and top arm 1830 rotatably connected by fastener 1850. Bottom arm 1810 includes bottom electrode 1815, which may be connected to a conductive wire at connection point 1822. Top arm 1830 includes top electrode 1835, which may be connected to a conductive wire at connection point 1833.

NsPEF pulse applicator 1800 is configured to receive nsPEF pulses from the conductive wires and to deliver nsPEF pulses to a patient or experiment subject undergoing nsPEF treatment through top and bottom electrodes 1835 and 1815. The nsPEF pulses may, for example, be applied to a tumor of the patient or experiment subject which is positioned within cavity 1825 of spacer 1820. Cavity 1825 forms a gap between top and bottom electrodes 1815 and 1835. In some applications, the tumor is connected to the patient or experiment subject by tissue which passes from the tumor within cavity 1825 to the patient or experiment subject between spacer 1820 and bottom arm 1810 or top arm 1830. In some embodiments, cavity 1825 is formed such that the gap between top and bottom electrodes 1815 and 1835 is open. For example, a portion of the gap may not be bounded by spacer 1820, top arm 1830, or bottom arm 1810.

Spacer 1820 includes top slot 1822 and bottom slot 1824. Slots 1822 and 1824 are positioned and sized so as to provide space, for example, for at least one of a wire and a solder connection to each of top electrode 1835 and bottom electrode 1815 when bottom electrode 1815, cavity 1825, and top electrode 1835 are aligned for example, as shown in the bottom two illustrations of FIG. 18A.

In the illustrated embodiment, bottom arm 1810 includes groove 1813, which is configured to accommodate a wire electrically connected with bottom electrode 1815 at connection point 1822 through a hole in bottom arm 1810. In some embodiments, a similar groove extends to the perimeter of bottom arm 1810, for example near fastener 1850. In some embodiments, top arm 1830 additionally or alternatively includes a similar groove configured to accommodate a wire electrically connected with the top electrode 1835 at connection point 1833 through a hole in the top arm 1830.

Figure 18A:
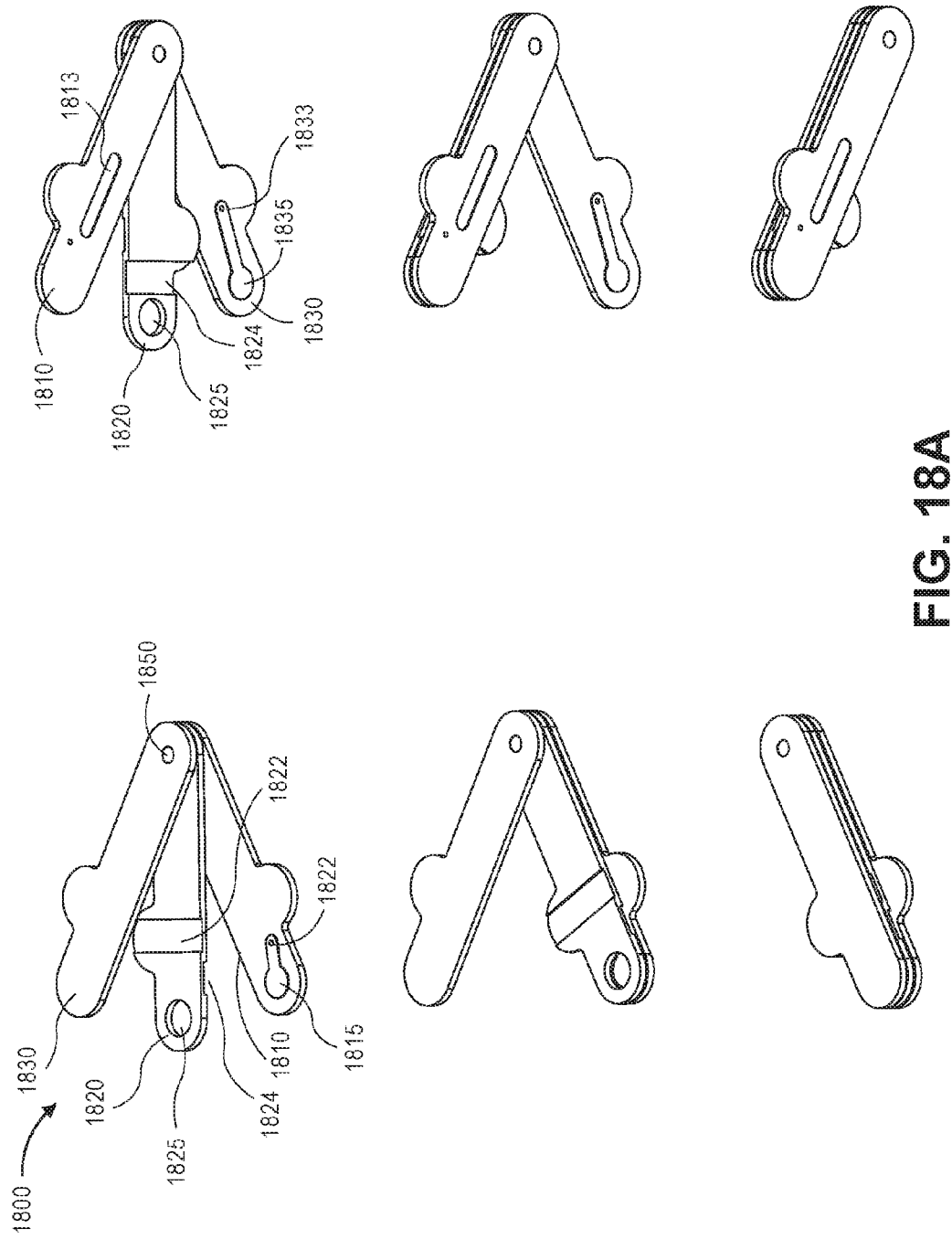
FIG. 18A-18E are schematic illustrations of various views of an nsPEF pulse applicator which may be used in the nsPEF treatment system of FIG. 15.
Figure 18B:
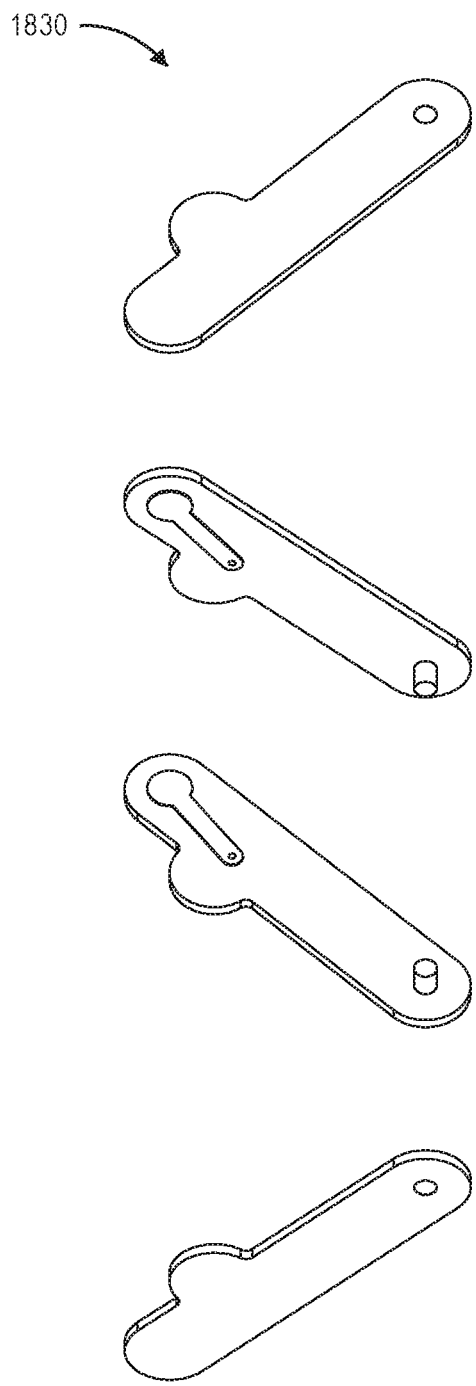
Figure 18C:
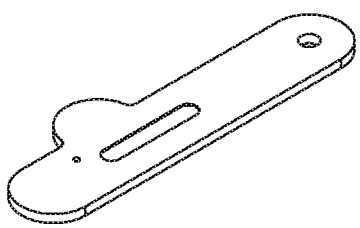
Figure 18C:
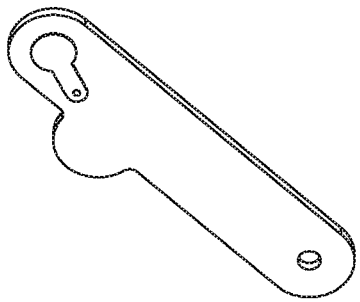
Figure 18C:
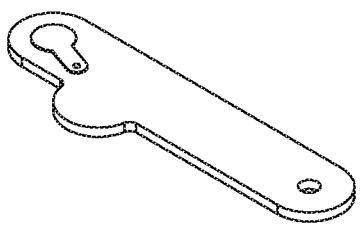
Figure 18C:
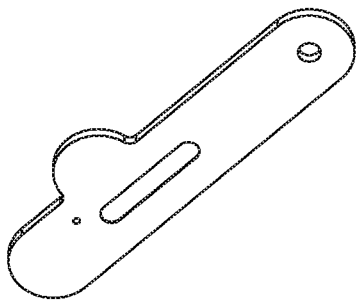
Figure 18D:
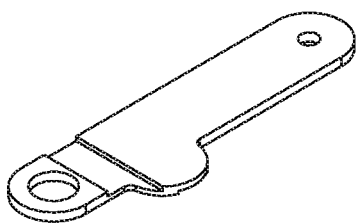
Figure 18D:
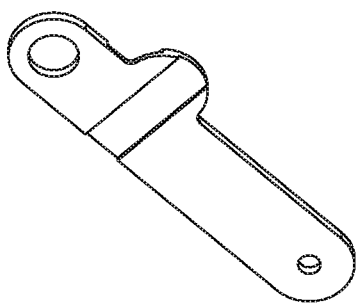
Figure 18D:
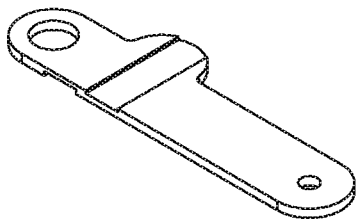
Figure 18D:
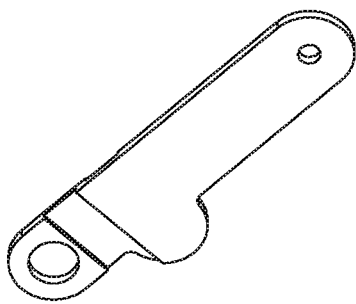
Figure 18E:
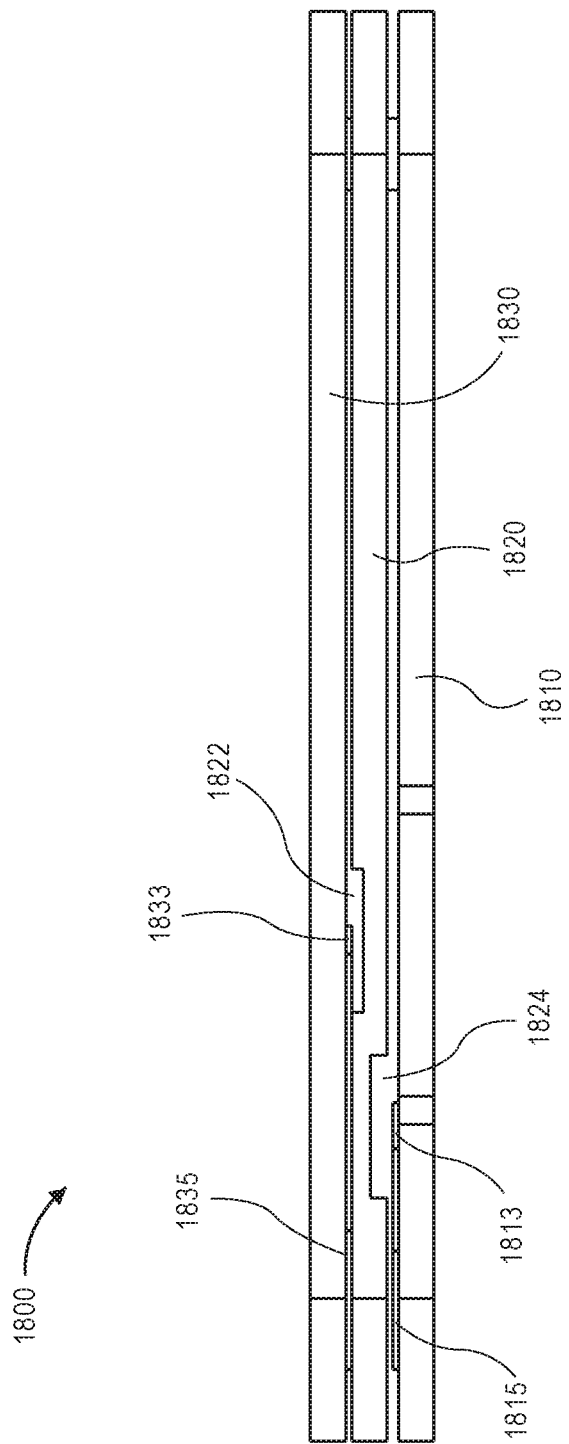

To insert a tumor into nsPEF pulse applicator 1800, top arm 1830 may be rotated such that top electrode 1835 is out of alignment with cavity 1825, and such that cavity 1825 is viewable, for example, as illustrated in the vertically central illustrations of FIG. 18A. Bottom arm 1810 may be rotated such that bottom electrode 1815 is similarly out of alignment with cavity 1825. The tumor may then be placed in the cavity 1825 such that tissue connecting the tumor with the patient is between bottom arm 1810 and spacer 1820.

An advantageous aspect of nsPEF pulse applicator 1800 is that while the tumor is placed in the cavity 1825, top arm 1830 is spaced apart from cavity 1825, and the cavity 1825 is viewable to visually confirm that the tumor is properly placed.

Bottom arm 1810 may then be rotated so as to align or substantially align bottom electrode 1815 with the cavity 1825. In this configuration, bottom arm 1810 securely presses the connecting tissue against spacer 1820. In some applications, the tumor is not connected to the subject, and the tumor is enclosed within cavity 1825.

An advantageous aspect of nsPEF pulse applicator 1800 is that while bottom arm 1810 is allowed to press the connecting tissue against spacer 1820, top arm 1830 is spaced apart from cavity 1825, such that the cavity 1825 is viewable to visually confirm that the tumor is properly placed when secured by bottom arm 1810.

Once inserted, the nsPEF pulse applicator 1800 may be used to apply nsPEF pulses to the tumor by applying nsPEF pulses to the conductive wires.

Once the nsPEF treatment is finished, the tumor may be removed from the nsPEF pulse applicator 1800 by rotating the top or bottom arm 1810 or 1830 pressing the connecting tissue against spacer 1820, and removing the tumor. The other of top and bottom arm 1810 and 1830 may also be rotated.

FIGS. 19A-19F schematically illustrate multiple views of an nsPEF pulse applicator 1900 which may, for example, be used as nsPEF pulse applicator 1565 in nsPEF treatment system 1550 of FIG. 15. NsPEF pulse applicator 1900 may have characteristics similar to or identical to any of the nsPEF pulse applicators discussed herein. For example, nsPEF pulse applicator 1900 may have characteristics similar to or identical to nsPEF pulse applicators 300 and 400 discussed above with reference to FIGS. 3 and 4.

NsPEF pulse applicator 1900 includes bottom arm 1910, spacer 1920, and top arm 1930 rotatably connected together so as to rotate about pivot points 1912, one of which is illustrated in each of FIGS. 19A, 19B, and 19C. Bottom arm 1910 includes bottom electrode 1915, which is connected to one of the conductive wires 1940. Top arm 1930 includes top electrode 1935, which is connected to the other of the conductive wires 1940.

NsPEF pulse applicator 1900 is configured to receive nsPEF pulses across conductive wires 1940 and to deliver nsPEF pulses to a patient or experiment subject undergoing nsPEF treatment through top and bottom electrodes 1915 and 1935. The nsPEF pulses may, for example, be applied to a tumor of the patient or experiment subject which is positioned within cavity 1925 of spacer 1920. Cavity 1925 forms a gap between top and bottom electrodes 1915 and 1935. In some applications, the tumor is connected to the patient or experiment subject by tissue which passes from the tumor within cavity 1925 to the patient or experiment subject between spacer 1920 and bottom arm 1910. In some embodiments, cavity 1925 is formed such that the gap between top and bottom electrodes 1915 and 1935 is open. For example, a portion of the gap may not be bounded by spacer 1920, top arm 1930, or bottom arm 1910.

As shown in FIG. 19A, bottom arm 1910 is separated from top arm 1930 by spacer 1920 near cavity 1925. In addition, each of bottom arm 1910, spacer 1920, and top arm 1930 are rotatable about pivot point 1912.

In FIG. 19B, nsPEF pulse applicator 1900 is illustrated as if an external force is applied to top arm 1930 causing top electrode 1935 of top arm 1930 to be separated from spacer 1920 near cavity 1925.

In FIG. 19A, nsPEF pulse applicator 1900 is illustrated as if the external force is not applied to top arm 1930. As a result, top electrode 1935 of top arm 1930 is near spacer 1920 in the region close to cavity 1925, as illustrated in FIG. 19A. If no external force is applied causing top arm 1930 to be separated from spacer 1920 near cavity 1925, top arm 1930 is pressed against spacer 1920 by a force exerted by a first torsion spring 1932.

As illustrated in FIGS. 19B and 19C, top arm 1930 is held in place by detent mechanism 1937, which is configured to engage divot 1929 so as to prevent the first torsion spring 1932 from pressing top arm 1930 against spacer 1920. Other mechanisms may alternatively be used to prevent the first torsion spring 1932 from pressing top arm 1930 against spacer 1920.

As shown in FIG. 19C, nsPEF pulse applicator 1900 is illustrated as if an external force is applied to bottom arm 1910 causing bottom electrode 1915 of bottom arm 1910 to be separated from spacer 1920 near cavity 1925.

In FIG. 19A, nsPEF pulse applicator 1900 is illustrated as if the external force is not applied to bottom arm 1910. As a result, bottom electrode 1915 of bottom arm 1910 is near spacer 1920 in the region close to cavity 1925, as illustrate in FIG. 19A. If no external force is applied causing bottom arm 1910 to be from spacer 1920 near cavity 1925, bottom arm 1910 is pressed against spacer 1920 in the region close to cavity 1925 by a force exerted by a second torsion spring 1938.

Figure 19D:
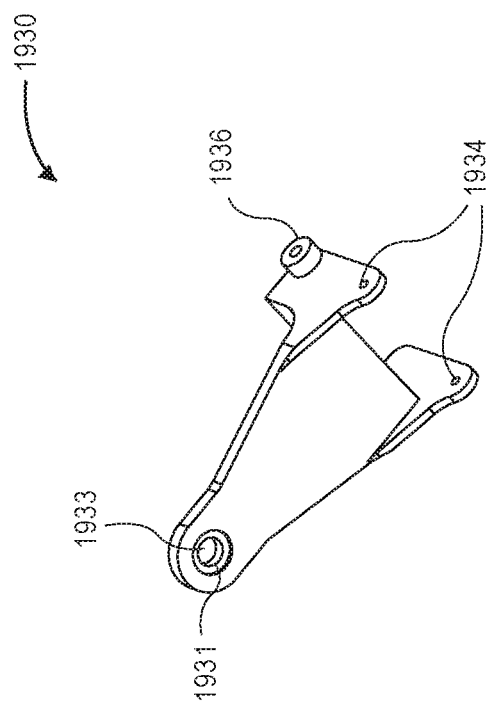

FIG. 19D is a schematic illustration of top arm 1930 isolated from the other components of nsPEF pulse applicator 1900.

Top arm 1930 includes cavity 1931, which is configured to receive and hold electrode 1935, where the wire 1940 attached to electrode 1935 passes through hole 1933.

Top arm 1930 also includes holes 1934, each configured to receive an axle such that top arm 1930 is configured to rotate about pivot point 1912 by rotating about the axle. In some embodiments, the axle comprises a pin. In alternative embodiments, the axle comprises a spring bar. In some embodiments, the axle comprises two colinear axle components.

Top arm 1930 also includes detent holder 1936, which holds a detent mechanism 1937 configured to engage divot 1929 of spacer 1920 so as to prevent the first torsion spring 1932 from pressing top arm 1930 against spacer 1920. In alternative embodiments, other mechanisms are used to prevent the first torsion spring 1932 from pressing top arm 1930 against spacer 1920. For example, a bump/divot combination, similar to those discussed elsewhere herein may be used. In some of such embodiments, the divot of such a combination is in top arm 1930. In alternative embodiments, the bump of such a combination is formed in top arm 1930.

Figure 19E:
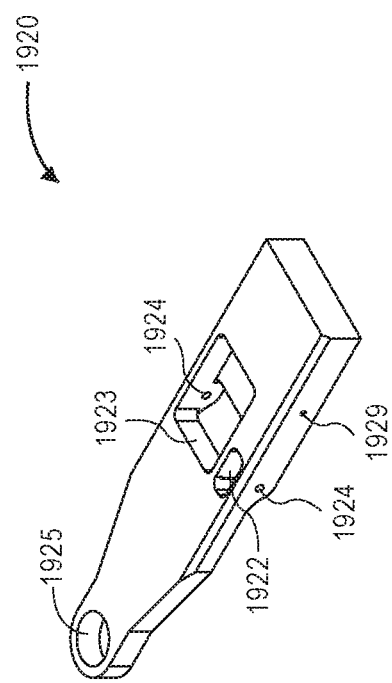

FIG. 19E is a schematic illustration of spacer 1920 isolated from the other components of nsPEF pulse applicator 1900.

Spacer 1920 includes a through hole, which forms cavity 1925, which, as discussed below, is configured to contain tissue receiving nsPEF pulses from nsPEF pulse applicator 1900.

Spacer 1920 also includes first and second cavities 1923 and 1922, which are respectively configured to receive first and second torsion springs 1932 and 1938 discussed above.

Spacer 1920 also includes holes 1924, each configured to receive an axle such that spacer 1920 is configured to rotate about pivot point 1912 by rotating about the axle. In some embodiments, the axle comprises a pin. In alternative embodiments the axle comprises a spring bar. In some embodiments, the axle comprises two colinear axle components.

Spacer 1920 also includes the divot 1929, configured to engage a detent in top arm 1930 so as to prevent the first torsion spring 1932 from pressing top arm 1930 against spacer 1920. In alternative embodiments, other mechanisms are used to prevent the first torsion spring 1932 from pressing top arm 1930 against spacer 1920. For example, a bump/divot combination, similar to those discussed elsewhere herein may be used. In some of such embodiments, the divot of such a combination is in spacer 1920. In alternative embodiments, the bump of such a combination is formed in spacer 1920.

Figure 19F:
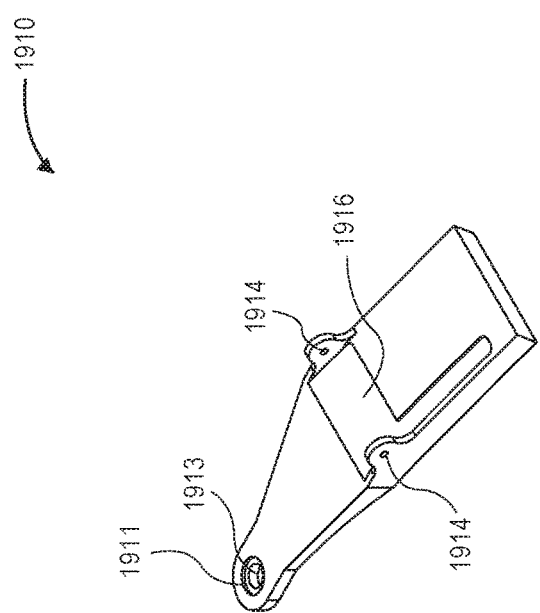

FIG. 19F is a schematic illustration of bottom arm 1910 isolated from the other components of nsPEF pulse applicator 1900.

Bottom arm 1910 includes cavity 1911, which is configured to receive and hold electrode 1915, where the wire 1940 attached to electrode 1915 passes through hole 1913.

Bottom arm 1910 also includes holes 1914, each configured to receive an axle such that bottom arm 1910 is configured to rotate about pivot point 1912 by rotating about the axle. In some embodiments, the axle comprises a pin. In alternative embodiments the axle comprises a spring bar. In some embodiments, the axle comprises two colinear axle components.

Bottom arm 1910 also includes feature 1916, which is configured to be engaged by the second torsion spring 1938, such that bottom arm 1910 is pressed against spacer 1920 in the region close to cavity 1925 by a force exerted by the second torsion spring 1938.

To insert a tumor into nsPEF pulse applicator 1900, top arm 1930 may be rotated about pivot point 1912 such that top electrode 1935 is held in place by detent mechanism 1937 and such that cavity 1925 is viewable, as illustrated in FIGS. 19B and 19C. To rotate top arm 1930 about pivot point 1912, a force is applied to top arm 1930 which overcomes the force applied to top arm 1930 by the first torsion spring 1932.

In addition, bottom arm 1910 is rotated about pivot point 1912 such that bottom electrode 1915 is spaced apart from cavity 1925 in spacer 1920, as illustrated in FIG. 19C. To rotate bottom arm 1910 about pivot point 1912, a force is applied to bottom arm 1910 which overcomes the force applied to bottom arm 1910 by the second torsion spring 1938.

The tumor may then be placed in the cavity 1925 such that tissue connecting the tumor with the patient is between bottom arm 1910 and spacer 1920.

An advantageous aspect of nsPEF pulse applicator 1900 is that while the tumor is placed in the cavity 1925, top arm 1930 is spaced apart from cavity 1925, and the cavity 1925 is viewable to visually confirm that the tumor is properly placed.

Bottom arm 1910 may then be rotated so as to press the connecting tissue against spacer 1920 and to place electrode 1915 adjacent to cavity 1925, as illustrated in FIGS. 19A and 19B. In this configuration, the tumor is securely held within cavity 1925. In some applications, the tumor is not connected to the subject, and the tumor is enclosed within cavity 1925.

An advantageous aspect of nsPEF pulse applicator 1900 is that while bottom arm 1910 is rotated to press the connecting tissue against spacer 1920, top arm 1930 is spaced apart from cavity 1925, and the cavity 1925 is viewable to visually confirm that the tumor is properly placed when secured by the rotation of bottom arm 1910.

Top arm 1930 may then be rotated so as to place top electrode 1935 adjacent the cavity 1925 containing the tumor, as illustrated in FIGS. 19A and 19B.

Once inserted, the nsPEF pulse applicator 1900 may be used to apply nsPEF pulses to the tumor by applying nsPEF pulses to the conductive wires.

Once the nsPEF treatment is finished, the tumor may be removed from the nsPEF pulse applicator 1900 by rotating the bottom arm 1910 pressing the connecting tissue against spacer 1920, as illustrated in FIG. 19C, and removing the tumor. The top arm 1930 may also be rotated, as illustrated in FIGS. 19B and 19C, to allow visual inspection of the removal of the tumor.

FIGS. 20A-20G schematically illustrate multiple views of an nsPEF pulse applicator 2000 which may, for example, be used as nsPEF pulse applicator 1565 in nsPEF treatment system 1550 of FIG. 15. NsPEF pulse applicator 2000 may have characteristics similar to or identical to any of the nsPEF pulse applicators discussed herein. For example, nsPEF pulse applicator 2000 may have characteristics similar to or identical to other nsPEF pulse applicators discussed herein.

NsPEF pulse applicator 2000 includes bottom arm 2010, spacer 2020, and top arm 2030.

NsPEF pulse applicator 2000 is configured to receive nsPEF pulses and to deliver nsPEF pulses to a patient or experiment subject undergoing nsPEF treatment through top and bottom electrodes 2015 and 2035. The nsPEF pulses may, for example, be applied to a tumor of the patient or experiment subject which is positioned within cavity 2025 of spacer 2020. Cavity 2025 forms a gap between top and bottom electrodes 2015 and 2035. In some applications, the tumor is connected to the patient or experiment subject by tissue which passes from the tumor within cavity 2025 to the patient or experiment subject between spacer 2020 and bottom arm 2010. In some embodiments, cavity 2025 is formed such that the gap between top and bottom electrodes 2015 and 2035 is open. For example, a portion of the gap may not be bounded by spacer 2020, top arm 2030, or bottom arm 2010.

Figure 20A:
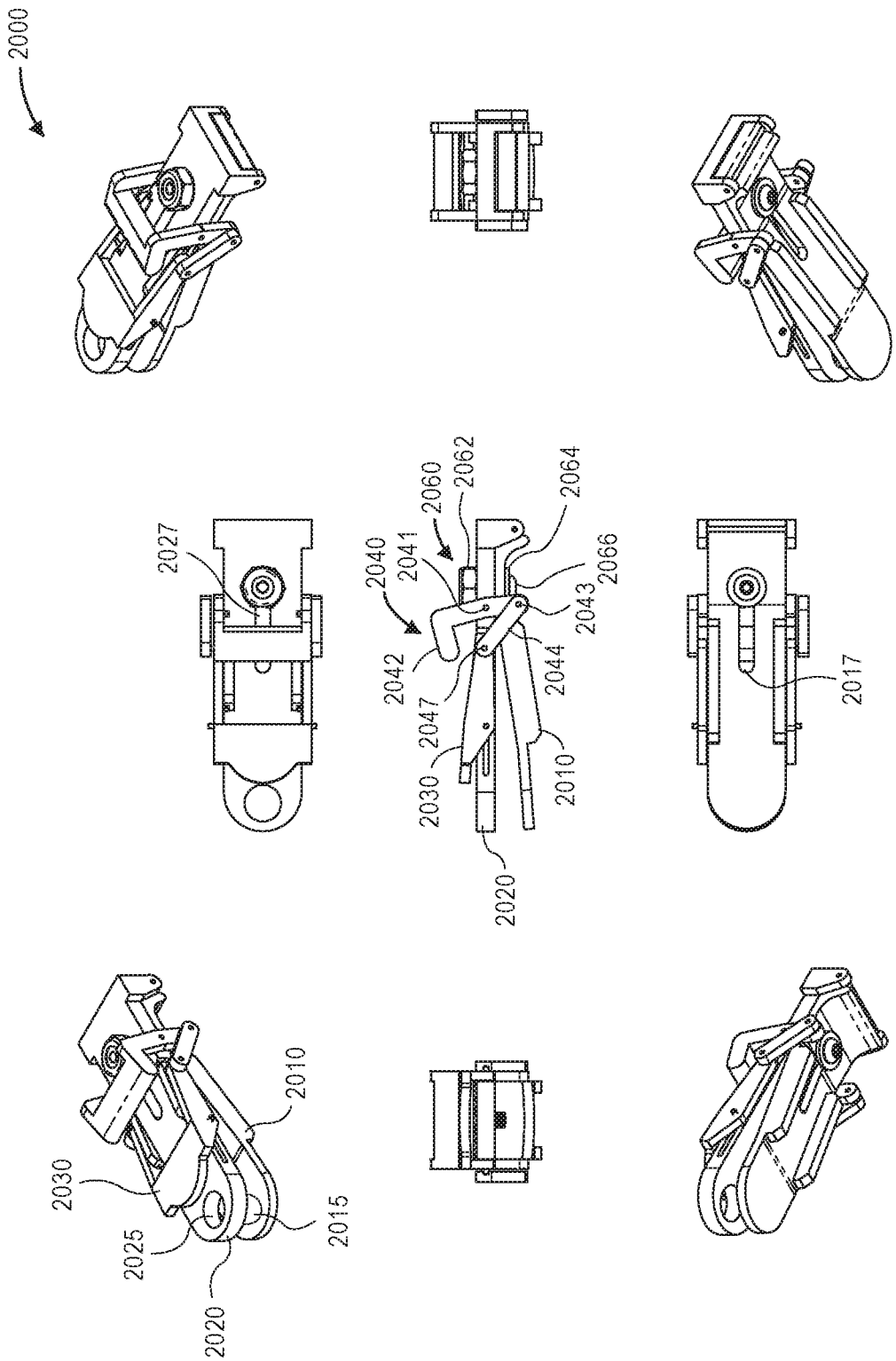
FIG. 20A-20G are schematic illustrations of various views of an nsPEF pulse applicator which may be used in the nsPEF treatment system of FIG. 15.
Figure 20B:
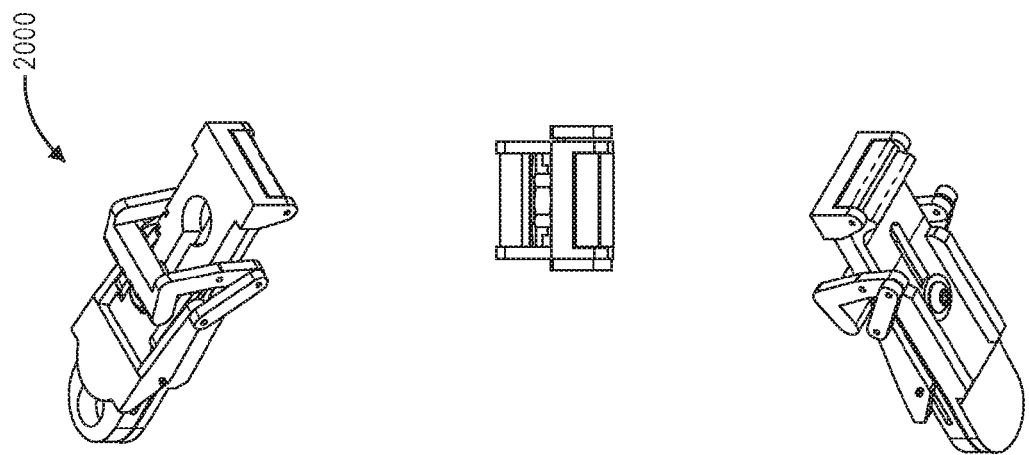
Figure 20B:
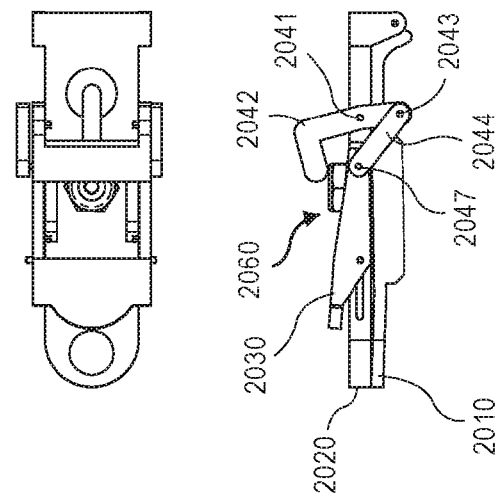
Figure 20B:
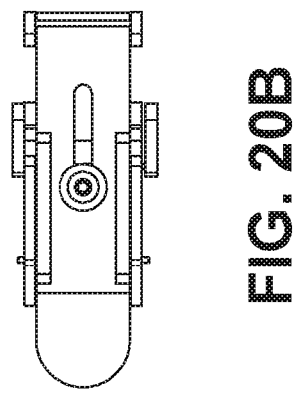
Figure 20B:
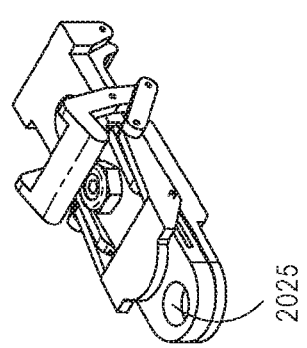
Figure 20B:
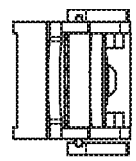
Figure 20B:
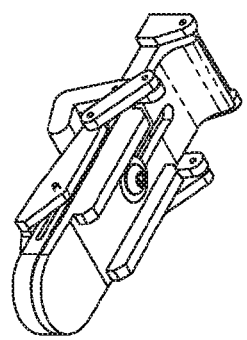

Bottom arm 2010 and spacer 2020 are movably connected to one another such that bottom arm 2010 and spacer 2020 may be positioned relative to one another in configurations shown in FIGS. 20A and 20B. Bottom arm 2010 includes bottom electrode 2015, which is positioned so as to be selectively adjacent cavity 2025 of spacer 2020 according to the relative position of bottom arm 2010 and spacer 2020.

In FIG. 20A, NsPEF pulse applicator 2000 is illustrated with bottom arm actuator 2060 positioned so as to cause bottom electrode 2015 of bottom arm 2010 to be separated from spacer 2020 near cavity 2025. In contrast, in FIGS. 20B and 20C, NsPEF pulse applicator 2000 is illustrated with bottom arm actuator 2060 positioned so as to cause bottom electrode 2015 of bottom arm 2010 to be adjacent spacer 2020 near cavity 2025. As a result, bottom electrode 2015 of bottom arm 2010 is near spacer 2020 in the region close to cavity 2025.

Bottom arm 2010 may be moved between the positions shown in FIGS. 20A and 20B with bottom arm actuator 2060. In this embodiment, bottom arm actuator 2060 includes nut 2062, washer 2064, and screw 2066. Screw 2066 passes through bottom arm 2010 through bottom slot 2017. In addition, screw 2066 passes through spacer 2020 through slot 2027.

In the configuration illustrated in FIG. 20A, bottom arm actuator 2060 is positioned so that the bottom electrode 2015 is spaced apart from cavity 2025 of spacer 2020. In the configuration illustrated in FIG. 20B, bottom arm actuator 2060 is positioned so that the bottom electrode 2015 is adjacent to cavity 2025 of spacer 2020. So that nsPEF pulse applicator 2000 is adjustable between the configurations illustrated in FIGS. 20A and 20B, bottom arm actuator 2060 is configured to slide along bottom slot 2017 of bottom arm 2010 and slot 2027 of spacer 2020 in response to a force applied thereto, for example, by a thumb of a user.

In the configuration illustrated in FIG. 20A, surface 2012 (illustrated in FIG. 20G) of bottom arm 2010 presses against or faces spacer 2020 because of the position of bottom arm actuator 2060. In the configuration illustrated in FIG. 20B, surface 2014 (illustrated in FIG. 20G) of bottom arm 2010 presses against or faces spacer 2020 because of the position of bottom arm actuator 2060. Because surfaces 2012 and 2014 are angled, the distance of bottom arm 2010 to cavity 2025 of spacer 2020 is dependent on the position of bottom arm actuator 2060.

Figure 20C:
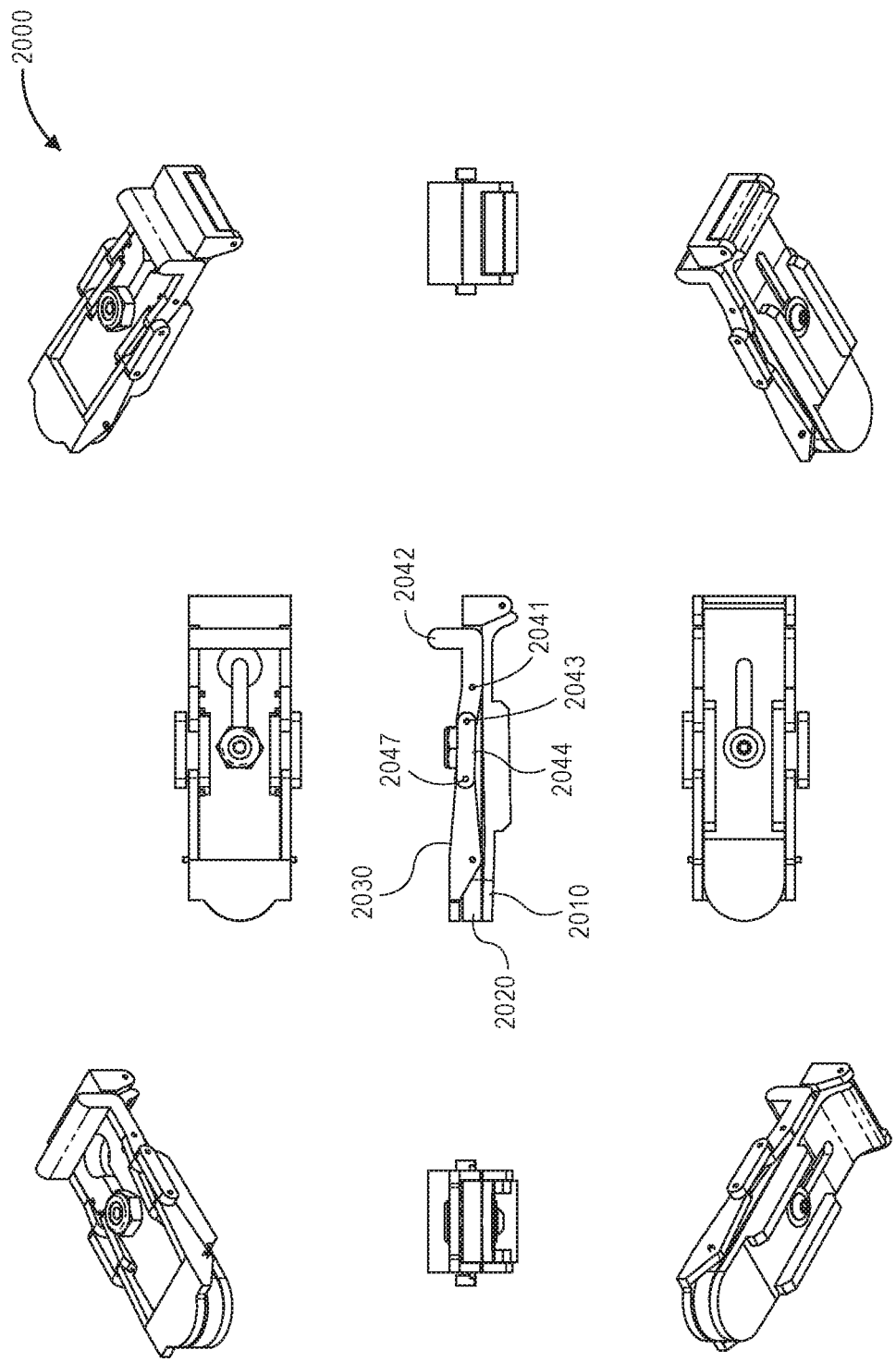

Top arm 2030 and spacer 2020 are movably connected to one another such that top arm 2030 and spacer 2020 may be positioned relative to one another in configurations shown in FIGS. 20B and 20C. Top arm 2030 includes top electrode 2035, which is illustrated in FIG. 2E. Top electric 2035 is positioned on top arm 2030 such that when top arm 2030 and spacer 2020 are positioned in the configurations shown in FIGS. 20A and 20B, top electrode 2035 is spaced apart from cavity 2025 in spacer 2020. In contrast, when top arm 2030 and spacer 2020 are positioned in the configuration shown in FIG. 20C, top electrode 2035 is adjacent to cavity 2025.

In FIGS. 20A and 20B, NsPEF pulse applicator 2000 is illustrated as if an external force is or has been applied to handle 2042 causing top electrode 2035 of top arm 2030 to be separated from spacer 2020 near cavity 2025. In contrast, in FIG. 20C, NsPEF pulse applicator 2000 is illustrated as if an external force is or has been applied to handle 2042 causing top electrode 2035 of top arm 2030 to be adjacent spacer 2020 near cavity 2025. As a result, top electrode 2035 of top arm 2030 is near spacer 2020 in the region close to cavity 2025.

Top arm 2030 may be moved between the positions shown in FIGS. 20B and 20C with top arm actuator 2040. In this embodiment, top arm actuator 2040 includes handle 2042 and linkage 2044.

Handle 2042 of top arm actuator 2040 is rotatably connected to spacer 2020 at pivot point 2041. Linkage 2044 is rotatably connected to top arm 2030 at pivot point 2047. In addition, handle 2042 is rotatably connected to linkage 2044 at pivot point 2043.

In the configuration illustrated in FIG. 20B, top arm actuator 2040 is positioned so that the top electrode 2035 is spaced apart from cavity 2025 of spacer 2020. In the configuration illustrated in FIG. 20C, top arm actuator 2040 is positioned so that the top electrode 2035 is adjacent to cavity 2025 of spacer 2020. So that nsPEF pulse applicator 2000 is adjustable between the configurations illustrated in FIGS. 20B and 20C, handle 2042 of top arm actuator 2040 is configured to rotate about pivot point 2041 in response to a force applied thereto, for example, by a thumb of a user.

In the configuration illustrated in FIG. 20B, handle 2042 of top arm actuator 2040 has been moved to an "open" position in response to a force applied thereto. A portion of the force applied to handle 2042 is translated to top arm 2030 through linkage 2044. The portion of the force translated to top arm 2030 causes top arm 2030 to slide away from cavity 2025 of spacer 2020. In addition, the portion of the force translated to top arm 2030 causes top arm 2030 to rotate such that a gap between top electrode 2035 and spacer 2020 increases.

In the configuration illustrated in FIG. 20C, handle 2042 of top arm actuator 2040 has been moved to a "closed" position in response to a force applied thereto. A portion of the force applied to handle 2042 is translated to top arm 2030 through linkage 2044. The portion of the force translated to top arm 2030 causes top arm 2030 to slide toward cavity 2025 of spacer 2020 such that top electrode 2035 is adjacent cavity 2025 of spacer 2020. In addition, the portion of the force translated to top arm 2030 causes top arm 2030 to rotate such that a gap between top electrode 2035 and spacer 2020 decreases. In the configuration illustrated in FIG. 20C, handle 2042 has been rotated such that linkage 2044, connected to handle 2042 at pivot point 2043, has been moved to an "over center" position. Accordingly, in the configuration illustrated in FIG. 20C, handle 2042 prevents incidental forces experienced by top arm 2030 from displacing top arm 2030.

Figure 20D:
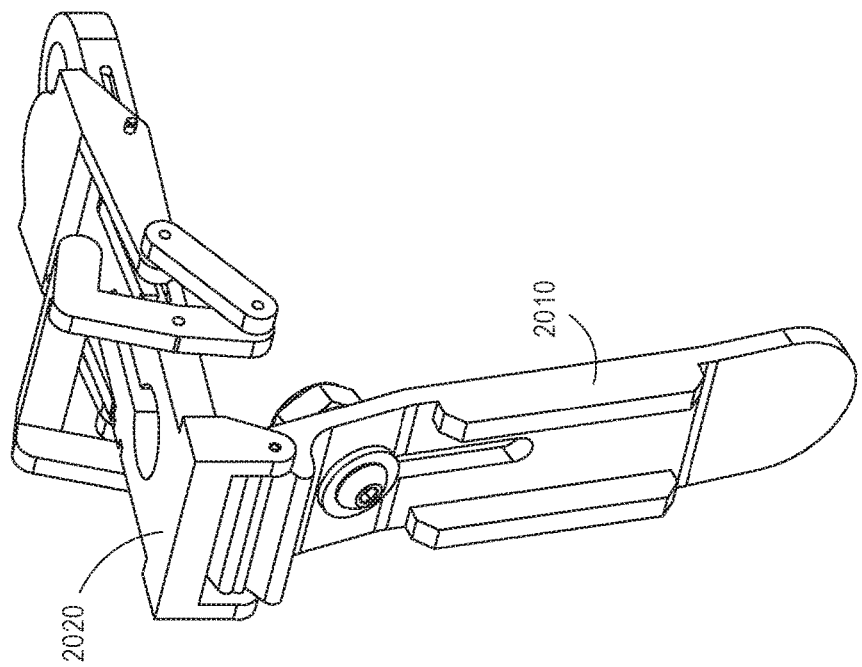
Figure 20D:
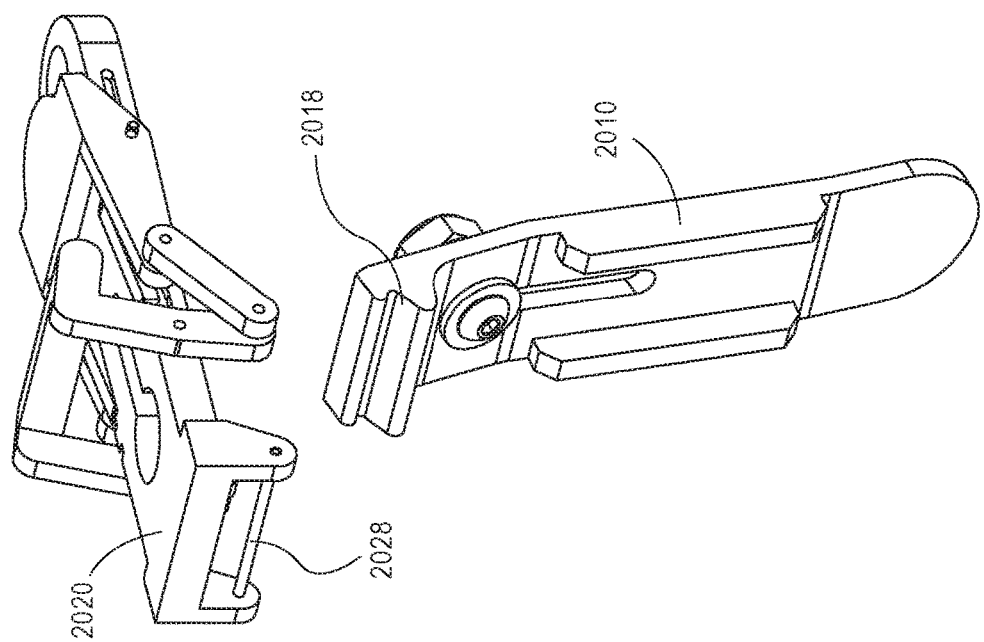

FIG. 20D illustrates an embodiment of a connection mechanism used to connect bottom arm 2010 to spacer 2020. As shown, spacer 2020 has pin 2028, which engages notch 2018. Notch 2018 is shaped such that when bottom arm 2010 engages spacer 2020 with an angle greater than a minimum, the bottom of notch 2018 is exposed to pin 2028. In addition, once notch 2018 engages pin 2028, and bottom arm 2010 is rotated relative to spacer 2020 such that the angle between bottom arm 2010 and spacer 2020 is less than a maximum, pin 2028 prevents separation of bottom arm 2010 and spacer 2020. An advantageous aspect of this connection mechanism is that bottom arm 2010 and spacer 2020 are assembleable and disassembleable by hand, without any tools, for example, for cleaning.

Figure 20E:
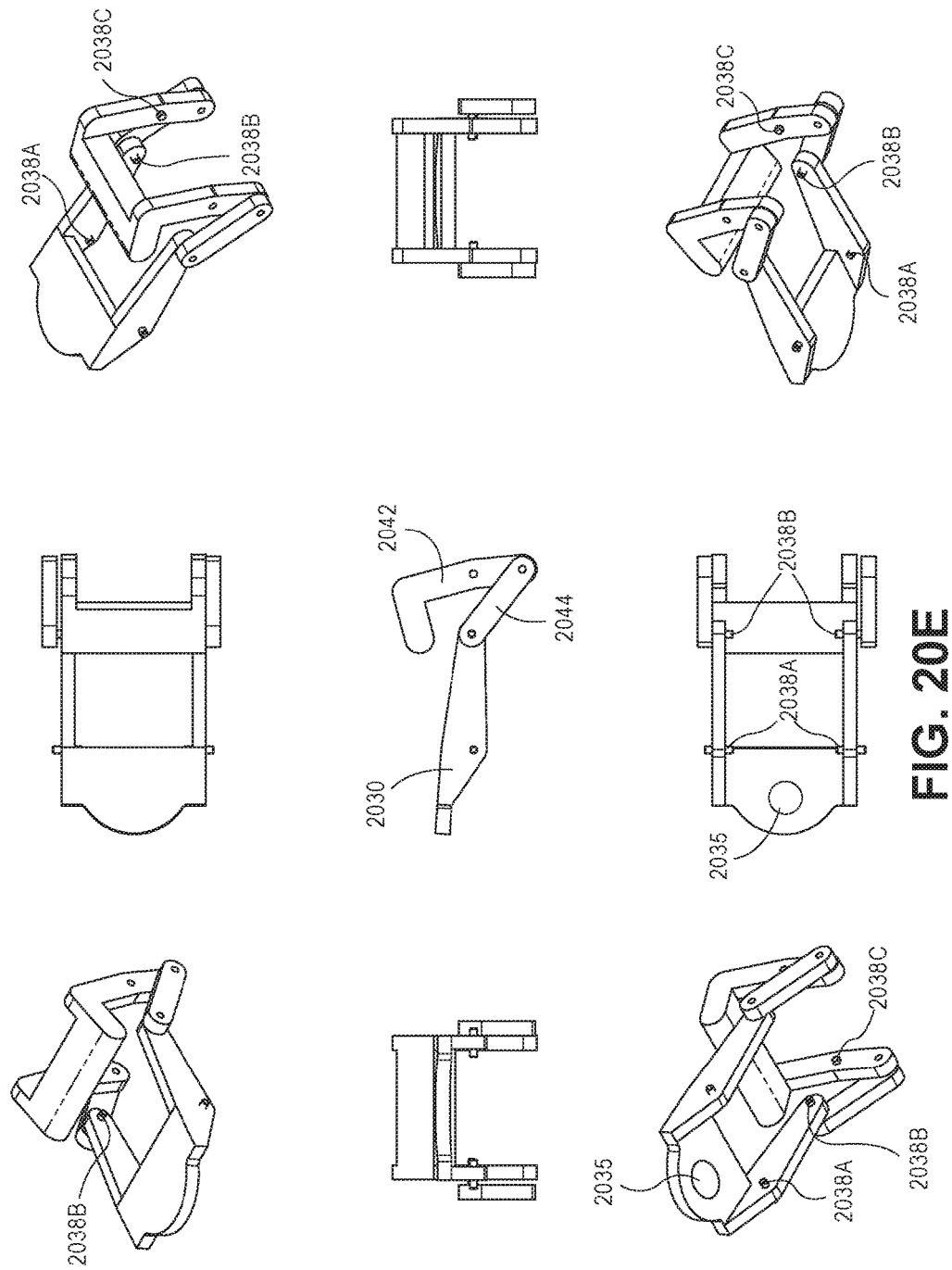

FIG. 20E is a schematic illustration of top arm 2030, linkage 2044, and handle 2042 isolated from the other components of nsPEF pulse applicator 2000.

Top arm 2030 includes posts 2038A, which engage slots 2021A of spacer 2020. When top arm 2030 is moved with respect to spacer 2020 with top arm actuator 2040, posts 2038A slide along slots 2021A.

Top arm 2030 includes posts 2038B, which engage slots 2021B of spacer 2020. When top arm 2030 is moved with respect to spacer 2020 with top arm actuator 2040, posts 2038A slide along slots 2021A. Because slot 2021B of spacer 2020 is angled with respect to slot 2021A of spacer 2020, when top arm 2030 is moved with respect to spacer 2020, the movement includes a linear motion and a rotation of top arm 2030 with respect to spacer 2020. An advantageous aspect of the rotation is that when top arm 2030 is moved to place top electrode 2035 adjacent cavity 2425, the rotation reduces or eliminates shearing forces experienced by the tumor as a result of the movement.

Handle 2042 includes posts 2038C, which engage slots 2021C of spacer 2020. When handle 2042 is moved to the position illustrated in FIG. 20B, posts 2038C engage slots 2021C such that handle 2042 is held in place by slots 2021C, and such that posts 2038C form the pivot point 2041, discussed above.

Top arm 2030 is rotatably connected to linkage 2044. In some embodiments, one or more posts fixed to top arm 2030 protrude from top arm 2030 into holes in linkage 2044. In alternative embodiments, one or more posts fixed to linkage 2044 protrude from linkage 2044 into holes in top arm 2030.

Handle 2042 is rotatably connected to linkage 2044. In some embodiments, one or more posts fixed to handle 2042 protrude from handle 2042 into holes in linkage 2044. In alternative embodiments, one or more posts fixed to linkage 2044 protrude from linkage 2044 into holes in handle 2042.

Figure 20F:
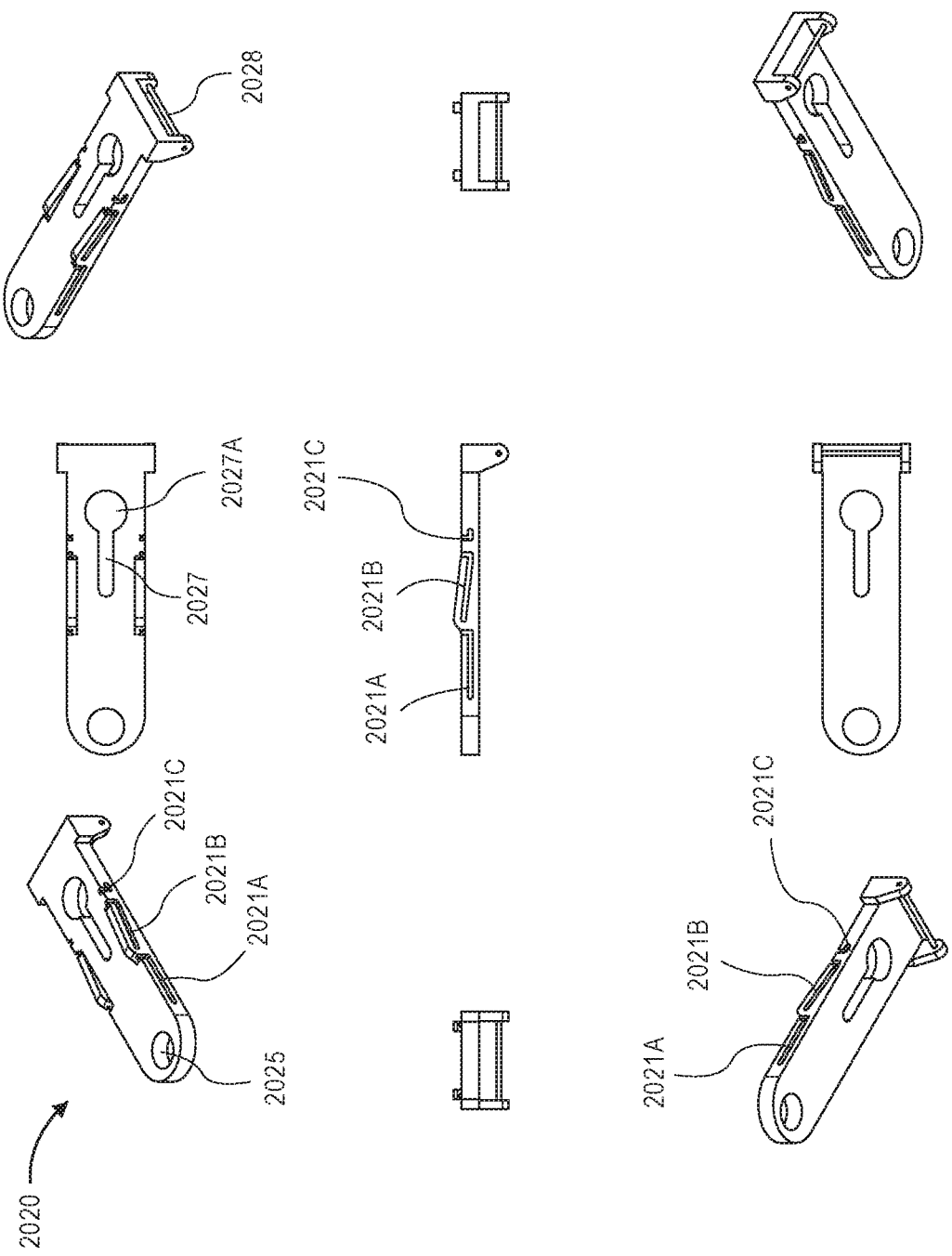
Figure 20G:
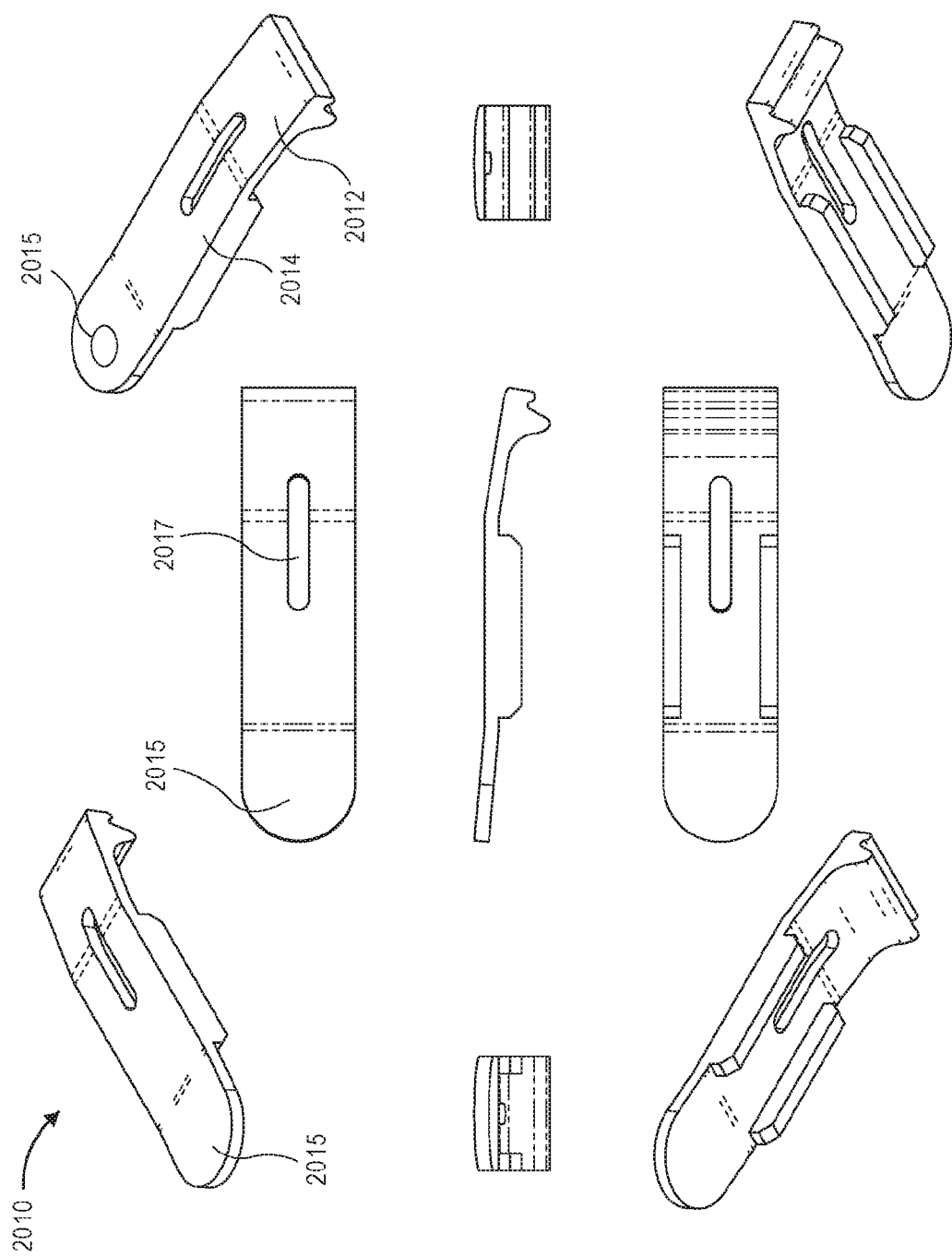

FIG. 20F is a schematic illustration of spacer 2020 isolated from the other components of nsPEF pulse applicator 2000.

Spacer 2020 includes a through hole, which forms cavity 2025, which, as discussed below, is configured to contain tissue receiving nsPEF pulses from nsPEF pulse applicator 2000.

Spacer 2020 also includes slot 2027, which has opening 2027A. Opening 2027A is larger than nut 2062 so that nut 2062 can pass through opening 2027A when bottom arm 2010 is connected to spacer 2020, as discussed above with reference to FIG. 20D.

Slots 2021A, 2021B, and 2021C, and pin 2028 are illustrated and are discussed elsewhere herein. An advantageous aspect of this connection mechanism using slots and pins is that top arm 2030 and spacer 2020 are assembleable and disassembleable by hand, without any tools, for example, for cleaning.

To insert a tumor into nsPEF pulse applicator 2000, top arm 2030 may be positioned so as to expose cavity 2025 of spacer 2020, as illustrated in FIG. 20A. To position top arm 2030 for tumor insertion, handle 2042 is moved to the position illustrated in FIG. 20A.

In addition, bottom arm 2010 is positioned so as to be spaced apart from spacer 2020 in the region near cavity 2025, as illustrated in FIG. 20A. To position bottom arm 2010 for tumor insertion, bottom arm actuator 2060 is moved to the position indicated in FIG. 20A.

The tumor may then be placed in the cavity 2025 such that tissue connecting the tumor with the patient is between bottom arm 2010 and spacer 2020. An advantageous aspect of bottom arm actuator 2060 is that bottom arm actuator 2060 does not apply a restorative force urging bottom electrode 2015 toward cavity 2025. Because of this advantage, the user need not apply a force to overcome the restorative force while inserting the tumor into cavity 2025.

An advantageous aspect of nsPEF pulse applicator 2000 is that while the tumor is placed in the cavity 2025, top arm 2030 is spaced apart from cavity 2025 such that cavity 2025 is viewable to visually confirm that the tumor is properly placed.

Bottom arm 2010 may then be positioned so as to press the connecting tissue against spacer 2020 and to place electrode 2015 adjacent to cavity 2025. To position bottom arm 2010 to hold the tumor, bottom arm actuator 2060 is moved to the position indicated in FIG. 20B. In this configuration, the tumor is securely held within cavity 2025. In some applications, the tumor is not connected to the subject, and the tumor is enclosed within cavity 2025.

An advantageous aspect of nsPEF pulse applicator 2000 is that while bottom arm 2010 is positioned to press the connecting tissue against spacer 2020, top arm 2030 is spaced apart from cavity 2025, and the cavity 2025 is viewable to visually confirm that the tumor is properly placed when secured by the rotation of bottom arm 2010.

Top arm 2030 may then be positioned so as to place top electrode 2035 adjacent the cavity 2025 containing the tumor. To position top arm 2030 near the tumor, handle 2042 is moved to the position illustrated in FIG. 20C.

Once inserted, the nsPEF pulse applicator 2000 may be used to apply nsPEF pulses to the tumor by applying nsPEF pulses to the conductive wires.

Once the nsPEF treatment is finished, the tumor may be removed from the nsPEF pulse applicator 2000 by positioning the bottom arm 2030 as illustrated in FIG. 20A. The top arm 2030 may also be positioned as illustrated in FIG. 20A to allow visual inspection of the removal of the tumor.

An advantage of the various embodiments of pulse applicators having a spacer as discussed herein is that the spacer keeps the electrodes with the separation of a predefined distance. With such an arrangement, applying a known voltage to the electrodes causes a known electric field between the electrodes. For example, an electric field pulse of 30 kV/cm may be applied across electrodes separated by a ½ cm spacer by applying a 15 kV pulse across the electrodes.

Another advantage of the various embodiments of pulse applicators having a spacer as discussed herein is that the tumor may be held within the cavity of the spacer for treatment without applying a force on the tumor with the electrodes.

Another advantage of the various embodiments of pulse applicators having a spacer as discussed herein is that the cavity in the spacer holds the tumor. As a result, the tumor is prevented from slipping out from between the electrodes.

Though the present invention is disclosed by way of specific embodiments as described above, those embodiments are not intended to limit the present invention. Based on the methods and the technical aspects disclosed above, variations and changes may be made to the presented embodiments by those skilled in the art without departing from the spirit and the scope of the present invention.

What is claimed is:

1. A pulse applicator, comprising:
a first arm, comprising a first electrode;
a second arm, comprising a second electrode; and
a spacer comprising a cavity, the spacer positioned such that the first arm and the second arm are on opposing sides of the spacer,
wherein the first arm, the spacer, and the second arm are movably connected to selectively position one or both of the first electrode and the second electrode in alignment with and adjacent to the cavity of the spacer, and wherein the first electrode and the second electrode are configured to deliver an electrical field across the cavity.

2. The pulse applicator of claim 1, wherein each of the first and second arms is independently movable with respect to the spacer.

3. The pulse applicator of claim 1, wherein the cavity is configured to receive and to form at least a partial boundary around a treatment site.

4. The pulse applicator of claim 3, wherein the cavity forms a closed boundary around the treatment site.

5. The pulse applicator of claim 3, wherein the treatment site includes a tumor.

6. The pulse applicator of claim 1, wherein the first arm, the spacer, and the second arm are configured to be movable such that, while at least one of the first arm or the second arm is spaced apart from the spacer, the cavity is exposed so as to be viewable.

7. The pulse applicator of claim 1, further comprising:
a first actuator configured to move the first arm with respect to the spacer; and
a second actuator configured to move the second arm with respect to the spacer.

8. The pulse applicator of claim 7, wherein at least one of the first actuator or the second actuator has an over center design.

9. The pulse applicator of claim 7, wherein at least one of the first actuator or the second actuator causes a linear and a rotational movement of the first arm or the second arm, respectively.

10. The pulse applicator of claim 7, wherein the first arm, the spacer, and the second arm are assembleable and disassembleable by hand, without any tools.

11. The pulse applicator of claim 1, wherein while the first electrode of the first arm is adjacent to the cavity and the second electrode of the second arm is adjacent to the cavity, the first and second electrodes are spaced apart by a predetermined distance so that the electric field has a magnitude equal to a voltage of a pulse applied across the first and second electrodes divided by the predetermined distance.

12. The pulse applicator of claim 1, wherein the first and second electrodes are configured to deliver the electrical field using electric pulses of sub-microsecond pulse duration.

13. The pulse applicator of claim 1, wherein at least one of the first arm, the second arm, or the spacer is configured to pivot about a pivot point.

14. The pulse applicator of claim 1, wherein the spacer is configured to hold a treatment site within the cavity during treatment without applying a force on the treatment site with the first and the second electrodes.

15. A pulse applicator, comprising:
a first arm, comprising a first electrode;
a second arm, comprising a second electrode; and
a spacer positioned such that the first arm and the second arm are on opposing sides of the spacer,
wherein the first arm, the spacer, and the second arm are rotatably connected, such that the first arm and the spacer are configured to face each other and to hold a tumor of a subject adjacent the first electrode and the second arm is configured to be movable so as to selectively position the second electrode adjacent the tumor, and wherein the first electrode and the second electrode are configured to deliver an electrical field across the tumor in response to an electrical pulse received across the first and second electrodes.

16. The pulse applicator of claim 15, wherein the spacer comprises a cavity configured to at least partially bound the tumor.

17. The pulse applicator of claim 15, wherein while the second electrode is adjacent the tumor, the tumor is occluded by the second arm.

18. The pulse applicator of claim 16, wherein the spacer is configured to keep the first electrode at a predefined distance apart from the second electrode when both electrodes are positioned adjacent and aligned with the cavity.

19. The pulse applicator of claim 15, wherein the first and second electrodes are configured to deliver the electrical field using electric pulses of sub-microsecond pulse duration.

20. The pulse applicator of claim 15, further comprising at least one actuator configured to move at least one of the first electrode or the second electrode linearly and rotationally.

21. A method of using a pulse applicator, the pulse applicator comprising a first arm having a first electrode, a second arm having a second electrode, and a spacer positioned such that the first arm and the second arm are on opposing sides of the spacer, wherein the first arm, the spacer, and the second arm are movably connected, the method comprising:
rotating the first arm with respect to the spacer to hold a tumor of a subject adjacent the first electrode;
rotating the second arm with respect to the spacer to align the tumor between the first and second electrodes; and
delivering an electrical field across the tumor in response to an electrical pulse received across the first and second electrodes.

22. The method of claim 21, wherein rotating the first arm with respect to the spacer causes tissue connecting the tumor to the subject to be compressed between the first arm and the spacer.

23. The method of claim 21, wherein the spacer is configured to keep the first electrode at a predefined distance apart from the second electrode when both electrodes are positioned adjacent and aligned with the tumor.

24. The method of claim 21, wherein the first and second electrodes are configured to deliver the electrical field having a nanosecond pulse duration.

25. The method of claim 21, wherein the spacer comprises a cavity configured to hold the tumor.

26. The method of claim 25, further comprising pressing a tissue connected to the tumor against the spacer while at least one of the first or the second arm is spaced apart from the cavity.

27. The method of claim 21, the method comprising, prior to rotating the first arm with respect to the spacer, positioning the spacer relative to the tumor to assist in positioning the first electrode adjacent the tumor.

28. The method of claim 21, the method comprising causing a linear and a rotational movement of at least one of the first or the second arm relative to the spacer.

29. The method of claim 21, the method comprising applying a force to a first actuator to rotate the first arm.

30. A method of using a pulse applicator, the pulse applicator comprising a first arm having a first electrode, a second arm having a second electrode, and a spacer comprising a cavity and positioned such that the first arm and the second arm are on opposing sides of the spacer, the method comprising:
positioning the first and the second arms relative to the spacer such that the cavity of the spacer is viewable;
placing a treatment site such that it is aligned with and at least partially bound by the cavity;
moving the second arm to substantially align the second electrode with the cavity such that the second electrode is adjacent the treatment site; and
moving the first arm to substantially align the first electrode with the cavity.

31. The method of claim 30, wherein positioning the first and the second arms relative to the spacer comprises rotatably moving the first arm relative to the spacer such that the first electrode is spaced apart from the cavity.

32. The method of claim 30, wherein moving the first arm and/or the second arm comprises pivoting the first arm and/or the second arm about a pivot point.

33. The method of claim 30, wherein placing the treatment site to be aligned with the cavity causes the treatment site to be observable by a user.

34. The method of claim 30, wherein the second arm is a bottom arm and moving the second arm to substantially align the second electrode with the cavity causes tissue connecting the treatment site to a subject to be between the second arm and the spacer.

35. The method of claim 30, further comprising delivering an electrical field across the treatment site in response to an electrical pulse received across the first and second electrodes.

36. The method of claim 35, wherein while the first electrode of the first arm is adjacent to the cavity and the second electrode of the second arm is adjacent to the cavity, the first and second electrodes are spaced apart by a predetermined distance so that the electric field has a magnitude equal to a voltage of the electrical pulse applied across the first and second electrodes divided by the predetermined distance.

37. The method of claim 35, wherein the electric field delivered across the treatment site has a sub-microsecond pulse duration.

38. The method of claim 30, wherein the treatment site is not connected to a subject.

39. The method of claim 30, the method comprising moving the first electrode with respect to the cavity by applying a force to a first actuator and moving the second electrode with respect to the cavity by applying a force to a second actuator.

40. The method of claim 30, wherein moving the second arm to substantially align the second electrode with the cavity comprises causing a linear and/or a rotational movement of the second electrode.

41. The method of claim 30, further comprising disassembling the pulse applicator by hand without any tools.

* * * * *